United States Patent [19]
Maley et al.

[11] Patent Number: 5,622,851
[45] Date of Patent: Apr. 22, 1997

[54] HUMAN DEOXYCYTIDYLATE DEAMINASE GENE

[75] Inventors: Frank Maley; Gladys R. Maley, both of Delmar; Karen X. B. Weiner, Syracuse, all of N.Y.

[73] Assignee: Health Research, Incorporated, Albany, N.Y.

[21] Appl. No.: 370,975

[22] Filed: Jan. 10, 1995

[51] Int. Cl.$^6$ .............................. C12N 9/78; C12N 15/63; C12N 15/09; C07H 21/04

[52] U.S. Cl. ..................... 435/227; 435/320.1; 435/325; 435/348; 435/358; 435/365; 536/23.1; 536/23.2

[58] Field of Search ................................. 536/23.2, 23.1; 435/69.1, 320.1, 252.3, 227, 240.1

[56] References Cited

PUBLICATIONS

Jackson, R.C., J Biol Chem 253: 7440–7446 (1978).
Chiu, C.S. et al. J Biol Chem 252:8603–8608 (1977).
Xu, Y.-Z. and Plunkett, W., Biochem Pharmacol 44: 1819–1827 (1992).
Maley, F. and Maley, G.F., Cancer Res 21: 1421–1426 (1961).
Gelbard, A.S. et al., Biochim Biophys Acta 182: 564–566 (1969).
Weinberg, G. et al., PNAS USA 78: 2447–2451 (1981).
Ellims, P.H. et al., J Biol Chem 256:6335–6340 (1981).
Maley, G.F. and Maley, F., in Advances in Enzyme Regulation, Weber, G., Ed, vol. 8, pp. 55–71, Pergamon Press, London (1970).
Geraci, G. et al., Biochemistry 6: 183–191 (1967).
Maley, G.F. et al., J Biol Chem 247:931–939 (1972).
Maley, G.F. et al., Biochim Biophys Acta 1162: 161–170 (1993).
Maley, G.F. et al., J Biol Chem 265:47–51 (1990).
Maley, G.F. et al., J Biol Chem 258: 8290–8297 (1983).
McIntosh, E.M. and Haynes, R.H., Mol Cell Biol 6: 1711–1721 (1986).
Maley, Methods Enzymol 12A: 170–182 (1967).
Melton, D.W., Bio Essays 16(9):633–638 (1994).
Hasty, P. et al., Nature 364: 501–506 (1993).
Snouwaert, J.N. et al., Science 257: 1083–1088 (1992).
McMahon, A.P. and Bradley, A., Cell 62:1073–1085 (1990).
Maley, F. and Maley, G.F., Curr Topics Cell Regul 5: 177–228 (1972).
Maley, F. and Maley, G.F., J Biol Chem 235:2968–2970 (1960).
Maley, G.F. and Maley,F., J Biol Chem 234:2975–2980 (1959).
Bianchi, V. et al., Mol Cell Biol 7: 4218–4224 (1987).
de Saint Vincent, B.R. et al., J Biol Chem 255;162–167 (1980).
Sargent, R.G. and Mathews, G.K., J Biol Chem 262: 5546–5553 (1987).
Meuth, M., Exp Cell Res 181: 305–316 (1989).
Weiner, K.X.B. et al., J Biol Chem 268: 12983–12989 (1993).
Weiner, K.X.B. et al, Mol Endocrinol 4: 1249–1256 (1990).

*Primary Examiner*—Robert A. Wax
*Assistant Examiner*—Kawai Lau
*Attorney, Agent, or Firm*—Nixon, Hargrave, Devans & Doyle

[57] ABSTRACT

The present invention is directed to a DNA molecule encoding a gene for human deoxycytidylate deaminase. The DNA molecule comprises 26,764 base pairs. A 1317 base pair 5' untranslated region is followed by exon 1 of 108 base pairs, which is followed by intron 1 of 402 base pairs, which is followed by exon 2 of 136 base pairs, which is followed by intron 2 of 20,303 base pairs, which is followed by exon 3 of 117 base pairs, which is followed by intron 3 of 1357 base pairs, which is followed by exon 4 of 97 base pairs, which is followed by intron 4 of 1554 base pairs, which is followed by exon 5 of 76 base pairs, which is followed by a 3' untranslated region of 1297 base pairs. Methods of using the DNA molecule are also provided.

8 Claims, 2 Drawing Sheets

5,622,851

HUMAN DEOXYCYTIDYLATE DEAMINASE GENE

The subject matter of this application was made with support from the United States Government (National Cancer Institute USPHS/HHS Grant No. CA44355 and National Science Foundation Grant No. MCB 931621).

FIELD OF THE INVENTION

The present invention relates to the gene for human deoxycytidylate deaminase and to expression and uses of the gene.

BACKGROUND OF THE INVENTION

Throughout this application various publications are referenced, many in parenthesis. The disclosures of these publications in their entireties are hereby incorporated by reference in this application.

Deoxycytidylate deaminase (dCMP deaminase) catalyzes the deamination of dCMP to dUMP. This reaction provides the nucleotide substrate (dUMP) for thymidylate synthase (Jackson, R. C., J Biol Chem 253: 7440–7446 [1978]) and Chiu et al. (Chiu, C.-S. et al., J Biol Chem 252: 8603–8608 [1977]). The activity of the enzyme is controlled by the ratio of dCTP to dTTP in the cell. In this regard, dCMP deaminase is allosterically activated by dCTP and inhibited by dTTP (Maley, F. and Maley, G. F., Curr Topics Cell Regul 5: 177–228 [1972]). Evidence in support of this thesis was obtained by Xu and Plunkett using an in situ assay (Xu, Y.-Z. and Plunkett, W., Biochem Pharmacol 44: 1819–1827 [1992]). A consequence of this nucleotide interplay is that the amount of dUMP available for thymidylate synthase is finely controlled by the end products of the pyrimidine deoxynucleotide pathway.

Several observations indicate the importance of dCMP deaminase in DNA replication. First, deaminase activity has been shown to be elevated in such rapidly dividing tissue as regenerating liver (Maley, F. and Maley, G. F., J Biol Chem 235: 2968–2970 [1960]), chick and rat embryo (Maley, G. F. and Maley, F., J Biol Chem 234: 2975–2980 [1959]), and rat hepatomas (Maley, F. and Maley, G. F., Cancer Res 21: 1421–1426 [1961]). Second, HeLa cell dCMP deaminase activity is highest in late S phase and subsequently declines in the following G2 phase (Gelbard, A. S. et al., Biochim Biophys Acta 182: 564–566 [1969]). Finally, the absence of dCMP deaminase activity in mammalian cells induces an imbalance in deoxyribonucleotide pools such that dTTP levels decrease while dCTP levels increase (Bianchi, V. et al., Mol Cell Biol 7: 4218–4224 [1987]; de Saint Vincent, B. R. et al., J Biol Chem 255: 162–167 [1980]). This imbalanced pool can lead to increased mutation rates (Weinberg, G. et al., Proc Natl Acad Sci USA 78: 2447–2451 [1981]; Sargent, R. G. and Mathews, G. K., J Biol Chem 262: 5546–5553 [1987]; Meuth, M., Exp Cell Res 181: 305–316 [1989]).

dCMP deaminase has been purified to homogeneity from a variety of sources including human spleen (Ellims, P. H. et al., J Biol Chem 256: 6335–6340 [1981]); chick embryo (Maley, G. F. and Maley, F., in *Advances in Enzyme Regulation*, Weber, G., Ed., Vol. 8, pp. 55–71, Pergamon Press, London [1970]); donkey spleen (Geraci, G. et al., Biochemistry 6: 183–191 [1967]); T2r+ bacteriophage-infected *Escherichia coli* (Maley, G. F. et al., J Biol Chem 247: 931–939 [1972]); and HeLa cells (Maley, G. F. et al., Biochim Biophys Acta 1162: 161–170 [1992]). A dCMP deaminase gene from T4 bacteriophage was cloned and sequenced (Maley, G. F. et al., J Biol Chem 265: 47–51 [1990]) and compared with the complete amino acid sequence of the enzyme isolated from T2 bacteriophage-infected *E. coli* (Maley, G. F. et al., J Biol Chem 258: 8290–8297 [1983]). A homology comparison of the latter with a deduced amino acid sequence of dCMP deaminase from *Saccharomyces cerevisiae* has been made (Mcintosh, E. M. and Haynes, R. H., Mol Cell Biol 6: 1711–1721 [1986]), and several regions of similarity were found.

The cDNA for human dCMP deaminase has been cloned and expressed as a functional protein in *Escherichia coli* (Weiner, K. X. B. et al., J Biol Chem 268: 12983–12989 [1989]). The cloned cDNA consists of 1856 base pairs and encodes a protein of 178 amino acids.

To provide further insight into the regulation of this important enzyme in DNA synthesis, a need exists for the elucidation of the gene encoding the human dCMP deaminase including the 5'-promoter region.

SUMMARY OF INVENTION

This need is met by the present invention. The invention provides an isolated DNA molecule encoding the gene for human deoxycytidylate deaminase, including the 5' and 3' untranslated regions, five exons, and four introns.

The invention further provides a method of altering DNA replication in a cell by locating a gene encoding human deoxycytidylate deaminase in the cell and altering the nucleotide sequence of the gene. This alters the level of deoxycytidylate deaminase produced in the cell which in turn alters the catalysis of dCMP to dUMP. Altering the catalysis of dCMP alters the levels of these nucleotides in the cell, which alters DNA replication in the cell.

The present invention thus allows the analysis of the structure of the human dCMP deaminase gene and the characterization of the 5' promotor region of the gene. This in turn provides information on the regulation of the dCMP deaminase gene in DNA synthesis, which permits the formulation of chemotherapeutic agents targeting the deaminase.

BRIEF DESCRIPTION OF THE DRAWINGS

These and other features and advantages of this invention will be evident from the following detailed description of preferred embodiments when read in conjunction with the accompanying drawings in which.

DETAILED DESCRIPTION

Figure 1:
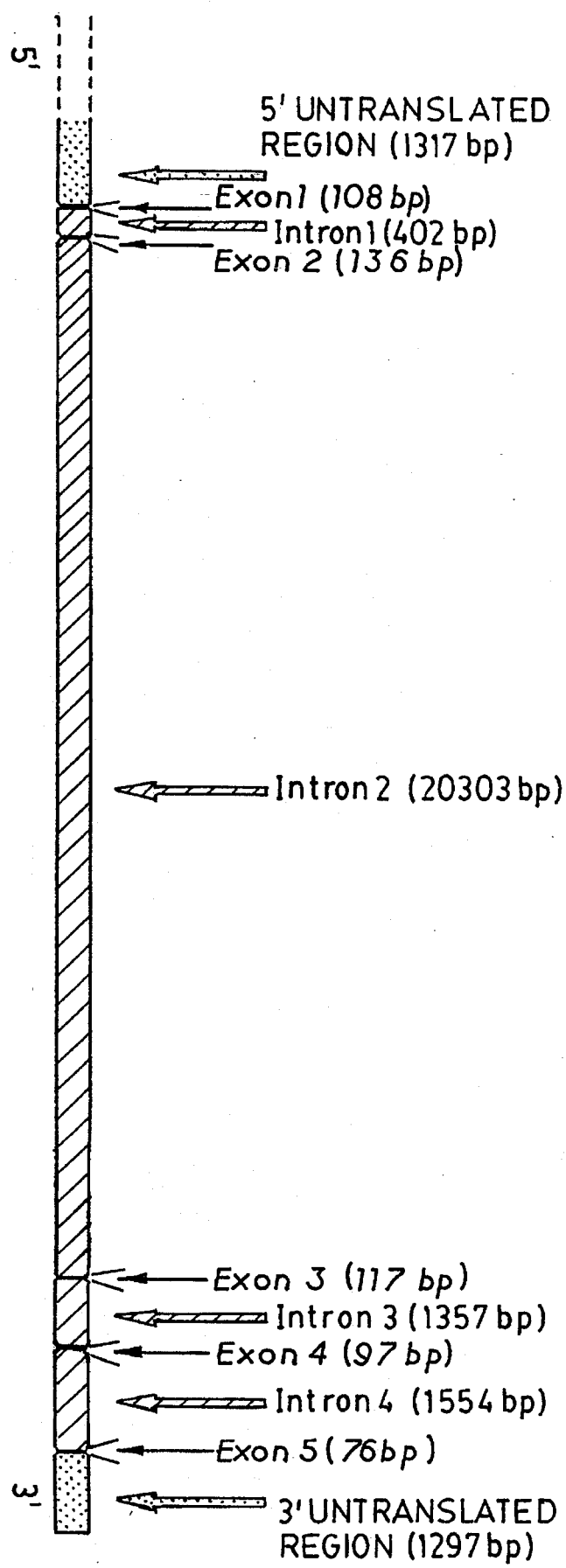
FIG. 1 shows the structural arrangement of the gene for human deoxycytidylate deaminase.

The present invention relates to an isolated DNA molecule encoding the gene for human deoxycytidylate deaminase. The gene contains 26,764 base pairs, with the sense strand corresponding to SEQ ID NO:1:

```
GAGCTCCAGT TCTCTCTGTT TCTACAGCTG GGCCTCAGTC CTCACAGGGC
TCTAGTGGGC      60
GTTCAGCACA CCAGGAGAAG GCGCCCAGGG GATTAACAGG ACCCTTCCCT
CTCCTGCTCT      120
TCCCTCGCCC CCCATGGCTC CCCCTCCCTC CTATTTAGTA GGTACTTCTC
CAGCACCCCA      180
CAGCGATGAT GGATGCTGGC CCTAAAGCCA GGTGGGAAAC CAGGCTGATT
CAGCACCTGT      240
CTTTTCCTGT TAGGGGGGTT GCCAGGCCTC TCAGATGTGG GGCAGCGTAA
TCAGTGGGTG      300
ACCGTGGTTC CCAGCACCCA CTCTCCACTG CATCCTTGTC TTAGGCACTG
CCGCCCTGCA      360
CTGTAGCAGA TGCCTAAATA AAGTGTGGAG CCTGAAGCAG AAGTTTTGGG
AGATGCTTGC      420
CTTCCTTTAG ACCACATTCC TCGCCTTTCT CAAGATTTCT CCGTGGTACC
CACCCCGTTT      480
TTGTGTTGTC TTCCTTCCTT GCCCTTGTTT CATTCCTTTT GAAAGCGACC
ACTCCCCTGA      540
AGTCCTAGGA CCCCCTTCGT GGGCTCTCCC TGCCGTAGAC AGTCTCTGCT
TGCCCCTGGT      600
AAACTACGTT CCAAAAACCT TGCTTTAGGA GTAGCACTTG ACGTTTTTCA
TAGTTTCTTC      660
TCATGTAATT CATTACTCGG AGTTGATAAC TTCTGTCCCA TCTGGATTAT
TGAGGAGAAA      720
GGGAAGGGAA AAATTATCTG GTTAATATCA GAGTTGGGAA GGCTTCAGAT
GTTTTCTTTG      780
AATCCGTCTG GCATGGATGA TAATCCTGTG TGGTTTAGGT TAAGTTACCT
AAGTTCTCTG      840
AGTCTGTGTA AGATGGGATG GCACTGTCTA CCTTAGCTAG GAGTAAGGCT
TGAGTGACAT      900
GATGTGTATA AACTTTAACA ATGTCTGGAA TCTATAGATG ATCAATAAAT
ATTTCTTTTT      960
TCCACCCTCC TCCTGTGCTG ACTCCGCTTT GTAAGGGAGA CAGGTAAAGG
ACACAACAAT      1020
TTGTAGGCTG GCATAAAAAA TCCTATGAGA GAAAGCAGTA AATAGATGAA
ATATTTGGGA      1080
ACGTGAAGCT ATAGGTTTCA AATTCAAACT TCTGAAATAG GAAATTTCTT
AAGTTTTTAC      1140
TTAAGACCAG AGACTGTTTA GGGCCCATGT GCTGTGATTT CTGATTGATA
AATGTAGCTG      1200
AAGTTGCCCA TGTTTAGAGA TTTAAAGGTT CAGTGTGGTT GGGTTGAACT
GGAAAACAGA      1260
CTTACTAAAA TGCTTCTCTC AACTTCTGTT TTGTCATGTT TTTCTTCTAG
ACCCAACATG      1320
AGTGAAGTTT CCTGCAAGAA ACGGGACGAC TATTTGGAAT GGCCAGAGTA
TTTTATGGCT      1380
GTGGCCTTCT TATCAGCACA GAGAAGCAAA GATCCAAATT CCCAGGTAAA
TGAATTTCAC      1440
GGGAGAATGC TTAGATACTC ACAGGCAAAG AGATTACTGC ACATGAGCAG
AAAGGGGAGA      1500
CTCAGTGGAC GCCTGTCAAC TTAAAAGTGC AGGGTCGGTC TGCCTTTTGT
GCTGCGTTTC      1560
TACAAGCTTA GTTCTTCCTG TGAGACAGAA AATTGTCACA TGCCATTGTT
AACTGCCTCT      1620
TGTGCCCCTT CTGGGACTGG GGGTGCACTT TCCTTGGCTT GTGGGTGCTG
CCACAAAAAA      1680
CCAGGCAAGG AGACCGACAG CTCTCAGCAC CTGCAGCAGC TATGCGTCTG
TTTTGAGTTC      1740
TGCAGTCCCC CTGGTTTTAT TCCCTGCTTC CACAGCGGCA GACCAGCCAG
TTGCAGGCAC      1800
CAAGCCTTTG GGCATGTTTC CTTCTAGGTC GGCGCCTGCA TCGTGAATTC
AGAAAACAAG      1860
ATTGTCGGGA TTGGGTACAA TGGGATGCCA AATGGGTGCA GTGATGACGT
GTTGCCTTGG      1920
AGAAGGACAG CAGAGAATAA GCTGGACACC AAATACCCGT ACGGTAGGGC
AAGTTTTATG      1960
TCCCATTCTG CTTAGTGACA TAGCCTGGTG AGTGCCTAAT TAAGAAAGTT
GGTCAGAAGG      2040
CATCATCTCC CTTTTGTCAT CAACAACTGG AAAGAAAAGT ATCCTACTGA
ACTACCCCAA      2100
TTTCCTGGCC TTGTCTCTTA AGTTCCAAAG AGAGCCACGG AGAGAAGCAT
GGTAGTGGCC      2160
ACACAGGCTG GCCCTGAGAT CCAGGGCTCT GCTGCCTGTG CTGAGCCTGG
CAGGCTTCAC      2220
TGGCAACCTG CTGGCCTGCA CCACACCAGT GCACTGATAG TCGGCGTCTC
TGCAGAGGGT      2280
CACAGCCCCT TGCAGAGATA GCTGAGGGAT GTGCATGGTG TCTCTGTGGG
TTCCTTTTTT      2340
TACTACTTGG AAGCAGGGTC GGCTAACCAG GGGCTGGCTC GGGCTTTGGT
CTGATGAGAA      2400
```

```
GCAGGCTTCA TTCAGCCCAT GTGCCTGATG AGAACATCTG GCTCAAGCTC
ATTGCTGGCA    2460
AGCAGGAATC AAACTGTGAA CTAGACATCA GGAGATGGAG GATCCAGTTG
CTTCCTCCAG    2520
TTACAGGGGA TGCTGCAATT TCACAGTAGG CTGTGGTCAG ACCAAAAGCC
AGAAGTGAGG    2580
CTGGGCACGA TGGCTCACGC CTGTAATCCC AACACTTTGG GAGGTGGAGA
CGGGCAGATC    2640
ACCTGAGGTC AGGAGTTCGA GACCAGCCTA GCCAACATGG TGAAACCCCA
TCTCTACTAA    2700
AAATACAAAA ATTAGCTGTG CGTGGTGGCA GGTGCCTGTA ATCTCAGCTA
CTCGGGAGGC    2760
TGAGGAAGGA GAATCGCTTG AACTCAGGAG GTGGAGGTTG TAGTGAGCCA
AGACTGCGCC    2820
ACTGCACTCC AGCCTGGGTG ACAGAGCAAG ACTCTGTCTC AAAAAACAAA
ACAAAAACAA    2880
ACAAACAAAA AACAAAACAA AAACAAAGAA AAGAAAAAGC TAGAAGTGTA
GAACTGTAAA    2940
CCTTTGGCTT GACTGTCTCT GGATTTTCCC CTTGAAATTA GGGAAGGCTG
CTTCTTAGAG    3000
TTTGTTGCCT GTCTAAGCCC CAGGGAAAAT TCCTTCAGAG ATTGCCTGGG
AGGGTCCAGC    3090
CATAGCTTTA CTTTTCCTTG CATTCCTTGG AGAATATGCA AGCAATGCTG
GAAAAGAGGC    3120
AAATCATGCT GGGTATGCAG GTTGCTGATT TTTGTAAGGT TAGGCCCTGT
ATTTTATGTC    3180
TGAGAATGAA CAGACTGGCG CTGTTGGAAG TGAAGGGAGA GTAAGGCCAT
CCAAATGGGA    3240
AAGATTGTGT CTTCAGGCCA AGGCGTGATG TACGACCTTT CTTCTTTGTT
GACTCTCCTG    3300
GTAGGTTTTC TTCTGGGTTT TTCTCATGAA GAATCCAAGT CAACATTTAG
TCTAATTTAT    3360
ATATTTTTAC TAATGTTCCT GGACCTCAAT CATGTTAAAT AAGCCCCATA
AATTTCTTTC    3420
TAAATTGCCT AGGGGCAACT TCTCCATGTT TGAAAGAAAA AGTTAAGAGG
TACCTGGAGA    3480
GAGAGGAGGA ACTGAGGACT GCAAAGCAGT CTGGGTTTCC AGGATGTGAA
AAGTAGTTTA    3540
GGGATGAAGG GGACCGAATC CTCAGATCCT TGATTTAACC TCACCCTCCC
TCGTCGGAGT    3600
GGGAAGAGAG GATGGAGTTG GGGGAGGGTA AGACTGTCTT CTCAGCACAG
CTTCAGAGCC    3660
GGTGGTAGTG GATGACTAAT TAGAAAAATG CGCGGACTCA GAAACTGTCA
CCCTGATTTT    3720
GATTCTATAA GCTTTTGATG GTAAGAAAGA AGGGAAGTGA TTAGTTGTTT
TTAAGTCCAT    3780
GCAAAGATAA TTTTTCACAG TGCGGTTCAA AGTCCCCTAT AAAAATGGTG
AAAGTGGAGG    3840
GTCGGATATG TTAAAGGTCT GCATTGAACT GTGTGACGGC CACAGTCAGT
ATGTCACCGA    3900
GTCTGGGCAG TGAAATATTG GCCCTGGGGC TGGACTTTGA TATGGAGGAA
TTCTGGGGGG    3960
ATGGCGGTCC GTCATACTCA AGCTGGTGCA AAAGATACCC GTGGTTGGAC
AGTGCGGAGG    4020
GGTCCTGGGT GAGCACTGAG TGGGCCTCCA ATGGGGCCTG TGCCTTCTTC
AGTCACCCAG    4080
AGCCCCCAGC AGATCTTTAA GCAGTGACCT GGAAGCCAAG GGCCATGCAG
TACATTTGCA    4140
GCACCTGCCC CACACCCCAG ACTTCCCAGC TCTCCTGACT TCCCGTGTAG
CTGATTTTGT    4200
TGGTTATGAG ACACTGCCTT TTGTCCAAAT TGAGGAGAGT ACCTTTCAGA
GCCCCTTTCT    4260
AGAAGGAATT TTTTAAAAA CCTGCATAGG TATTTGTCCA ACTTCACCGA
TTGTTTTTA    4320
TTGAATAGCT CCTGAGCTCC TGGGCACTGG TTGTCTGTCT CTGCATTATT
TTTTATTATC    4380
CATATGATAC CTCTAGGTTT TCAAAGCTCT TTGCTCTTAC TTATCAATTA
TTCATTTATA    4440
TGTAGCTGTG TTAGAATGTC GACAGTTTTC TTTCACGAGA GTAAGCTTGT
AATTTGATGT    4500
ACCATAAAAG TTGTAGAAGG TATTAAATGG TTTCTAAAAG GCATTTAGTA
TTACTGCCGC    4560
CATAATACAG TAAAGATGGG CTTAAAGTCT AAATGACGAT GACTGTGTAT
AAACTGTACA    4620
CTTGTTGTCT TCTCAAGGTT TTTCAGGCCA CAGAGAAGTA AATGTTTGGA
TTGCCTGGGA    4680
TGTCACAGAA ATGTTTGCTG ATAATTGACT CAAATGCAAA GTCTTTTTTT
TTTTTTTGC    4740
TTTCGTTTTA AGATTTTCAA AATTAATTTA AAAAATAAGG GGATACTGCC
TGGAGTTGGA    4800
```

-continued

```
TAGCTCAACC CATTCTTTCC TCATCTACAT TAATGGTGAC TGAGCTGCTG
TAGCAGGAAG   4860
GGTAAATTCA TAGGTTAATC CCTGTAAAGG AGCTTTAGAG ATTATCTCGA
GTTCTGGACA   4920
ATGATTTTTA ACTCTTTTGA ATGTACAGGA CCCTCTTTTA AATGCTGAAA
AACTTCCAGG   4980
ACCCCTGCAT AATGCTAAAT TCTTAGTATC TTTTGAGTAA GAAACTCCAC
AATGACAAAA   5040
ACTACTTCGT ATCAGTAACA TTTTTTGTTA ATCTGAACTT TATTAATTGG
ATAGCATTTA   5100
TGTATGTTTG GGAAAAGTTT ATGTATGTCC TGGACATGGG ATTTATCCAG
TTGTGGATAT   5160
GCTTGGACCC CTTGCAATAC CTTAGTAGTG TCTCAGGGTT CTATGCCCAC
AGGATCTAAG   5220
CCTCCTCCTT TCTTGTAAGT AACTTCTATA ATGTCACACA TGCAGGGTGA
CATCTCCTAA   5280
TTCCAAGGTC AGTGCTCTTC CTGCTACCTC CCTGTGTCTC TCCTGTGGGG
CACATGAATT   5340
CAGCTGTACT GAAATGCCAA TCATTGTCTC ATTTTTTTTT GCAGTTGATC
AGACTGAGGC   5400
TCCGATAAAA TAATTACTCC TCAGAGATCA GGAGCTCGGG GAGGGGTGGC
CTGTGTCCGG   5460
CATCATGCAG AACAGCATGC GTGGCTCACT GTAACATTTC TTCAAAGGGG
AGTGCAGTGG   5520
ACTGAATGTG TCTCCCCCCA AATTCACATG TTGAAACCCT AATTCCAATG
TGCTGATATT   5580
TGGAGGTGGG GCCTGGGGGA CGTAATTAGG CCATGAGGGT GGAGCTCTCC
TGAATGGGAT   5640
TAGTGCCCTT CTAAAAGGGA CCCCAGGGAG CTCAGTTACT CTTTTTCCAT
GTGCAAGGAT   5700
AGGCGGAGAA GATGGCTATC TGCAACCCTG AAAGGAGACC TTGCCAGAAT
CTAACCATGC   5760
TGGTGTCCTG ACTTCCAGCC TCCAGAACCA TGAGAAATAA ATGTCCATTG
TTTCTCAGCC   5820
ACCCAGTCTA TGGGACTTTG TTATAGCAGC CCCAAGGGAC TGTGACAGGG
AGCTTGAGAA   5880
CTGTGTAAAT TTGAGTTTAC CAAATAACAT ACAGCTTAAT ACTGCTTTAT
TAATTCCGTA   5940
AGTCGGAAGT CATTAGTCCT GATTGATGCC TTGTGGGGAG GAGGGAAACA
CACACTACTT   6000
GTAACATAAT AGGAAGATGG AGCTTTTCCT GGGCTGTGTC TCTAGAGAGT
TATTTTTAAA   6060
AGGGTGTTTT TGTTCTTCCA GTCTTGGGAT CAAAACTTCA TAAAACTATT
TTATTATAAT   6120
GTAGGTATTA ATGTGGAAAA TGAAAATTCC CTCTGCTAAA GAAGCTTTTT
ATTCCATCCT   6180
TTTCCTGAAA AATCCAAAAG ATAAATATGAT GTCAGTAACA TTAAGTGGCA
GGAAGAAGGC   6240
AATGTTATTA TACTAAGAAT CTTTTCAGAT GAATGACAAT TAAAAAAGAG
GAAGCAGCAG   6300
ATTTATCTAA TTTACAAGAT TAAAAAAACTT GGGAAGATTT TTATTTTCAT
GAGGGGGTGG   6360
GTTGCTAAAC CCGTGATGAA GTATTCAGTT GACATTTTTC ATTCCTTTTT
CTTTGTGGAA   6420
TTCATTATAG TGAAGCACAT TTAATCAAAA TACCAATGTT ATCAAATGAG
GTAAAATACT   6480
CTTGGTGATT CAGATATCAC TCTTTCCTTG GGTTTTCGTA ACCGATTTTG
ATGATATAGT   6540
TTACAAATTA GAGAGTTGGA GAATTAACTT GTTCCCGTTG TTAAACTTAA
GGGAATTTTT   6600
AGTAATGCTT GCCACATGTA TCCAGCTGCC CAGCACTTGT GGCCTTGCTG
ATTTCTGCTG   6660
GCAAAGGGCT CTGGGTTTTG GTGAGTGCCT CTGTGCTTGG CCTCCTATCC
CACCCAATGG   6720
ACCAGGGAGC CAGGGTTGCT TGGCCTGCTG CATCTCACTG CACCAGGGAG
GGAACCGTAG   6780
CATCTCAGTG TCCCCAAGAG TCGGGGGAGG CCTCACTCTG AGTGCGTTGG
GTAGAAGTGG   6840
GGCTCTTACC CGAGTCAGTT CCTATGTCTA CAGGGATACT CTAAAAAGGA
TGTAATGCTG   6900
GGAAGGAAAA TGCTGAAAAA CCTGGAATTA ATTAAGGCGA AAGAGTTCAG
CAGAGCATCT   6960
TAAACACCTT TGCCAGTGTG GGGCAGTGCC TCTTTAAATT CTCTATTTAA
ATTTCATCTT   7020
TATTTTTCAG ACTTAGCATA TTGTTAAGCA TGCATAGATG TCACTTTTGT
GATTACTTAG   7080
CCATTTACTT TACCCCCTTG AACACTGACA TTTTCCTGAC TGCCATGCAC
GTGATATATT   7140
TCTTTGGCAT CTGAAAGGTT AGTGTTGAGA AACTAATTTA TCAAGAAGTT
AGGAGGCTGA   7200
```

```
TCCTTCTTAA GATATGACTT CCTCACAACT TGTAAGAGCT TCTTAGTAAT
TAAGATCAAA    7260
TTTGTTCTTT CCGTCCTGAA ATTGAATGTC CTCTGGTTTC GTTACTCAGT
CCATGAATTT    7320
GATAACTTGC TGTTTCTTTT CCTGCAGAAT TTAATTTCAC TTAAAGCTTC
CTGCCGCTCC    7380
TCCCCTGCCT GGCCTTCTAC TAGTTGTGGC CCGACAGCAG GTCTAATTAG
GGACTTTTGT    7440
ACAAAACTAC TGTTATAATC AATGGAAAAC CTTTGAACAA CTGCATAGAA
AAGAAATTAA    7500
GTAGATTATT TTTACGAATC AAGGGGCAAA CTCAGCTGTG ATCGTGTGGG
GTTTCAGATA    7560
AACAGAGGGA CACACCAGTG TATATATGAG TCTTCTCCCA CCCACTAAAA
TCAACCAGCT    7620
CCATGTAAGC ATGTTTTACT TTAAGATATA ATTGTTTATA AACAGTTTTC
AGAAAGGAAT    7680
AAATAATGAT ATTTTAATAT AATTTATTTT GATATTTATG TATTTTTATA
GTTACAGAGT    7740
TAATTATTTT TAAAGTGCTA GAGTTTACTA TTTCATTATG AATATCTATG
AAAGACATAT    7800
AGTAACAAAA TAACTCCTTG TTTTGAAGAG CACACATGTT AGGAAAAGCT
GAAATGTTTG    7860
GGGATTGGAC CTACCCATGA AAATACACAT ATCTGTCTCC TTTCTATAAA
AAGTGACTTT    7920
TGAGTCAGTT CACCTCGTAG AAGTTTGAAA TAAAACTTAA TCTAAAGTAG
TGGTTCCAGG    7980
GTTCCCAGAA GTGGGCTGAA GTTTATCTTT GTACTGTAAC TCTCAAGATA
AAAGGTTTGT    8040
TGAAAAATTA GTAGCCTTGA TAAAATGTCA GGGGCACATG CAAACTAATT
TAGAAAACAG    8100
CTATGTTAAG TATTTGAGCA CATTAATGAT CTGAATGCAA ATGGATATTC
CTTCTTTATT    8160
TCTTCTTCTT CTTCTTCTTC TTTTTTTTTT TTTTTTTTTT TTGAGACAGA
GTCTTGCTCT    8220
GTCACCCAGG CTGGAGTGCA GTGGCACAAT CTTGGCTCAC TGCAGCCTCC
ACCTCCAGGT    8280
TTCAAGCGAT TCTCCTGCTT CAGCCTCGGA GTAGCTGTGT GATTACAGGC
ACGTGCCACC    8340
ACGCCTGGTT AATTTTTGTA TTTTTAGTAG AGATGGGGTT TCACCATGTT
GGCCAGGCTG    8400
GTCTCAAACT CCTGACCTCA GGTGATCCAC CCGCCTCAGC CTCCCAAAGT
CCTGGGATTA    8460
CAGGCTTGAG TCACTGTGCC CGGCCACTTC TTTATTTCTT TAACTTTGCT
AAGTCTTTGC    8520
TTAGAAACAC AGGGATTGCT GTACAGTGTG GTTACCTGAG AATGATTACT
CTCATAGTCT    8580
TGATTCTGGT GATCTGTTCT ATAATCAGTT GTGCTGATTT TGACTGATCT
TCTCTGAAAT    8640
TGGCTGAAAT GACTAAAGCT TTATTGTATT TTGAGTTTTT TTTAATCCGG
AATCTCCCTT    8700
CAGGAGTTTT GTTAATACCA GCTATATTAA AGTAGAAATAT GAATATATTG
TTTGCTCCCA    8760
GAAATACACA ATAAAACCTA GTTCTTAGAG ATTTTTGCAA ATGTTTGTAT
TGCTTTTTAC    8820
TTTTACTTCC TGAAGACTTT TTTTTTTTAA ATCTGGATAG GGATATGCAT
GTCTGTAATA    8880
CACACATTAG CTAAGTAAAG CCCCATAGTG CTTAAAACAA CAATTGCCAT
ATTCACACGA    8940
AAGATCCTGG AGCCGCCGTA AGGAGCCAAG GGTTCCAGGT TTGGTATGTT
CATGCCCAGT    9000
GACTGTGGGG CTGTTAGAGG CATCACCTGA CATTTATTTC TCAATATCTC
TATGAAGTAA    9060
ATTATCACTG AAGATTCTTC CAGTTCTCTT ATTCCAAGGA AAAATATAAG
TATTATAGCT    9120
TTGATGGCAT TAGATTAGTA TCTTTTTCTC AGCTTACGGA GTTCTGAAAG
CGTTCTCGGT    9180
CAAATCAGAG CTGTAAAAAG CTGTTGGAGG CAATGCCACA GGGAGAATGT
GCATGTGTAC    9240
ATATGGATAA ATTAATAGAA ACAGGCGCCT TTCCCTCCCT CCTCTAACGA
TTAAAGACTG    9300
GCGCAGTTCT AAGATGAATA TAGACCATAT GGAGGTACCA TGCATGAATA
GGAGGGGACA    9360
GTCAGACTGT AGGTTACCTC ACAGACATGC AGATTAAAAG ACATTGGATG
AGAAAAGGTT    9420
GGATAACAGC AATAAAGAAA AAGATCCTAG CTGAGTATGG AGTGCACGCC
TGTAATCCCA    9480
GCACGTTGGG AAGCCGAGGC AGGTGGATCG TTCGAGTTCA AGAGTTCAAG
ACCAGCCTGG    9540
GCAACATGGC GAAATCCCGT CTCTACAGAA AATACAAAAA TTAGCCGGGT
GTTGTGGCGT    9600
```

```
GCAGCTGTAG CCCCAGCTAC TCCAGGGAGG CTGAGGTGGG AGGATTGCTT
GAGCTCGGGA    9660
GGCCCAGGCA GCAGTGAGCC AAGATTGCAC CACTGAACTC CATCCCAGAC
GACAGAATGA    9720
GAGACCCTGT CTCAAAAAAA TTAAGAAAAA GATCCTATGT CTAAGTGAAA
GAAAATGTAT    9780
GATTACATGG GACACGCTGA AAACTCTTTG AAAGAGACAA GAGGTTAAGA
CCAAATAGAA    9840
AGAAAGGACT TTAGAAATTC TTTAGAGAAC AAGTCAGCAT GACAATATTT
ATTCAAACAG    9900
AGATACTTGC TTGACATTGG GAAATCCCTG TGATAAATGC AGGATACTGG
TGAAGGCAAG    9960
AGAGTTGCAA TGCAAGGGAA TGGGCGCTCC CCTTGCTGAT GCTGTCTGAA
GGGTCGGTGC   10020
CAACCAATTA GTGGAGGTGT AAATTTTCTC TGTGCTTCTT TCAAATGATA
GATGCCATAG   10080
TAAATTTAAA ATATTGATAT GATAACTGAG CATGAATTTT TTAATTCTGC
AATTAAAAGA   10140
CTTTGTTCAA AATGCCATTA ATTTTGAGTT TAGGTGAATA AAGGGAAGCA
GAATTCTTCT   10200
GTCATTTTTC CTTCTCCATG TGAGTTATCA CTTTTTAGGA ATTAAAATAA
GTACTAACGA   10260
GTCACCTGTT CTCTTACCAG TTTCAGTTGT CTGCTGGTGA TGGGGATGAT
CTCTGGAGTC   10320
ATCTTTCTTT CTTTTTAAAA TCCTAACTCT ATTTTATAAT GCGTTGGAGT
TTTTCAGACA   10380
CCATCACATG TGGTCATTTG TTCATTCAGC AGACACTTCT AGGGCATTTA
TTATGTGTTT   10440
TACATGCCGG GCACTCTGCA GAGGTCAACA GAATGCCATG GGAGGGTCTC
TGTTTTTGAA   10500
GAGTTTGCAG ACTAATTGTG GAGGAGGTAG ACATTAATGA AACAAACAGA
TATGATTGAA   10560
TATTCCTTTC TGAGGCAGTC ACTTTTTTTT TCTTTTTTAA TGAGATAGGG
ACCAGACCCC   10620
GAATCTGCCA GCCCCTTGAT CTCGGACGTC CCAGCCTCCA GAGCTGTGAG
AAATACATTT   10680
CTGATGTTTA GAAGCTACAA ATTTATGATA TTTGTTAGAG CAGCCCAAAC
AAACTAGGAC   10740
AGGTTGTGTG TATGAACTGG ATTGTTCTGG GGCAAGAGTG GAAACAGCGA
CTCGCCAGCC   10800
GGGAGGTGAC GTGGTGTACG ATGCGAGGGC CTTGGAGGGG GTGGGTGCTG
GGGCTGGAGA   10860
GGCCTGGCTG GAGATGGGGT GTATTTTAGG GGCAGCATCA GGAAGATGGC
GTGATAAAGG   10920
GTGGAAGAGG TAGATTGACT CCCCCCAAAT GGTTCTGGTT GCAGTAGCTA
GACAGGCATG   10980
CTGAGGAGGA GAAGCAAGAT TTTGGAATGA TCAAGGAAGA TTTAGACACC
TGAAGGCTGA   11040
GGTGCCCATG AGCGCTCCCT GCAAAGGGTT GGGTGGTCAG GTGGGTGTAT
GAGTTGGGGA   11100
TTAGTCCCGA CTGGCTGTAG CAGTACAGGT ATGTCAGTGC CAGCGACCTG
GGTGGCTGAT   11160
GAAGGGAGCA TGTGCAGAGG CAGTAGGAGT AGCTGTGGCT GAGCCCTGAG
GGCTCCAGCG   11220
CTTAAGGTGG TTGGAGAAAG AAGGGCCCGT GAGAAGGAGC ACACAGAGCA
GTGTTTTAAG   11280
AAAGAAGGCC TCATTTTGGG AGGCCGAGGC GGGGGGATCA TGAGGTCAAG
AGATCGAGAC   11340
CATCCTGGCC AACATGGTGA AACCCCATCT CTACTAAAAA TACAAAAATT
AGCTGGGCGT   11400
GTTGGTGCAT GCCTGTAGTC CCAGCTACTT GGAGGCTGAG GCAGGAGAAT
TGCTTGAAAC   11460
TGGGAGGCGG AGGTTGCAGT GAGCCGAGAT CGCGCCATTG CACTCCAGCC
TGGCAACAGA   11520
GTGAGCTTTG TCTAAAAAAA AAAAAAAAAA AAAAGAAGGC GGGCTTGTCA
GCTGTATCGG   11580
AGGCTGCCAA GAGGCCTAAG ATTAAAAGTG TTCATGGGGT TCAGCAACGT
GGAGGTCAGA   11640
GGTGATATTG CCAAGTACAG TTTCAGCCAA GTACAGTTTC AGCGGAGCAA
TAGGGTTGGA   11700
AGCCACATTG GAGCCTCTTG AAGGAGAACA GAGGGTGAGA CAATGGGGAC
AGCTTTATTT   11760
AGATCGGGCT TTGGGATGTG TGGCTGAGAA GAGAGCAGAG AAGTGGGGTG
GTGGCTGGAA   11820
TGGAGATAAG GCCACGGGAA AGGATTGCAT TGTTTGTAGG ATAGGAGAAT
CTGGTTTTGG   11880
CTTTGGTTTT TGCTTTTCTG TAGCAGACAT TTGTTTGTTG ATGGGAATAG
TCCAAGACAG   11940
AGAGAGTGAG ATAGAGATTT CTGGAACAGA GGCAAGGTGC TCAAGGCTGT
GAGGATCGGT   12000
```

```
CTCTCAGACA CCCTGGTTGA TAATAAGAGG AAGGACTGAG AGGGGAGGTG
GGAGGACAGC   12060
AGACACAGGG TCCTGGAGCG AAAGGCAGAG TGTGATCAGT TGCACCATTC
CGGTGGAGGA   12120
AGCAGGGTCA TCGGTTGAGA GAGCTGGGAG TTGGAGCTTG GATGCCGGGA
GAAGAGAAGA   12180
GCTGATTGTG TGGGGTGGGA GAAGAATGTC CTAGGAATGT AGGGCAGTGT
CAGGAGCTCA   12240
CATCTTATCT GAGAATCTCG AGTTGGGCGG TTGCTTCCCA TTTTCTACCT
GCAGACCCAG   12300
GATCAGTGCG CTGCCTGAGG CAGGCCAGGG AGAGCTGGAA TTAATTAGAA
CACACATCCC   12360
AGCTCCTCTT CCAGTGCCCA GTGCTCAGGC CCGGTTCCCC TCTAAACGCT
ATTAACACAC   12420
AAAGGAGGCT TTTAAGCTCC ATCACAGTAC TATCAGCGCT GATTAGCGCT
CTGTTTCTCT   12480
TGGTGCTGTT GTCACGCATT TTAGGCATCA CGTGTGCATT TCACATGAAC
AGTGGGAAGG   12540
GAGTTGGCAT GGCCTACCGT GGATGCAGTA CAGCTATTTC CACATCCTCC
TCCTCCTGAC   12600
CTGATTGTGT GCCCTTAGCC CATAGGAGGC AGTGTAATTA GAGTTCTGGG
GGCTTTATTA   12660
CCAATAATGG CCTTACCACA GTCAGAAATC TCTTTAGCCC TGAGCACTAC
CATTGGGGCT   12720
AAGTGGCTCC CCTGGGTGCC GTGAGTTGTC ATCCGCAGCT TTACGAAGAG
GCATTGAGGA   127&0
AGGGGGCAGG GATGGGGAGC AGAGTGGGAG AGAGGGAAAA AGAAATGGGT
ATTCTCACAG   12840
GCAGGCTGGA TTGGGCAGGC CAGGACAGCC TGGTCTCAGG TGGGCACACG
TGGGAGAGGA   12900
TGGGAAGCAC TCACATGTAG CAAGTAGCTT GTCTGTGCTG TGCTCTTGAC
AGATGTTAGT   12960
CTTTCTAACC GTTCTTGGAG AGGGACTTTT CTCTCTATTT CTTAGGTCCG
GAGGCTGAGG   13020
CTGAAGAAGA TGCTTGACTG GTAGGTTGTG GACAGTGTGT GAGGACATGG
TAGGGAGGAA   13080
GCAGAGAAGA CAGGCAGAAC CAGGGGTCTC CAAGACCCCT GAGTGCATTG
TTGCAGGAGC   13140
GGAGACGGAA GTTCTTGCCT CAGCTTTCAG GGCCCTGGGC TGTGGGCAGG
CGGATGGGCA   13200
CCCTGGGTGT GGAGGCTTCC CTCAGAGCCT GCAGGATGGG CTGCCTTTTA
CGTGAGTGAC   13260
CCACCACTTT CTCCCCAGAC CTTGGTAGAA TTCCTTTGCG CTGTCATTTT
CTTCTAGCAG   13320
AGCCTCCTCT CTGGGCACAG GGTGGAAACA GAACAGAGCC CACACATTTT
CCACGCATGC   13380
GGCGGGTTTC TCCACATCAC CCCCGTTTCT CGTCTTTATT TTCACACACA
CACTTACACT   13440
GTCATGCCTA TCAGGTGGAA TCATGTGTCC CTCCATGGCG GGAGGGCTCA
GTTACTTTAT   13500
CTTCTGAGTA GAAAGGCCAC ACTCTGCCTG GGGCTGGGCT GGGGGCAGGA
GTGTCTGGAT   13560
GCCAAGGACA TGGTAGGCTG TCGGGTGCAG CGTGATCGGG GAGGCAGAAG
CGCTGTCACT   13620
TGTTGTCTCT GATCAGGAAG ACCTGGTTCC TGCCAGCCAG TGTCTTTCTT
AGGAAACAGG   13680
TCCTGTTCTG AGTACTGGTG ACAAAGTCCC CATTTGCAGA GTTCTTTGGA
GTTCACACAG   13740
CATTTTCCTA CTGTGTCCCT CACTTGCTGT TCGTGTGACC CTGTGAGATG
GGAAGGGGCG   13800
GGTGTCGTTA TTCCTATTCG TAGCTGAGAG AGGCTGGAAC TTGAACAGGG
TATTACCTTT   13860
GTGTAGGCAC ATCCTAGGAT TTAAATCCCT TTGTCCTGAA AAAACATTTG
TAATCCACAT   13920
ACATTTTTCT ACAGAAACAA TGTTACTTGA AGATTCAGTT CCCCTTGCAC
CTGCGAGCAG   13980
TGCCTAGAAC CCTCGTTTTC TGGATTTTCT CAGCACTCCT TCAGCAGTCC
TACTGTGTTG   14040
CTTTAGCTTG CACTCGGGCC GCTGCTGATT TCCATGCTGG GGCATCGCAG
CCCAGCTGGT   14100
GTGAGCTCTG CAGGGACCAG ACCCACCTCC ATCCCGCAGC CCACACACCC
AGCCCTGTTA   14160
GCTCTCCACC CAGTGCAGGC CAGTTTGCAA CCAGAACTTA CCAGAACATA
CCTGGGAAAC   14220
TGCGAAAGTT TAAACTGTT TTATTTTCTT GCTCCAGTCC TGTTACTAAG
GGCTGCTCCC   14280
CTGGGTGGGG GACAGGGCTC TGTCTGAGCA GGCTTAGAGG GACATAGGCT
TTGGAGCAGT   14340
CCAGCAGGCT GGCAGGAGGA AGACAGGGCC TTAGCCAGGA GAGGGGCGGG
GAGCAAGAGG   14400
```

```
GGCTTGTCTG GTGGAACTAT CTTAGAGAAG TGATACCTGT TGATTTCTAT
ATGGTGCTCC    14460
CTTCCCCAGT TCCACCTTTA TTTCAAATCA TTTGAAAACC TTGATAATGA
GCCAGATTGC    14520
TGCTTTACTA ATAGGAACTT CATGCAGGAG AGATAAGATA GAGAGGTGAC
ATTATTTGGG    14580
ACCAAATTCT AGAAATCTTT GCTTTAGATT TTGGGGAAGC CATAATTGGG
AACACTTCAT    14640
AAGCTTTTGG GAGAGTGTAC TTGGTGGGGG TTGTGGGGGG CTTAACTGTC
AGCGGCTATT    14700
CCGTTGTTAA ATTATTGACG TGCAGGATAG GGACTGCGGA GGCTGGCAGT
GACATATGAG    14760
GCCCTGTCAG GATATCTTTC AATAATTAAG AAACAAGTAG TTGAAATTCC
ATTTTAGTTC    14820
CAGAAGCTGT GAAGCAGTTC CATAAATGGA TCAGTTAGAG GAGTAAGTGT
GTACCCCATC    14880
CCTCAGCGGA AGTTTCCATC AGGCATCTGT GGGAGTGGGG GCCGGGGCAG
GGGTGCAGGT    14940
GCTCCCAGAG ACAACATGTC CAGGTTTAGC AACTCTGATA ACTATAGGAC
CCCAGAAGTA    15000
AAAGCACTCA GGCCCTAACT TCAGGAAGAA ATGACAAAAA GCTTTGTCAT
CAGAATGGAA    15060
GTAGAAAATC CTGTAAATTA CTGAGTTTTT TTTTTTTTTT TTAATGCACA
GGTCAACCTT    15120
GAACTTGGGT ATGCCATTTC ATGTCACTTG TTAATTGCAG GGTGGGAACC
CAGTAGAAAT    15180
AATAGAGGGT GATGCTTCCC ACCTTTTCAT TCCAGAAGGC CATGAGCAGA
CGCTTCTTAG    15240
CTCGAGTCCT GACCCTTGTC TTGTCAGTGA ACAGAACTGT CCGTGCTCTG
AACGGCTCAG    15300
CCTGGGGTGG CGGCAGAAGG CGTTGCAGGT CTGTTCTCAG TGGCAGCAGG
CACTCCATGC    15360
CTGGCCTTCT GACCCCGGTC CTAGCGGGAC GCACCACACC AGGCTGCCAC
CTGTTCAGGT    15420
CAGCTTTGGC AGAACAACCC TCAGGTCTAA GGACATCGTT TTCTTTAAGG
AAAATCCTGT    15480
GTCACTAAAA ATGAGGGATT TTTAAGCAAC CTGGAGAGTT CAGAACTAGA
ACTAGAGTTC    15540
AGAACTAGAT CAGAACCTTC ATTTTCCTGA CTCCAAATTT TCTCAGGCCC
CAGTAGTTCC    15600
TGTCACATCT CCATAGCAGA TGAAGATCAG TTGAGGGTAG AATAACACTA
TCACTGCTAA    15660
ATTATTTAGG CAGCAATTAG AATTTGTTCA GCATTATTTA GGGTTTTTAA
ACAAACCTAT    15720
CTGAGTAACC TTATAATACT ACCGTCTAAA ATAGATATTG TATCAGTCTT
ATATCAGATG    15780
AGGTGAAAGT CACATCTATA AAACGCTGAA CTCTTAAATC TAACCAGGGA
TGGAATATAT    15840
CCTGTTAATT TGTCAAACTT CTAGAGAACC GCCTACATGA GACAGTAAGG
ATTAATCAAG    15900
CCCTACTAAG AGAGAATTTG AAAAATACAG TTTTCTAATT ATACAGTCTC
TTCTCCATGG    15960
CCAAGGTTA ATGCAGTTCT GAATTCTGAC AGTTAGTAAT AGAAAAGAAA
AAAAAAAAAA    16020
CCAAAGCATA TGAATTGTCT TATAATTACC TGAAACAGAA AGTCTCTTCT
GGCAATCAAG    16080
GCCTTCTAAG CATTAATCTG ATATTTTCAG CATTTGATTC TTTTCCTTTT
AAACAAGGTT    16140
GGGAATAACT GGAGGGTTGT GTGTCACTCT TTGTGCTTAT CAAATATATG
TACTGTTTGC    16200
AGATTTATTT TGCTTATTGC TTAGCTGTAG ATGTGTAATT CTAGGTTGAA
CATTTTATCT    16260
TTTTTTCTTT TTTTTTTTAC AATTTAGACT AACTTATGAA TACTTCCTAG
ACACTGTATC    16320
TTTGAAATAC TTGATCCTTA TTCCTACTAC GAATATAAAA ACTAACAATT
ACTTCTTGGT    16380
TAGTTTTGGT TAGTTGTAGC TCTTGCTGCA GTTCATCCAG GCAACACAAC
AAAAATGTGC    16440
ACTCTAGGGA AAGGTAAATT TATTCCTTCA TTTATTGCTG TCAAATATCT
GTGGAATGTT    16500
TATTGTACAG GTTGAGCATG CCAAATCCAA AAATCAAAAT CTGAAACTTT
TTTTTTTTTC    16560
TGAGATGGGG TCTTGCTCTG TTGCCCAGAC TGGAGTACAG TGGTGCAAAC
ACAGCTCACT    16620
GCAGCCTTGA CCTCCTGGGC TCAAGCAGTC CTCCCACCTC AGCCTCCCAA
GTAGCTAGGA    16680
CTACAGGTGC ACGCCACCAT ACCTGGCTAA GTTTTTTTAT TTTCAGTAGA
GATGAGCTGT    16740
CACTATGTTG CCTAAGCTGT TCTTGAACTC TTGAGCTCAA ACGATCTCCC
CCACTTGGCC    16800
```

```
TCCCAAAGTG CTGGGATTAC AGGCATGAAC TACTGCACCT GGCCCAAAAT
CTGAAACCTT    16860
TTGCACACCA GCATGACACT TGAAGGAAAT GCTCATGGAG CACTCTGGAT
TTCAAATGTT    16920
TGGATTTGGG ATGCTCACCT GGTAAGTATA ATGCAAACAT TTTAAAATCT
GAAATCTGAA    16980
ACAATTCTGC TCCTAAGCAT TTTGGATAAG AGATATTTAA CCCATAGAGG
AAAGGTACAT    17040
GGAAGCCCCA GACCACCCAA AAGAAAAGGC CTGGGGAGAA GATGGGCAGT
TATGGCTAGA    17100
CACCAGATTT CAGGTTTTAC AGATGGATCT GGCATCTGAG ATCTATGAAC
AGATGGATTC    17160
TTAAGGTCAG TGACTGGCCG GGCGCGGTGG CTCATGCCTG TAATCCCAGC
ACTTTTGGAG    17220
GCCGAGGCAG GTGGATCACC TGAGGTCAGG AGTTCCAGAC CAGCCTGGCC
AACATAGCGA    17280
AACCCTGTTT CTACTAAAAA TACAAGAATT AGCTGGGCAT GGTGACGGGT
GCCTGTAATC    17340
CCAGCTACTC GGGAGGCTGA GGCAGGAGAA TCATCGCTTG AAACTGGTAG
GCAGAGGTTG    17400
CAGTGAGCCG AGATCACGTC ATTGCACTCC AGCCTGGACA ACAAGAGCAA
AACTCCATCT    17460
AAAAAAAAAA GAAAAAGAAA AAAAAGGGCA GTGACTATGG GAGAAAAATC
AAAGACCAAT    17520
ATTTTACCTT GGGAAGTGCC CACAAAGGCA GGAAAAATAA AAGGACCTAC
AGAAAAGTAA    17580
AGCAGAAAGA GAACACAAGT GTATGGTGGT CCTGAGAGGT TTTAGAATAG
AGAGGAGTCC    17640
AAAGAGAGCA GGTGAATCAA AAGGTTCCAG GCCAGAAGAG ACCTTGGGTT
TTCATGATGA    17700
CGAGACCCTC CTGTGGCCTG TGGAGCTGGC TCTCATCAGG TCATCAGAGC
CAACTGTGCG    17760
CATTGCTTCC CAAGTACACG TCATGTTGGG AGTGGGAGAT TGGCTGTGTG
AAAAAATGTC    17820
TACACCACGG AAATTGGCAG ATATATGGTG ACCCAGCAAA CACAGTTGAC
ACCTGAAACA    17880
TAATTTTTAG GAATAGTATT TAACCTTGTA TGCGGGATCC ATTCTGACCT
CTATCCTTCC    17940
CTTCTTACCT ATTTCATTAA AACAGAAGAA AAAGCTGGTG TAACTCATTG
AACTGATTTC    18000
ATGACCTGCA GTTTGAAAAA CATTATTTTA GAGAAAACTG GGGATTATGT
ATGCCTTACA    18060
AAGTCAGAAG ACAATTATTT TAAAAATAAA TTATAGTAAC AATTGTAGAT
AGGATGATTT    18120
CATCTTGAAA GGAGGAAAAA AAGAATCCTA AAAGGCTGAC AAGATGACCT
CTCTAGACTA    18180
AGGACTAAGT ATGCATGCTT ACAGGAGAAG AAAAACGAGC AGAGAGAAGC
GGGAGCCCTC    18240
AGAGATGGAG GGAGGAAGGG GCTGGGAGCA CGGCCTTGTG TTTGCCTGGG
GAGAGGAGGC    18300
CGTGTTTTGA TAGTGAAAGC TTGTTTTAGA GAAAGTCACC TGTTCTGGAG
GATTGAGGAA    18360
TGAAACTGGA AACCTTAGGA AAAAAGCAAA GACATCGGAT GTACTTGGTA
TTTTTTAAAT    18420
TGCTTTTATT TAGTTAGCTG GAAATGCACT TTCTCAGATC CACTGTCACT
CCTGCAAATT    18480
ACAAGAGCGC TCAGCCACCC TGTCGAAGGT CATCCGGCTT CCAAGCAGCA
AATTGGACCT    18540
TGAGCCCTCG TGCTGCCCTT GTTGCAAAGC TCTTTGTCCA CACTCGCTGG
CAGAGGTGGA    18600
GAGTACAGAG GGGAGGATGC TTGGCCTGTG GTGGTCTGGC CAGCCAGGGC
AGGCATGAGC    18660
TCGTCACAGG CCAGGCAGTC ATCGAGTGCT CTTTGTGGCC TGAAGTGGAT
TTGGCAGGTG    18720
CCTGTTATTT GATCAGTGTC GATGGCCAGT CGACACAAGT AAATGAATCC
CCAAACTTTA    18780
CTCTGACCCA CCTGCTTTAA ACAAATTGGA GGAAGTCATC AAGTTAGTTT
CCCTAGTTTC    18840
CTCTCTGAGG ACAGTCTGGG GGCTGAGGCT GGCTGAGTCC TGTCTCCTCA
GGACAGGCCC    18900
AAAAGGAGGT ACAGGGCGGC CTGGGGGACA GCAAGGTTCA GAGTTTCAGG
GCTATGGAGA    18960
TCCTGGAGCT GATAGACGAG TGTCAGCCAC AAAGGTGAAG CTGGATTTCA
GGACCACAAC    19020
AGGCGGCACG TGGGAGTTAC GAAGGGGGCA GGGCTGGGTT GCGGCCTCAG
GTGCTCCTCT    19080
GGGTTGGGGC TTCTCTCCTC AGCCCCGCAG GTGCGTCGGG CAAGCCTGTG
ATCATAAGAC    19140
AGGGCTGAGG GGGTCTGGGG AAGGGTACGG GAACCAGCAA GAGAGACCAG
GGTGGGGCTG    19200
```

```
ATCTTACACC CTCCACCGAA CACTTGAGTT TCCTGCTTGT CAGTGTCACT
TTTGCGTATG   19260
TGGGATTTTG GATTGTTCCT TTTAGAGTCT CATGTGTACC CGACACACTA
CTGTTCATAT   19320
TGCCCAGTAG CTTTATATAT ATGTAAATAT ATATATATAT ATATGGGTGC
TAAATATTTA   19380
TCAAATGAAT AAAGGAGGAA ATGCAGATTC CAGTTATTCA TGGTGATGTT
GGGAAGTACT   19440
GAAAGTCCTC TTAAATTCAA ATATCAGAAA TATGCTCTCC CATCTAATAA
ATACTTTTTG   19500
ATGGTGCTGG TATTAATATT CAGATATGAT ATATATTTAA TATTTATTTT
TAATATTAAT   19560
ATTCAGATAT ATATATTTTT TAACAAGAAG CTTTACATTC TTCATCTTGT
GATTTTTTGG   19620
TTAAAAGAAA GGAAGTCTGT TTACTAAATC GCTGTTGCAT GTAGTTTCTA
TAAATCGCCC   19680
TCTGTACACA GGGATGTCAG ATGCTGCCCA AGAGAATCTG TTTCATATGG
TAATTTTCAC   19740
TAATGAATCC AGACCTATAC TGTTAAATTT TGCCCCAAAC TGCCTGGGAT
GAAGTAGAGG   19800
AAGCTCATGG CAGTGAGCGT GACAGTTCTT AGAGGACGCT ATCATAGTGT
TTCATAACAG   19860
ATGCAGAGGC TCTGCAGTTC TGAATATTAA TACCAGCACC ATCCAAAAGT
ATTTATTAGA   19920
TGGGAGAGCA TATTTCTGAT ATTTGAATTT AAGAGGACTT CCAGTACTTC
CGAACGTCAC   19980
CATCAATAAT TGGAATCTGC ATTTCCTCCT TTATTCATTC GATAAATATT
TAACACCCAT   20040
TATGTTCATG GCATCACATT AGACTCTGGG GGAGTTACAA AGAACCTAGG
CTGCTCTGCC   20100
TTCAAGGGGG AAATAAAAGA AACAATTACA TGTAATTGTT TTTAACACCA
AGCAGCGTGA   20160
AACCCAGCTC TGGAGCAGCC TGGTCACAAG GGGGAGAAGA GGTCACGGGA
GCCCCTCCAA   20220
GGCCAGCGCA CATGTGGCCA TACCTTGTGC CTTCCCAAGC CCGGGCCCTC
GCACCCTTCT   20280
CTTGTCTTTC CTTGTCCTCC CATGCCGTCA GGGTTTATGA GACCTGCAAG
TCTCGGGGCA   20340
TGGCTCTGGT CACTCTGGGC AGCGAAGATG ATTCTCTGAT GGGCTGTGGT
CAGTGAAGCA   20400
CAGCTTGTTT GCCTCTTTTG ATTTTCCTGC AATGCCAGGA GAGATTGCTC
AGTTTTAGGC   20460
AGGACTGAGA TCTCCTAAAA CATGGAATTT GTAGACAAAA ATGAATACTT
CCTAACATTT   20520
CCTGAGAGAG CTTTTGGTCA GCCTTATGCC TGCAACATTG CATTGCTGCT
GGGGGACCAG   20580
GCACACAGAG GTAGCTGCAG CTGCACCCGA ACACGAGAGG GTGGCTGAGG
AGAGTGGCCA   20640
GGCCTTCATC TCTCTGACCC AGAGTACGTG CTCAGTAAAT GATCATCGAT
GAAGCAAGTG   20700
AGTCGGGACT GAAATGTATG AGCGCCATAA GTTTAGGCCA CTGCTCATTT
AAGGCCTCAG   20760
AACTCCTGGA AGTGTTACGT GTAGAAGGTT GGCAGGCTGG AGAGGGTAGG
GGAGACCTTG   20820
AAGATTCCCA TATTTATATT CTAGGTGGCT TGTGTGATGT GGCCATGGCC
GGATGTCATT   20880
CATTAACTCG TTTGACAAAT ATTTATTTTA GCACTTGTGT GCATAGCATG
TGCTGGGAAT   20940
ACCAGGGGAG CCAGAAGGCA GTGCTTCCGG AACTTGTCTG CACGTTGGAA
TCACCCGGGG   21000
AATTGCTTAC AAATTCAAGC CCAAGCCACA GCCCAGGCCA TCACACTCTG
CAGGCACAGG   21060
GCACAGATCT CTGTATTTTG GAAGCGCCTA AGGGTGTTCT GATATCAGAG
AGGTTTGCAA   21120
GTCACGGCTG TTAGGATTTA TAATAGAGTT TTAGATAACA CACCCAGGAA
AATTCAGTAA   21180
CGATACAAGA CGGCCATCCA GAAACCTCCT GGGCAGGATG AGGGAGTCAA
ACCCAGGTGT   21240
GTGCTGTGGG CACCACTCAT TCCCCCTCAA GGAGGATGTC GCCTGTGGAT
TAGGGAGCGG   21300
GAGCATCTAG GCAAACTGGA CCTCTGGGGT GTGTGTTGCT TTGCCAGGTT
CGAGAGAGGG   21360
AGGAAGGGGA TCCCCTTGAC TCTGAACTCA GGCAGGTCCG GATGTGACCC
GGGATCATGG   21420
GTGGAATGCA CTGGTCTATC AAGAGCTCAA CTAGTCATTG CCATTTAAGT
GGATGAATGT   21480
TTTTCTTATA AAAGACAGAC TGGGCTGGGC ATGGTGGCCC ACACCTGTAA
TCCCACAGCT   21540
TTGGGAGGCC AAGATGGGAA GATCACTTAC GGCCAGGATT TCAAGACCAG
CCTGGGCAAC   21600
```

-continued

```
ATAGTGAGAC TCCATCTCTA CAAAAGATAC AAAAAATTAG CTGGGCTTGG
TGGCACGTCT  21660
GTACTCCCAG CTACTTGGAA GGCTGAGTTG GGAGGATCAC TTGAGCCCAG
GAGCTCGAGG  21720
CTGCAGTGAG ATATGATCAT GCCGCTGCAC TCTGGGCAAC AGAACGAGAC
CCAGTCTGGC  21780
TGCTGGCGTT TTTCCTTGTG CGTATGTGGG CTGAGCACGA TGTGGTAAAG
CAGATCCCTC  21840
AGGATGGACA CGCTCAGCTT CGTCACTTGT TGATTCTCTT GCTCTTAAAA
TCCCCTAGCC  21900
CTCTTAACAG CCACGGTGAA CTTCCCCATG TGTGCGTGTC AGCACACCAA
TGAGCCAGCT  21960
CAGGTGGCAC TTTCATGCCC CAGGGTCTTG TCGAGCCGTG AAGCGGACGT
GCGCTTAGGG  22020
TGGGGAAGGC ACTTGACCTC GGCCGTCCTG GCCGCTCTAG GTGCCTTCAG
GCCTCACTGC  22080
TCATCAGCAA CCAGCCAGAC CACGTGGGCC TCATTTGGTA TTCTTAGGAC
TTGCCATTTC  22140
TAATCAATGT TTTTACTTGA GTCTGTTATA TGTTATTTCA GAGGGGGGAA
TGGAATGTGT  22200
TAACACTTAG TAAATTCTTC ATGAGCTGCA ACCAAAGTTT TTCTTTCTTT
CCCTTTCAAC  22260
CCACAGTGTG CCATGCGGAG CTGAATGCCA TCATGAACAA AAATTCGACC
GATGTGAAAG  22320
GCTGTAGTAT GTATGTTGCC TTGTTCCCTT GTAATGAATG CGCTAAGCTC
ATCATCCAGG  22380
CAGGTAGGAA CCGGGTCTTT CCATTTGTCA CATTTGCATT GCTGCCTGCT
CGTCAGTAGC  22440
TCATTGCTGA TGTGTTTGAT CTTAAATTGC TATTGTTTAG ATCTAAATTA
ATTGCACTAT  22500
CAGCTTTGCA AGATATTTCC CGTGTTTTGT TTTTGAATGG TGCCAGGTAT
TCTAAGACTA  22560
ATTGCATCCT CTGTGATTCT TAGCATGTTT TTAATTTAGT TTGCAACTTC
TTAAACTGCA  22620
AGCTGCCAAA AAACAACACA GGCATTGCAT ATAATTACTG TCAATTTACT
GTTCTCTGAC  22680
ATATGTGCAT AGATTTGGGG GAGGGAAGAA ATGAACTTCT GTCAGAAACA
AGGTCAGCTG  22740
GGAGTCTGTA TATGAAATTT TAATTTGTAT CTAATACATG GTAGATATTT
GAGGATCTCA  22800
ACATACCTTG GCATATAAAT GTCATAAGAC CCAAATGGCA CTACCTTCAG
GTTTTCTTAT  22860
TTTACGGTTC CCATAAATCT ACACCATTGT ATTCTGAATA TTTCGCCTTT
TTCAAACTGT  22920
CACATCTAAG ATTCAGCTAC ACTTTGTCTC CATAAAACTC TCGGCTGGAG
ATTTAAACAC  22980
TTACCATGTT TAGCCAAATG TGTGGTTTGA AGGGGCCGTT TATCACCAGT
CCTGTGGATC  23040
TCAGAGCAGA AGCGGCCTGC TGGTACTGAG GAGTCGCGTG GGCTCCCTCG
TGTCGCCGTC  23100
ACCGTTCCTG GGAAGCTCTC CTCGCGGTGC CCAGGTGTGG AGGCGGTGGC
AGCCTGTGGG  23160
CCGAGCAGTC CGGGCCCCAC ACTGCAGCCT CCTCTGCCTT CAGAGGCTGA
TGGAGCAGCG  23220
GCCTTCAGTG CGGGGCCCTT GGGATTCCTG GCTGCCGAGT TAGCGCTGCC
TGCTGAGATC  23280
AGGACAAGAA AACAGATCTG CCCTCTGTAG AGCTGGTTTG AAGTGGTCTG
CAAAGCCATG  23340
CTGGGAAGCA CAGTGGTGCC CACCTCTGAA TTTGCCAGCA GCCCCCACTC
CCTCCATTAG  23400
TCCTCCCACT AGTAAGAGAA GCTACCTTGT GATACTGCCT TGATTACCTG
TAGTAAGGGA  23460
AATTGGTTAA TCGGATCAAG GCTTGACTAC TTGACATGTT TTCCCTTTGC
ATTTGTTTAA  23520
AAAAAAAATC CATAAAGACT GGAGGGAAGA TTAGATAGAA TCCACCCTCT
GCTGTATTAG  23580
AAAGCAGCAG ATATGTATTT CAGTGACTGG ACACTGTCTG CAAGCACACT
CAGAAAAGGT  23640
CATTAATCAT AGACGCTGAA AGTGCTCCAG CTCGTTCCGC CTGTCTTTTG
CAGCATCTGT  23700
AGGTGCGTAC ACTAAGGGAG CTCCCATTGT TACCTTACAG GTATAAAAGA
AGTGATTTTC  23760
ATGTCTGATA AATACCATGA TAGTGACGAG GCAACTGCTG CGAGGCTCCT
GTTTAATATG  23820
GCCGGGGTGA CATTCCGGTA AGTGGGGAGA ATGCGGGCGG GGGGACGGGG
TAGGGTGAAG  23880
GCTGATGAAG AGATGTATTT GACCTTGTCT CCTCCTTGTG ATGCCTGACT
TCCACACTTG  23940
GAGGTGTCTT TAGAAATGCA AGGGCATAAG AATTTAAAGA CTATTATAGG
GGTAGATATT  24000
```

```
TAAGAGCAGT GACAGGAAAA TCTGAAGACC ATTTGTTTAA TGATTGTACT
TTAATTTCAG  24060
TAACTTTCCG GGGTAATTAG ACTAATTATT CAAGTACTGA GAAGTTTAAA
CATTCACAAG  24120
TTTTATAATA GGAACGCCAA ACCTTGGTGA ATTTTGCAAA TGTAACAACT
TTGGCATAGA  24180
AAATTTAGGA TGAAAGTAGC CTGCCAGATT GAAACATTGG GGATTCTCTC
TTTTTTTTTT  24240
TGAGACGGAG TCTCGCTCTG TCACCAGGCT AGAGTGCAGT GGTGCGATCC
TGGCTCACTG  24300
CAACCTCCGC TTCTCAGGTT CAAGCGGTTC TCCTGCCTCA GCCTCCCCTG
CCACACCCAG  24360
CTAATTTTTT TGTACTTTCA GTAGAGACAG GGTTTCACCA TGTTGGCCAG
GATGACCTCA  24420
TGAGCTGCCT GCCTCAGCCT CCCAAAGTGC TGGGATTACA GGTGTGAGCC
ACCTGGGGAT  24480
TCTTTTTACA GCAACATTTT GCATTGAGAT TTGAAGTCTT ACAGATTTTT
ATGATTATCT  24540
TTGCTAAGAA ATGGTTGTGA GCTATATTTT ACTTGCAAGT AAGTTCAACT
ACCTTTGATT  24600
CATGGCAGAA AATTCCTTTG GGACTGTAAA GTTTTCCAGC GCTTCATGGT
GTTGGCGTTC  24690
AGCAGCAGTG GGACCATGGT CATAGGTGAC GTGCCCTGGC CCCTTGTGCT
GGTCATTAGG  24720
GATACAGCTC AGTGTATCTC ATGAACTCAA CCGTGGTGCC TTCTGAGACT
TTAATTCAAA  24780
TTATTTGTAT ACTCTCTTGT TCAGTGATTC TTAAAAGAAT TTGTTTTGTT
CCCAAATGTT  24840
TTCTTTTTAA TTGTTGTAGA AGAAATGAGG AACGAGTGAA AAGTTAATGA
GCAAAAAAAA  24900
AAAAAAAAAA AGTTGGTTTA TGTTTGCATT TTTAGAACGT AATTTGAAAA
ATTACTCCTC  24960
ACTAAAGGTA GTCGTTTTTT GCTATATATA AGCGGCAAAA GAAAATTTAC
TATTTTTTTG  25020
CATTAGAGAG ACTCCAAGTT GGCTGCAGAA ATTTTTCTAG AAAATAAGAT
AAATCTGATG  25080
GGAAAACTAG TAATCGGATA TCATGTTGTG CAGCTGACTT GTTAGAAATC
CTTTGACTCC  25140
CCCAATAATT CGTGAACTCA GAGAGCTGAA AACATACAAA CCACACCACC
CCATGCATCT  25200
TTTTTTGTCT TAGTCTTTTC TGCTCTGTGT TTCTCTTGGT ATGGTGCACT
ATAATTGGCT  25260
CCTATAGAGA GAAAATAGCA AGTGAATCCC AGGACATATT TTTCTCTGCA
CAGAAATATG  25320
AGTTAAGCCA AAGTAAACAA ATTGCTTTCA CTACTCACCA GATAATAATT
GTATTTTGTT  25380
TTTATTTTTA GGAAATTCAT ACCGAAGTGC AGCAAGATTG TCATTGACTT
TGATTCAATT  25440
AACAGCAGAC CGAGTCAAAA GCTTCAGTGA GTTACATCTC ATTCAATCTC
CAGAAGATTG  25500
GGATTATCGT CTTCTAAGAG GTTGCTAATG CCTTTCATCT TGAAGTTACA
CATAACTTCT  25560
TACTAGCCAG TATGGCAAAA GTAGGCATCT AAAGAATATA AAGCCTCAAA
TCTTCCTTAC  25620
TGTCTCTCTT GTCACATGGA ATCTACATGT GTTTGAACTA TTGCTTTAGG
ATTTAAAATA  25680
GGGGAGCCTG TGGTGGCCTG GTGCACAGGG CTAGAACGAG AGTGCCTCCC
CTTCTTGTGT  25740
CCTGGCTGGC TGGGATGCTG GTGGCTCTTC AGAGGAGCAT CAGCTGTCTG
TCATCTGCTG  25800
CGATCCGGCA GCCTCTCTTC ACTGCTACAT GTGCTGGAAG GACAAATAAA
TAATTGTGGT  25860
TGTGTTCTTA ATGGGGACGA GCAGACACAC TGATCTGAAC ATCTGGCCCA
AGTGAAGCAT  25920
GGCATATAGT GCCCTTGGAA GAAAATTAGG CCTCAAATGA CAGTAGCATT
GAAGTGTTTG  25980
CTGCAGAGTT GAGGGAAACC CCCAGCCACC CTCCCGGAAT CCGAGATAGG
GTGGCACATC  26040
TGTCCTGACA GACGAGGAGT GTAACTGAAC CAGGAATATT TCCTCCATTC
CTGCTCTCCC  26100
ACTGCACACA GGGTGGTGGC ACATTATCCC TCTGGGGGGT GGGGACGCCT
GTTGTTTTGG  26160
CTCAATTTGG GTTTGTTGGT CACATGGAGC TCTTCCATTT CGTTTAGCTG
AATAATGAGT  26220
TGTTCCTAGA GGAGACAGCC TGTCTCTCCT TGTTGCCCCC AAAGCCCATG
CCCTGCCGTG  26280
GTGGCAGCTG GGGCTGTGGA TGGGAGGGGT CCCCAACATG GATGTGTTGC
CCCTCCTCCG  26340
CATGCCAACG CAGTTCATGT ACAAGGCCCC TCTGCAACTG GAGAGAAAAT
TAATTCCTAT  26400
```

```
CCCGTGAGTG GATTGTGAGA AATTCCACCC ACGTGGAGAC AGCTTACTGC
AGCACTGTTG   26460
GTGTTCGGAG CTCTTCTGTG CCCTGGCTCC ATGCTTTCAC CTACACAAGC
ATCACCTTCC   26520
TAATCACCGC GGGGCGGGGA GCGTGTGGCT CTGCCCCTTC TCTTTAATCT
CATTTAATTT   26580
TTATTAAACA TGCTCAGTAC CTGTGTTGAG AAAAGGCTTT CTTTATCCTA
AAGATTATTA   26640
CCTTTTTAAA GTGCTCTTAT ATTTTCATGA GTTTTTATTT TGTCTCTGAG
ATTTTGTATT   26700
CCACATTCTA GGGTATTCTG TAATTTGGCT CCTTACCAAT ATTATTAAAA
TCTTATTAAA   26760
ATCT         26764
```

As used herein, a nucleotide sequence corresponding to a particular nucleotide sequence is one which is substantially the same nucleotide sequence, or derivatives thereof (such as deletion and hybrid variants thereof). Nucleotide additions, deletions, and/or substitutions, such as those which do not affect the translation of the DNA molecule, are within the scope of a nucleotide sequence corresponding to a particular nucleotide sequence. Such additions, deletions, and/or substitutions can be, for example, point mutations made according to methods known to those skilled in the art. Similarly, an amino acid sequence corresponding to a particular amino acid sequence is one which is substantially the same amino acid sequence or derivatives thereof. Amino acid additions, deletions, and/or substitutions which do not negate the ability of the human deoxycytidylate deaminase to perform its function (i.e. deamination) are within the scope of an amino acid sequence corresponding to a particular amino acid sequence. Such additions, deletions, and/or substitutions can be, for example, the result of point mutations in the DNA encoding the amino acid sequence, such point mutations made according to methods known to those skilled in the art. The function of deamination can be assayed for according to the method disclosed by Maley (Maley, Methods Enzymol 12A: 170–182 [1967]), which discloses a spectrophotometric assay for dCMP deaminase activity.

Referring to FIG. 1, the first 1317 base pairs (nucleotides 1–1317 of the sense strand) of the DNA molecule represent the 5' untranslated region of the gene, including the promoter, and have a nucleotide sequence corresponding to SEQ ID NO:2:

```
GAGCTCCAGT TCTCTCTGTT TCTACAGCTG GGCCTCAGTC CTCACAGGGC
TCTAGTGGGC   60
GTTCAGCACA CCAGGAGAAG GCGCCCAGGG GATTAACAGG ACCCTTCCCT
CTCCTGCTCT   120
TCCCTCGCCC CCCATGGCTC CCCCTCCCTC CTATTTAGTA GGTACTTCTC
CAGCACCCCA   180
CAGCGATGAT GGATGCTGGC CCTAAAGCCA GGTGGGAAAC CAGGCTGATT
CAGCACCTGT   240
CTTTTCCTGT TAGGGGGGTT GCCAGGCCTC TCAGATGTGG GGCAGCGTAA
TCAGTGGGTG   300
ACCGTGGTTC CCAGCACCCA CTCTCCACTG CATCCTTGTC TTAGGCACTG
CCGCCCTGCA   360
CTGTAGCAGA TGCCTAAATA AAGTGTGGAG CCTGAAGCAG AAGTTTTGGG
AGATGCTTGC   420
CTTCCTTTAG ACCACATTCC TCGCCTTTCT CAAGATTTCT CCGTGGTACC
CACCCCGTTT   480
TTGTGTTGTC TTCCTTCCTT GCCCTTGTTT CATTCCTTTT GAAAGCGACC
ACTCCCCTGA   540
AGTCCTAGGA CCCCCTTCGT GGGCTCTCCC TGCCGTAGAC AGTCTCTGCT
TGCCCCTGGT   600
AAACTACGTT CCAAAAACCT TGCTTTAGGA GTAGCACTTG ACGTTTTTCA
TAGTTTCTTC   660
TCATGTAATT CATTACTCGG AGTTGATAAC TTCTGTCCCA TCTGGATTAT
TGAGGAGAAA   720
GGGAAGGGAA AAATTATCTG GTTAATATCA GAGTTGGGAA GGCTTCAGAT
GTTTTCTTTG   780
AATCCGTCTG GCATGGATGA TAATCCTGTG TGGTTTAGGT TAAGTTACCT
AAGTTCTCTG   840
AGTCTGTGTA AGATGGGATG GCACTGTCTA CCTTAGCTAG GAGTAAGGCT
TGAGTGACAT   900
GATGTGTATA AACTTTAACA ATGTCTGGAA TCTATAGATG ATCAATAAAT
ATTTCTTTTT   960
TCCACCCTCC TCCTGTGCTG ACTCCGCTTT GTAAGGGAGA CAGGTAAAGG
ACACAACAAT   1020
TTGTAGGCTG GCATAAAAAA TCCTATGAGA GAAAGCAGTA AATAGATGAA
ATATTTGGGA   1080
ACGTGAAGCT ATAGGTTTCA AATTCAAACT TCTGAAATAG GAAATTTCTT
AAGTTTTTAC   1140
TTAAGACCAG AGACTGTTTA GGGCCCATGT GCTGTGATTT CTGATTGATA
AATGTAGCTG   1200
```

```
AAGTTGCCCA TGTTTAGAGA TTTAAAGGTT CAGTGTGGTT GGGTTGAACT
GGAAAACAGA   1260
CTTACTAAAA TGCTTCTCTC AACTTCTGTT TTGTCATGTT TTTCTTCTAG
ACCCAAC   1317
```

The 5' untranslated region is followed (5'→3') by exon 1 which comprises 108 base pairs (nucleotides 1318–1425 of the sense strand). Exon 1 has a nucleotide sequence corresponding to SEQ ID NO:3:

```
ATGAGTGAAG TTTCCTGCAA GAAACGGGAC GACTATTTGG AATGGCCAGA
GTATTTTATG   60
GCTGTGGCCT TCTTATCAGC ACAGAGAAGC AAAGATCCAA ATTCCCAG
108
```

Exon 1 is followed (5'→3') by intron 1 which comprises 402 base pairs (nucleotides 1426–1827 of the sense strand). Intron 1 has a nucleotide sequence corresponding to SEQ ID NO:4:

```
GTAAATGAAT TTCACGGGAG AATGCTTAGA TACTCACAGG CAAAGAGATT
ACTGCACATG   60
AGCAGAAAGG GGAGACTCAG TGGACGCCTG TCAACTTAAA AGTGCAGGGT
CGGTCTGCCT   120
TTTGTGCTGC GTTTCTACAA GCTTAGTTCT TCCTGTGAGA CAGAAAATTG
TCACATGCCA   180
TTGTTAACTG CCTCTTGTGC CCCTTCTGGG ACTGGGGGTG CACTTTCCTT
GGCTTGTGGG   240
TGCTGCCACA AAAAACCAGG CAAGGAGACC GACAGCTCTC AGCACCTGCA
GCAGCTATGC   300
GTCTGTTTTG AGTTCTGCAG TCCCCCTGGT TTTATTCCCT GCTTCCACAG
CGGCAGACCA   360
GCCAGTTGCA GGCACCAAGC CTTTGGGCAT GTTTCCTTCT AG   402  .
```

Intron 1 is followed (5'→3') by exon 2 which comprises 136 base pairs (nucleotides 1828–1963 of the sense strand). Exon 2 has a nucleotide sequence corresponding to SEQ ID NO:5:

```
GTCGGCGCCT GCATCGTGAA TTCAGAAAAC AAGATTGTCG GGATTGGGTA
CAATGGGATG   60
CCAAATGGGT GCAGTGATGA CGTGTTGCCT TGGAGAAGGA CAGCAGAGAA
TAAGCTGGAC   120
ACCAAATACC CGTACG   136   .
```

Exon 2 is followed (5'→3') by intron 2 which comprises 20,303 base pairs (nucleotides 1964–22266 of the sense strand). Intron 2 has a nucleotide sequence corresponding to SEQ ID NO:6:

```
GTAGGGCAAG TTTTATGTCC CATTCTGCTT AGTGACATAG CCTGGTGAGT
GCCTAATTAA   60
GAAAGTTGGT CAGAAGGCAT CATCTCCCTT TTGTCATCAA CAACTGGAAA
GAAAAGTATC   120
CTACTGAACT ACCCCAATTT CCTGGCCTTG TCTCTTAAGT TCCAAAGAGA
GCCACGGAGA   180
GAAGCATGGT AGTGGCCACA CAGGCTGGCC CTGAGATCCA GGGCTCTGCT
GCCTGTGCTG   240
AGCCTGGCAG GCTTCACTGG CAACCTGCTG GCCTGCACCA CACCAGTGCA
CTGATAGTCG   300
GCGTCTCTGC AGAGGGTCAC AGCCCCTTGC AGAGATAGCT GAGGGATGTG
CATGGTGTCT   360
CTGTGGGTTC CTTTTTTTAC TACTTGGAAG CAGGGTCGGC TAACCAGGGG
```

```
CTGGCTCGGG    420
CTTTGGTCTG ATGAGAAGCA GGCTTCATTC AGCCCATGTG CCTGATGAGA
ACATCTGGCT    480
CAAGCTCATT GCTGGCAAGC AGGAATCAAA CTGTGAACTA GACATCAGGA
GATGGAGGAT    540
CCAGTTGCTT CCTCCAGTTA CAGGGGATGC TGCAATTTCA CAGTAGGCTG
TGGTCAGACC    600
AAAAGCCAGA AGTGAGGCTG GGCACGATGG CTCACGCCTG TAATCCCAAC
ACTTTGGGAG    660
GTGGAGACGG GCAGATCACC TGAGGTCAGG AGTTCGAGAC CAGCCTAGCC
AACATGGTGA    720
AACCCCATCT CTACTAAAAA TACAAAAATT AGCTGTGCGT GGTGGCAGGT
GCCTGTAATC    780
TCAGCTACTC GGGAGGCTGA GGAAGGAGAA TCGCTTGAAC TCAGGAGGTG
GAGGTTGTAG    840
TGAGCCAAGA CTGCGCCACT GCACTCCAGC CTGGGTGACA GAGCAAGACT
CTGTCTCAAA    900
AAACAAAACA AAAACAAACA AACAAAAAAC AAAACAAAAA CAAAGAAAAG
AAAAAGCTAG    960
AAGTGTAGAA CTGTAAACCT TTGGCTTGAC TGTCTCTGGA TTTTCCCCTT
GAAATTAGGG    1020
AAGGCTGCTT CTTAGAGTTT GTTGCCTGTC TAAGCCCCAG GGAAAATTCC
TTCAGAGATT    1080
GCCTGGGAGG GTCCAGCCAT AGCTTTACTT TTCCTTGCAT TCCTTGGAGA
ATATGCAAGC    1140
AATGCTGGAA AAGAGGCAAA TCATGCTGGG TATGCAGGTT GCTGATTTTT
GTAAGGTTAG    1200
GCCCTGTATT TTATGTCTGA GAATGAACAG ACTGGCGCTG TTGGAAGTGA
AGGGAGAGTA    1260
AGGCCATCCA AATGGGAAAG ATTGTGTCTT CAGGCCAAGG CGTGATGTAC
GACCTTTCTT    1320
CTTTGTTGAC TCTCCTGGTA GGTTTTCTTC TGGGTTTTTC TCATGAAGAA
TCCAAGTCAA    1380
CATTTAGTCT AATTTATATA TTTTTACTAA TGTTCCTGGA CCTCAATCAT
GTTAAATAAG    1440
CCCCATAAAT TTCTTTCTAA ATTGCCTAGG GGCAACTTCT CCATGTTTGA
AAGAAAAAGT    1500
TAAGAGGTAC CTGGAGAGAG AGGAGGAACT GAGGACTGCA AAGCAGTCTG
GGTTTCCAGG    1560
ATGTGAAAAG TAGTTTAGGG ATGAAGGGGA CCGAATCCTC AGATCCTTGA
TTTAACCTCA    1620
CCCTCCCTCG TCGGAGTGGG AAGAGAGGAT GGAGTTGGGG GAGGGTAAGA
CTGTCTTCTC    1680
AGCACAGCTT CAGAGCCGGT GGTAGTGGAT GACTAATTAG AAAAATGCGC
GGACTCAGAA    1740
ACTGTCACCC TGATTTTGAT TCTATAAGCT TTTGATGGTA AGAAAGAAGG
GAAGTGATTA    1800
GTTGTTTTTA AGTCCATGCA AAGATAATTT TTCACAGTGC GGTTCAAAGT
CCCCTATAAA    1860
AATGGTGAAA GTGGAGGGTC GGATATGTTA AAGGTCTGCA TTGAACTGTG
TGACGGCCAC    1920
AGTCAGTATG TCACCGAGTC TGGGCAGTGA AATATTGGCC CTGGGGCTGG
ACTTTGATAT    1980
GGAGGAATTC TGGGGGGATG GCGGTCCGTC ATACTCAAGC TGGTGCAAAA
GATACCCGTG    2040
GTTGGACAGT GCGGAGGGGT CCTGGGTGAG CACTGAGTGG GCCTCCAATG
GGGCCTGTGC    2100
CTTCTTCAGT CACCCAGAGC CCCCAGCAGA TCTTTAAGCA GTGACCTGGA
AGCCAAGGGC    2160
CATGCAGTAC ATTTGCAGCA CCTGCCCCAC ACCCCAGACT TCCCAGCTCT
CCTGACTTCC    2220
CGTGTAGCTG ATTTTGTTGG TTATGAGACA CTGCCTTTTG TCCAAATTGA
GGAGAGTACC    2280
TTTCAGAGCC CCTTTCTAGA AGGAATTTTT TTAAAAACCT GCATAGGTAT
TTGTCCAACT    2340
TCACCGATTG TTTTTTATTG AATAGCTCCT GAGCTCCTGG GCACTGGTTG
TCTGTCTCTG    2400
CATTATTTTT TATTATCCAT ATGATACCTC TAGGTTTTCA AAGCTCTTTG
CTCTTACTTA    2460
TCAATTATTC ATTTATATGT AGCTGTGTTA GAATGTCGAC AGTTTTCTTT
CACGAGAGTA    2520
AGCTTGTAAT TTGATGTACC ATAAAAGTTG TAGAAGGTAT TAAATGGTTT
CTAAAAGGCA    2580
TTTAGTATTA CTGCCGCCAT AATACAGTAA AGATGGGCTT AAAGTCTAAA
TGACGATGAC    2640
TGTGTATAAA CTGTACACTT GTTGTCTTCT CAAGGTTTTT CAGGCCACAG
AGAAGTAAAT    2700
GTTTGGATTG CCTGGGATGT CACAGAAATG TTTGCTGATA ATTGACTCAA
ATGCAAAGTC    2760
TTTTTTTTTT TTTTGCTTT CGTTTTAAGA TTTTCAAAAT TAATTTAAAA
```

```
AATAAGGGGA    2820
TACTGCCTGG AGTTGGATAG CTCAACCCAT TCTTTCCTCA TCTACATTAA
TGGTGACTGA    2880
GCTGCTGTAG CAGGAAGGGT AAATTCATAG GTTAATCCCT GTAAAGGAGC
TTTAGAGATT    2940
ATCTCGAGTT CTGGACAATG ATTTTTAACT CTTTTGAATG TACAGGACCC
TCTTTTAAAT    3000
GCTGAAAAAC TTCCAGGACC CCTGCATAAT GCTAAATTCT TAGTATCTTT
TGAGTAAGAA    3060
ACTCCACAAT GACAAAAACT ACTTCGTATC AGTAACATTT TTTGTTAATC
TGAACTTTAT    3120
TAATTGGATA GCATTTATGT ATGTTTGGGA AAAGTTTATG TATGTCCTGG
ACATGGGATT    3180
TATCCAGTTG TGGATATGCT TGGACCCCTT GCAATACCTT AGTAGTGTCT
CAGGGTTCTA    3240
TGCCCACAGG ATCTAAGCCT CCTCCTTTCT TGTAAGTAAC TTCTATAATG
TCACACATGC    3300
AGGGTGACAT CTCCTAATTC CAAGGTCAGT GCTCTTCCTG CTACCTCCCT
GTGTCTCTCC    3360
TGTGGGGCAC ATGAATTCAG CTGTACTGAA ATGCCAATCA TTGTCTCATT
TTTTTTTGCA    3420
GTTGATCAGA CTGAGGCTCC GATAAAATAA TTACTCCTCA GAGATCAGGA
GCTCGGGGAG    3480
GGGTGGCCTG TGTCCGGCAT CATGCAGAAC AGCATGCGTG GCTCACTGTA
ACATTTCTTC    3540
AAAGGGGAGT GCAGTGGACT GAATGTGTCT CCCCCCAAAT TCACATGTTG
AAACCCTAAT    3600
TCCAATGTGC TGATATTTGG AGGTGGGGCC TGGGGGACGT AATTAGGCCA
TGAGGGTGGA    3660
GCTCTCCTGA ATGGGATTAG TGCCCTTCTA AAAGGGACCC CAGGGAGCTC
AGTTACTCTT    3720
TTTCCATGTG CAAGGATAGG CGGAGAAGAT GGCTATCTGC AACCCTGAAA
GGAGACCTTG    3780
CCAGAATCTA ACCATGCTGG TGTCCTGACT TCCAGCCTCC AGAACCATGA
GAAATAAATG    3840
TCCATTGTTT CTCAGCCACC CAGTCTATGG GACTTTGTTA TAGCAGCCCC
AAGGGACTGT    3900
GACAGGGAGC TTGAGAACTG TGTAAATTTG AGTTTACCAA ATAACATACA
GCTTAATACT    3960
GCTTTATTAA TTCCGTAAGT CGGAAGTCAT TAGTCCTGAT TGATGCCTTG
TGGGGAGGAG    4020
GGAAACACAC ACTACTTGTA ACATAATAGG AAGATGGAGC TTTTCCTGGG
CTGTGTCTCT    4080
AGAGAGTTAT TTTTAAAAGG GTGTTTTTGT TCTTCCAGTC TTGGGATCAA
AACTTCATAA    4140
AACTATTTTA TTATAATGTA GGTATTAATG TGGAAAATGA AAATTCCCTC
TGCTAAAGAA    4200
GCTTTTTATT CCATCCTTTT CCTGAAAAAT CCAAAAGATA ATATGATGTC
AGTAACATTA    4260
AGTGGCAGGA AGAAGGCAAT GTTATTATAC TAAGAATCTT TTCAGATGAA
TGACAATTAA    4320
AAAAGAGGAA GCAGCAGATT TATCTAATTT ACAAGATTAA AAAACTTGGG
AAGATTTTTA    4380
TTTTCATGAG GGGGTGGGTT GCTAAACCCG TGATGAAGTA TTCAGTTGAC
ATTTTTCATT    4440
CCTTTTTCTT TGTGGAATTC ATTATAGTGA AGCACATTTA ATCAAAATAC
CAATGTTATC    4500
AAATGAGGTA AAATACTCTT GGTGATTCAG ATATCACTCT TTCCTTGGGT
TTTCGTAACC    4560
GATTTTGATG ATATAGTTTA CAAATTAGAG AGTTGGAGAA TTAACTTGTT
CCCGTTGTTA    4620
AACTTAAGGG AATTTTTAGT AATGCTTGCC ACATGTATCC AGCTGCCCAG
CACTTGTGGC    4680
CTTGCTGATT TCTGCTGGCA AAGGGCTCTG GGTTTTGGTG AGTGCCTCTG
TGCTTGGCCT    4740
CCTATCCCAC CCAATGGACC AGGGAGCCAG GGTTGCTTGG CCTGCTGCAT
CTCACTGCAC    4800
CAGGGAGGGA ACCGTAGCAT CTCAGTGTCC CCAAGAGTCG GGGGAGGCCT
CACTCTGAGT    4860
GCGTTGGGTA GAAGTGGGGC TCTTACCCGA GTCAGTTCCT ATGTCTACAG
GGATACTCTA    4920
AAAAGGATGT AATGCTGGGA AGGAAAATGC TGAAAAACCT GGAATTAATT
AAGGCGAAAG    4980
AGTTCAGCAG AGCATCTTAA ACACCTTTGC CAGTGTGGGG CAGTGCCTCT
TTAAATTCTC    5040
TATTTAAATT TCATCTTTAT TTTTCAGACT TAGCATATTG TTAAGCATGC
ATAGATGTCA    5100
CTTTTGTGAT TACTTAGCCA TTTACTTTAC CCCCTTGAAC ACTGACATTT
TCCTGACTGC    5160
CATGCACGTG ATATATTTCT TTGGCATCTG AAAGGTTAGT GTTGAGAAAC
```

-continued

```
TAATTTATCA      5220
AGAAGTTAGG AGGCTGATCC TTCTTAAGAT ATGACTTCCT CACAACTTGT
AAGAGCTTCT      5280
TAGTAATTAA GATCAAATTT GTTCTTTCCG TCCTGAAATT GAATGTCCTC
TGGTTTCGTT      5340
ACTCAGTCCA TGAATTTGAT AACTTGCTGT TTCTTTTCCT GCAGAATTTA
ATTTCACTTA      5400
AAGCTTCCTG CCGCTCCTCC CCTGCCTGGC CTTCTACTAG TTGTGGCCCG
ACAGCAGGTC      5460
TAATTAGGGA CTTTTGTACA AAACTACTGT TATAATCAAT GGAAAACCTT
TGAACAACTG      5520
CATAGAAAAG AAATTAAGTA GATTATTTTT ACGAATCAAG GGCAAACTC
AGCTGTGATC      5580
GTGTGGGGTT TCAGATAAAC AGAGGGACAC ACCAGTGTAT ATATGAGTCT
TCTCCCACCC      5640
ACTAAAATCA ACCAGCTCCA TGTAAGCATG TTTTACTTTA AGATATAATT
GTTTATAAAC      5700
AGTTTTCAGA AAGGAATAAA TAATGATATT TTAATATAAT TTATTTTGAT
ATTTATGTAT      5760
TTTTATAGTT ACAGAGTTAA TTATTTTTAA AGTGCTAGAG TTTACTATTT
CATTATGAAT      5820
ATCTATGAAA GACATATAGT AACAAAATAA CTCCTTGTTT TGAAGAGCAC
ACATGTTAGG      5880
AAAAGCTGAA ATGTTTGGGG ATTGGACCTA CCCATGAAAA TACACATATC
TGTCTCCTTT      5940
CTATAAAAAG TGACTTTTGA GTCAGTTCAC CTCGTAGAAG TTTGAAATAA
AACTTAATCT      6000
AAAGTAGTGG TTCCAGGGTT CCCAGAAGTG GGCTGAAGTT TATCTTTGTA
CTGTAACTCT      6060
CAAGATAAAA GGTTTGTTGA AAAATTAGTA GCCTTGATAA AATGTCAGGG
GCACATGCAA      6120
ACTAATTTAG AAAACAGCTA TGTTAAGTAT TTGAGCACAT TAATGATCTG
AATGCAAATG      6180
GATATTCCTT CTTTATTTCT TCTTCTTCTT CTTCTTCTTT TTTTTTTTTT
TTTTTTTTTG      6240
AGACAGAGTC TTGCTCTGTC ACCCAGGCTG GAGTGCAGTG GCACAATCTT
GGCTCACTGC      6300
AGCCTCCACC TCCAGGTTTC AAGCGATTCT CCTGCTTCAG CCTCGGAGTA
GCTGTGTGAT      6360
TACAGGCACG TGCCACCACG CCTGGTTAAT TTTTGTATTT TTAGTAGAGA
TGGGGTTTCA      6420
CCATGTTGGC CAGGCTGGTC TCAAACTCCT GACCTCAGGT GATCCACCCG
CCTCAGCCTC      6480
CCAAAGTCCT GGGATTACAG GCTTGAGTCA CTGTGCCCGG CCACTTCTTT
ATTTCTTTAA      6540
CTTTGCTAAG TCTTTGCTTA GAAACACAGG GATTGCTGTA CAGTGTGGTT
ACCTGAGAAT      6600
GATTACTCTC ATAGTCTTGA TTCTGGTGAT CTGTTCTATA ATCAGTTGTG
CTGATTTTGA      6660
CTGATCTTCT CTGAAATTGG CTGAAATGAC TAAAGCTTTA TTGTATTTTG
AGTTTTTTTT      6720
AATCCGGAAT CTCCCTTCAG GAGTTTTGTT AATACCAGCT ATATTAAAGT
AGAATATGAA      6780
TATATTGTTT GCTCCCAGAA ATACACAATA AAACCTAGTT CTTAGAGATT
TTTGCAAATG      6840
TTTGTATTGC TTTTTACTTT TACTTCCTGA AGACTTTTTT TTTTTAAATC
TGGATAGGGA      6900
TATGCATGTC TGTAATACAC ACATTAGCTA AGTAAAGCCC CATAGTGCTT
AAAACAACAA      6960
TTGCCATATT CACACGAAAG ATCCTGGAGC CGCCGTAAGG AGCCAAGGGT
TCCAGGTTTG      7020
GTATGTTCAT GCCCAGTGAC TGTGGGGCTG TTAGAGGCAT CACCTGACAT
TTATTTCTCA      7080
ATATCTCTAT GAAGTAAATT ATCACTGAAG ATTCTTCCAG TTCTCTTATT
CCAAGGAAAA      7140
ATATAAGTAT TATAGCTTTG ATGGCATTAG ATTAGTATCT TTTTCTCAGC
TTACGGAGTT      7200
CTGAAAGCGT TCTCGGTCAA ATCAGAGCTG TAAAAAGCTG TTGGAGGCAA
TGCCACAGGG      7260
AGAATGTGCA TGTGTACATA TGGATAAATT AATAGAAACA GGCGCCTTTC
CCTCCCTCCT      7320
CTAACGATTA AAGACTGGCG CAGTTCTAAG ATGAATATAG ACCATATGGA
GGTACCATGC      7380
ATGAATAGGA GGGGACAGTC AGACTGTAGG TTACCTCACA GACATGCAGA
TTAAAAGACA      7440
TTGGATGAGA AAAGGTTGGA TAACAGCAAT AAAGAAAAAG ATCCTAGCTG
AGTATGGAGT      7500
GCACGCCTGT AATCCCAGCA CGTTGGGAAG CCGAGGCAGG TGGATCGTTC
GAGTTCAAGA      7560
GTTCAAGACC AGCCTGGGCA ACATGGCGAA ATCCCGTCTC TACAGAAAAT
```

```
ACAAAAATTA  7620
GCCGGGTGTT GTGGCGTGCA GCTGTAGCCC CAGCTACTCC AGGGAGGCTG
AGGTGGGAGG  7680
ATTGCTTGAG CTCGGGAGGC CCAGGCAGCA GTGAGCCAAG ATTGCACCAC
TGAACTCCAT  7740
CCCAGACGAC AGAATGAGAG ACCCTGTCTC AAAAAAATTA AGAAAAAGAT
CCTATGTCTA  7800
AGTGAAAGAA AATGTATGAT TACATGGGAC ACGCTGAAAA CTCTTTGAAA
GAGACAAGAG  7860
GTTAAGACCA AATAGAAAGA AAGGACTTTA GAAATTCTTT AGAGAACAAG
TCAGCATGAC  7920
AATATTTATT CAAACAGAGA TACTTGCTTG ACATTGGGAA ATCCCTGTGA
TAAATGCAGG  7980
ATACTGGTGA AGGCAAGAGA GTTGCAATGC AAGGGAATGG GCGCTCCCCT
TGCTGATGCT  8040
GTCTGAAGGG TCGGTGCCAA CCAATTAGTG GAGGTGTAAA TTTTCTCTGT
GCTTCTTTCA  8100
AATGATAGAT GCCATAGTAA ATTTAAAATA TTGATATGAT AACTGAGCAT
GAATTTTTTA  8160
ATTCTGCAAT TAAAAGACTT TGTTCAAAAT GCCATTAATT TTGAGTTTAG
GTGAATAAAG  8220
GGAAGCAGAA TTCTTCTGTC ATTTTTCCTT CTCCATGTGA GTTATCACTT
TTTAGGAATT  8280
AAAATAAGTA CTAACGAGTC ACCTGTTCTC TTACCAGTTT CAGTTGTCTG
CTGGTGATGG  8340
GGATGATCTC TGGAGTCATC TTTCTTTCTT TTTAAAATCC TAACTCTATT
TTATAATGCG  8400
TTGGAGTTTT TCAGACACCA TCACATGTGG TCATTTGTTC ATTCAGCAGA
CACTTCTAGG  8460
GCATTTATTA TGTGTTTTAC ATGCCGGGCA CTCTGCAGAG GTCAACAGAA
TGCCATGGGA  8520
GGGTCTCTGT TTTTGAAGAG TTTGCAGACT AATTGTGGAG GAGGTAGACA
TTAATGAAAC  8580
AAACAGATAT GATTGAATAT TCCTTTCTGA GGCAGTCACT TTTTTTTTCT
TTTTTAATGA  8640
GATAGGGACC AGACCCCGAA TCTGCCAGCC CCTTGATCTC GGACGTCCCA
GCCTCCAGAG  8700
CTGTGAGAAA TACATTTCTG ATGTTTAGAA GCTACAAATT TATGATATTT
GTTAGAGCAG  8760
CCCAAACAAA CTAGGACAGG TTGTGTGTAT GAACTGGATT GTTCTGGGGC
AAGAGTGGAA  8820
ACAGCGACTC GCCAGCCGGG AGGTGACGTG GTGTACGATG CGAGGGCCTT
GGAGGGGGTG  8880
GGTGCTGGGG CTGGAGAGGC CTGGCTGGAG ATGGGGTGTA TTTTAGGGGC
AGCATCAGGA  8940
AGATGGCGTG ATAAAGGGTG GAAGAGGTAG ATTGACTCCC CCCAAATGGT
TCTGGTTGCA  9000
GTAGCTAGAC AGGCATGCTG AGGAGGAGAA GCAAGATTTT GGAATGATCA
AGGAAGATTT  9060
AGACACCTGA AGGCTGAGGT GCCCATGAGC GCTCCCTGCA AAGGGTTGGG
TGGTCAGGTG  9120
GGTGTATGAG TTGGGGATTA GTCCCGACTG GCTGTAGCAG TACAGGTATG
TCAGTGCCAG  9180
CGACCTGGGT GGCTGATGAA GGGAGCATGT GCAGAGGCAG TAGGAGTAGC
TGTGGCTGAG  9240
CCCTGAGGGC TCCAGCGCTT AAGGTGGTTG GAGAAAGAAG GGCCCGTGAG
AAGGAGCACA  9300
CAGAGCAGTG TTTTAAGAAA GAAGGCCTCA TTTTGGGAGG CCGAGGCGGG
GGGATCATGA  9360
GGTCAAGAGA TCGAGACCAT CCTGGCCAAC ATGGTGAAAC CCCATCTCTA
CTAAAAATAC  9420
AAAAATTAGC TGGGCGTGTT GGTGCATGCC TGTAGTCCCA GCTACTTGGA
GGCTGAGGCA  9480
GGAGAATTGC TTGAAACTGG GAGGCGGAGG TTGCAGTGAG CCGAGATCGC
GCCATTGCAC  9540
TCCAGCCTGG CAACAGAGTG AGCTTTGTCT AAAAAAAAAA AAAAAAAAAA
AGAAGGCGGG  9600
CTTGTCAGCT GTATCGGAGG CTGCCAAGAG GCCTAAGATT AAAAGTGTTC
ATGGGGTTCA  9660
GCAACGTGGA GGTCAGAGGT GATATTGCCA AGTACAGTTT CAGCCAAGTA
CAGTTTCAGC  9720
GGAGCAATAG GGTTGGAAGC CACATTGGAG CCTCTTGAAG GAGAACAGAG
GGTGAGACAA  9780
TGGGGACAGC TTTATTTAGA TCGGGCTTTG GGATGTGTGG CTGAGAAGAG
AGCAGAGAAG  9840
TGGGGTGGTG GCTGGAATGG AGATAAGGCC ACGGGAAAGG ATTGCATTGT
TTGTAGGATA  9900
GGAGAATCTG GTTTTGGCTT TGGTTTTTGC TTTTCTGTAG CAGACATTTG
TTTGTTGATG  9960
GGAATAGTCC AAGACAGAGA GAGTGAGATA GAGATTTCTG GAACAGAGGC
```

```
AAGGTGCTCA 10020
AGGCTGTGAG GATCGGTCTC TCAGACACCC TGGTTGATAA TAAGAGGAAG
GACTGAGAGG 10080
GGAGGTGGGA GGACAGCAGA CACAGGGTCC TGGAGCGAAA GGCAGAGTGT
GATCAGTTGC 10140
ACCATTCCGG TGGAGGAAGC AGGGTCATCG GTTGAGAGAG CTGGGAGTTG
GAGCTTGGAT 10200
GCCGGGAGAA GAGAAGAGCT GATTGTGTGG GGTGGGAGAA GAATGTCCTA
GGAATGTAGG 10260
GCAGTGTCAG GAGCTCACAT CTTATCTGAG AATCTCGAGT TGGGCGGTTG
CTTCCCATTT 10320
TCTACCTGCA GACCCAGGAT CAGTGCGCTG CCTGAGGCAG GCCAGGGAGA
GCTGGAATTA 10380
ATTAGAACAC ACATCCCAGC TCCTCTTCCA GTGCCCAGTG CTCAGGCCCG
GTTCCCCTCT 10440
AAACGCTATT AACACACAAA GGAGGCTTTT AAGCTCCATC ACAGTACTAT
CAGCGCTGAT 10500
TAGCGCTCTG TTTCTCTTGG TGCTGTTGTC ACGCATTTTA GGCATCACGT
GTGCATTTCA 10560
CATGAACAGT GGGAAGGGAG TTGGCATGGC CTACCGTGGA TGCAGTACAG
CTATTTCCAC 10620
ATCCTCCTCC TCCTGACCTG ATTGTGTGCC CTTAGCCCAT AGGAGGCAGT
GTAATTAGAG 10680
TTCTGGGGGC TTTATTACCA ATAATGGCCT TACCACAGTC AGAAATCTCT
TTAGCCCTGA 10740
GCACTACCAT TGGGGCTAAG TGGCTCCCCT GGGTGCCGTG AGTTGTCATC
CGCAGCTTTA 10800
CGAAGAGGCA TTGAGGAAGG GGGCAGGGAT GGGGAGCAGA GTGGGAGAGA
GGGAAAAAGA 10860
AATGGGTATT CTCACAGGCA GGCTGGATTG GGCAGGCCAG GACAGCCTGG
TCTCAGGTGG 10920
GCACACGTGG GAGAGGATGG GAAGCACTCA CATGTAGCAA GTAGCTTGTC
TGTGCTGTGC 10980
TCTTGACAGA TGTTAGTCTT TCTAACCGTT CTTGGAGAGG GACTTTTCTC
TCTATTTCTT 11040
AGGTCCGGAG GCTGAGGCTG AAGAAGATGC TTGACTGGTA GGTTGTGGAC
AGTGTGTGAG 11100
GACATGGTAG GGAGGAAGCA GAGAAGACAG GCAGAACCAG GGGTCTCCAA
GACCCCTGAG 11160
TGCATTGTTG CAGGAGCGGA GACGGAAGTT CTTGCCTCAG CTTTCAGGGC
CCTGGGCTGT 11220
GGGCAGGCGG ATGGGCACCC TGGGTGTGGA GGCTTCCCTC AGAGCCTGCA
GGATGGGCTG 11280
CCTTTTACGT GAGTGACCCA CCACTTTCTC CCCAGACCTT GGTAGAATTC
CTTTGCGCTG 11340
TCATTTTCTT CTAGCAGAGC CTCCTCTCTG GGCACAGGGT GGAAACAGAA
CAGAGCCCAC 11400
ACATTTTCCA CGCATGCGGC GGGTTTCTCC ACATCACCCC CGTTTCTCGT
CTTTATTTTC 11460
ACACACACAC TTACACTGTC ATGCCTATCA GGTGGAATCA TGTGTCCCTC
CATGGCGGGA 11520
GGGCTCAGTT ACTTTATCTT CTGAGTAGAA AGGCCACACT CTGCCTGGGG
CTGGGCTGGG 11580
GGCAGGAGTG TCTGGATGCC AAGGACATGG TAGGCTGTCG GGTGCAGCGT
GATCGGGGAG 11640
GCAGAAGCGC TGTCACTTGT TGTCTCTGAT CAGGAAGACC TGGTTCCTGC
CAGCCAGTGT 11700
CTTTCTTAGG AAACAGGTCC TGTTCTGAGT ACTGGTGACA AAGTCCCCAT
TTGCAGAGTT 11760
CTTTGGAGTT CACACAGCAT TTTCCTACTG TGTCCCTCAC TTGCTGTTCG
TGTGACCCTG 11820
TGAGATGGGA AGGGGCGGGT GTCGTTATTC CTATTCGTAG CTGAGAGAGG
CTGGAACTTG 11880
AACAGGGTAT TACCTTTGTG TAGGCACATC CTAGGATTTA AATCCCTTTG
TCCTGAAAAA 11940
ACATTTGTAA TCCACATACA TTTTTCTACA GAAACAATGT TACTTGAAGA
TTCAGTTCCC 12000
CTTGCACCTG CGAGCAGTGC CTAGAACCCT CGTTTTCTGG ATTTTCTCAG
CACTCCTTCA 12060
GCAGTCCTAC TGTGTTGCTT TAGCTTGCAC TCGGGCCGCT GCTGATTTCC
ATGCTGGGGC 12120
ATCGCAGCCC AGCTGGTGTG AGCTCTGCAG GGACCAGACC CACCTCCATC
CCGCAGCCCA 12180
CACACCCAGC CCTGTTAGCT CTCCACCCAG TGCAGGCCAG TTTGCAACCA
GAACTTACCA 12240
GAACATACCT GGGAAACTGC GAAAGTTTTA AACTGTTTTA TTTTCTTGCT
CCAGTCCTGT 12300
TACTAAGGGC TGCTCCCCTG GGTGGGGGAC AGGGCTCTGT CTGAGCAGGC
TTAGAGGGAC 12360
ATAGGCTTTG GAGCAGTCCA GCAGGCTGGC AGGAGGAAGA CAGGGCCTTA
```

```
GCCAGGAGAG   12420
GGGCGGGGAG CAAGAGGGGC TTGTCTGGTG GAACTATCTT AGAGAAGTGA
TACCTGTTGA   12480
TTTCTATATG GTGCTCCCTT CCCCAGTTCC ACCTTTATTT CAAATCATTT
GAAAACCTTG   12540
ATAATGAGCC AGATTGCTGC TTTACTAATA GGAACTTCAT GCAGGAGAGA
TAAGATAGAG   12600
AGGTGACATT ATTTGGGACC AAATTCTAGA AATCTTTGCT TTAGATTTTG
GGGAAGCCAT   12660
AATTGGGAAC ACTTCATAAG CTTTTGGGAG AGTGTACTTG GTGGGGGTTG
TGGGGGGCTT   12720
AACTGTCAGC GGCTATTCCG TTGTTAAATT ATTGACGTGC AGGATAGGGA
CTGCGGAGGC   12780
TGGCAGTGAC ATATGAGGCC CTGTCAGGAT ATCTTTCAAT AATTAAGAAA
CAAGTAGTTG   12840
AAATTCCATT TTAGTTCCAG AAGCTGTGAA GCAGTTCCAT AAATGGATCA
GTTAGAGGAG   12900
TAAGTGTGTA CCCCATCCCT CAGCGGAAGT TTCCATCAGG CATCTGTGGG
AGTGGGGGCC   12960
GGGGCAGGGG TGCAGGTGCT CCCAGAGACA ACATGTCCAG GTTTAGCAAC
TCTGATAACT   13020
ATAGGACCCC AGAAGTAAAA GCACTCAGGC CCTAACTTCA GGAAGAAATG
ACAAAAAGCT   13080
TTGTCATCAG AATGGAAGTA GAAAATCCTG TAAATTACTG AGTTTTTTTT
TTTTTTTTTA   13140
ATGCACAGGT CAACCTTGAA CTTGGGTATG CCATTTCATG TCACTTGTTA
ATTGCAGGGT   13200
GGGAACCCAG TAGAAATAAT AGAGGGTGAT GCTTCCCACC TTTTCATTCC
AGAAGGCCAT   13260
GAGCAGACGC TTCTTAGCTC GAGTCCTGAC CCTTGTCTTG TCAGTGAACA
GAACTGTCCG   13320
TGCTCTGAAC GGCTCAGCCT GGGGTGGCGG CAGAAGGCGT TGCAGGTCTG
TTCTCAGTGG   13380
CAGCAGGCAC TCCATGCCTG GCCTTCTGAC CCCGGTCCTA GCGGGACGCA
CCACACCAGG   13440
CTGCCACCTG TTCAGGTCAG CTTTGGCAGA ACAACCCTCA GGTCTAAGGA
CATCGTTTTC   13500
TTTAAGGAAA ATCCTGTGTC ACTAAAAATG AGGGATTTTT AAGCAACCTG
GAGAGTTCAG   13560
AACTAGAACT AGAGTTCAGA ACTAGATCAG AACCTTCATT TTCCTGACTC
CAAATTTTCT   13620
CAGGCCCCAG TAGTTCCTGT CACATCTCCA TAGCAGATGA AGATCAGTTG
AGGGTAGAAT   13680
AACACTATCA CTGCTAAATT ATTTAGGCAG CAATTAGAAT TTGTTCAGCA
TTATTTAGGG   13740
TTTTTAAACA AACCTATCTG AGTAACCTTA TAATACTACC GTCTAAAATA
GATATTGTAT   13800
CAGTCTTATA TCAGATGAGG TGAAAGTCAC ATCTATAAAA CGCTGAACTC
TTAAATCTAA   13860
CCAGGGATGG AATATATCCT GTTAATTTGT CAAACTTCTA GAGAACCGCC
TACATGAGAC   13920
AGTAAGGATT AATCAAGCCC TACTAAGAGA GAATTTGAAA AATACAGTTT
TCTAATTATA   13980
CAGTCTCTTC TCCATGGTCC AAGGTTAATG CAGTTCTGAA TTCTGACAGT
TAGTAATAGA   14040
AAAGAAAAAA AAAAAAACCA AAGCATATGA ATTGTCTTAT AATTACCTGA
AACAGAAAGT   14100
CTCTTCTGGC AATCAAGGCC TTCTAAGCAT TAATCTGATA TTTTCAGCAT
TTGATTCTTT   14160
TCCTTTTAAA CAAGGTTGGG AATAACTGGA GGGTTGTGTG TCACTCTTTG
TGCTTATCAA   14220
ATATATGTAC TGTTTGCAGA TTTATTTTGC TTATTGCTTA GCTGTAGATG
TGTAATTCTA   14280
GGTTGAACAT TTTATCTTTT TTTCTTTTTT TTTTTACAAT TTAGACTAAC
TTATGAATAC   14340
TTCCTAGACA CTGTATCTTT GAAATACTTG ATCCTTATTC CTACTACGAA
TATAAAAACT   14400
AACAATTACT TCTTGGTTAG TTTTGGTTAG TTGTAGCTCT TGCTGCAGTT
CATCCAGGCA   14460
ACACAACAAA AATGTGCACT CTAGGGAAAG GTAAATTTAT TCCTTCATTT
ATTGCTGTCA   14520
AATATCTGTG GAATGTTTAT TGTACAGGTT GAGCATGCCA AATCCAAAAA
TCAAAATCTG   14580
AAACTTTTTT TTTTTTCTGA GATGGGGTCT TGCTCTGTTG CCCAGACTGG
AGTACAGTGG   14640
TGCAAACACA GCTCACTGCA GCCTTGACCT CCTGGGCTCA AGCAGTCCTC
CCACCTCAGC   14700
CTCCCAAGTA GCTAGGACTA CAGGTGCACG CCACCATACC TGGCTAAGTT
TTTTTATTTT   14760
CAGTAGAGAT GAGCTGTCAC TATGTTGCCT AAGCTGTTCT TGAACTCTTG
```

```
AGCTCAAACG    14820
ATCTCCCCCA CTTGGCCTCC CAAAGTGCTG GGATTACAGG CATGAACTAC
TGCACCTGGC    14880
CCAAAATCTG AAACCTTTTG CACACCAGCA TGACACTTGA AGGAAATGCT
CATGGAGCAC    14940
TCTGGATTTC AAATGTTTGG ATTTGGGATG CTCACCTGGT AAGTATAATG
CAAACATTTT    15000
AAAATCTGAA ATCTGAAACA ATTCTGCTCC TAAGCATTTT GGATAAGAGA
TATTTAACCC    15060
ATAGAGGAAA GGTACATGGA AGCCCCAGAC CACCCAAAAG AAAAGGCCTG
GGGAGAAGAT    15120
GGGCAGTTAT GGCTAGACAC CAGATTTCAG GTTTTACAGA TGGATCTGGC
ATCTCAGATC    15180
TATGAACAGA TGGATTCTTA AGGTCAGTGA CTGGCCGGGC GCGGTGGCTC
ATGCCTGTAA    15240
TCCCAGCACT TTTGGAGGCC GAGGCAGGTG GATCACCTGA GGTCAGGAGT
TCCAGACCAG    15300
CCTGGCCAAC ATAGCGAAAC CCTGTTTCTA CTAAAAATAC AAGAATTAGC
TGGGCATGGT    15360
GACGGGTGCC TGTAATCCCA GCTACTCGGG AGGCTGAGGC AGGAGAATCA
TCGCTTGAAA    15420
CTGGTAGGCA GAGGTTGCAG TGAGCCGAGA TCACGTCATT GCACTCCAGC
CTGGACAACA    15480
AGAGCAAAAC TCCATCTAAA AAAAAAAGAA AAAGAAAAAA AAGGGCAGTG
ACTATGGGAG    15540
AAAAATCAAA GACCAATATT TTACCTTGGG AAGTGCCCAC AAAGGCAGGA
AAAATAAAAG    15600
GACCTACAGA AAAGTAAAGC AGAAAGAGAA CACAAGTGTA TGGTGGTCCT
GAGAGGTTTT    15660
AGAATAGAGA GGAGTCCAAA GAGAGCAGGT GAATCAAAAG GTTCCAGGCC
AGAAGAGACC    15720
TTGGGTTTTC ATGATGACGA GACCCTCCTG TGGCCTGTGG AGCTGGCTCT
CATCAGGTCA    15780
TCAGAGCCAA CTGTGCGCAT TGCTTCCCAA GTACACGTCA TGTTGGGAGT
GGGAGATTGG    15840
CTGTGTGAAA AAATGTCTAC ACCACGGAAA TTGGCAGATA TATGGTGACC
CAGCAAACAC    15900
AGTTGACACC TGAAACATAA TTTTTAGGAA TAGTATTTAA CCTTGTATGC
GGGATCCATT    15960
CTGACCTCTA TCCTTCCCTT CTTACCTATT TCATTAAAAC AGAAGAAAAA
GCTGGTGTAA    16020
CTCATTGAAC TGATTTCATG ACCTGCAGTT TGAAAAACAT TATTTTAGAG
AAAACTGGGG    16080
ATTATGTATG CCTTACAAAG TCAGAAGACA ATTATTTTAA AAATAAATTA
TAGTAACAAT    16140
TGTAGATAGG ATGATTTCAT CTTGAAAGGA GGAAAAAAAG AATCCTAAAA
GGCTGACAAG    16200
ATGACCTCTC TAGACTAAGG ACTAAGTATG CATGCTTACA GGAGAAGAAA
AACGAGCAGA    16260
GAGAAGCGGG AGCCCTCAGA GATGGAGGGA GGAAGGGGCT GGGAGCACGG
CCTTGTGTTT    16320
GCCTGGGGAG AGGAGGCCGT GTTTTGATAG TGAAAGCTTG TTTTAGAGAA
AGTCACCTGT    16380
TCTGGAGGAT TGAGGAATGA AACTGGAAAC CTTAGGAAAA AAGCAAAGAC
ATCGGATGTA    16440
CTTGGTATTT TTTAAATTGC TTTTATTTAG TTAGCTGGAA ATGCACTTTC
TCAGATCCAC    16500
TGTCACTCCT GCAAATTACA AGAGCGCTCA GCCACCCTGT CGAAGGTCAT
CCGGCTTCCA    16560
AGCAGCAAAT TGGACCTTGA GCCCTCGTGC TGCCCTTGTT GCAAAGCTCT
TTGTCCACAC    16620
TCGCTGGCAG AGGTGGAGAG TACAGAGGGG AGGATGCTTG GCCTGTGGTG
GTCTGGCCAG    16680
CCAGGGCAGG CATGAGCTCG TCACAGGCCA GGCAGTCATC GAGTGCTCTT
TGTGGCCTGA    16740
AGTGGATTTG GCAGGTGCCT GTTATTTGAT CAGTGTCGAT GGCCAGTCGA
CACAAGTAAA    16800
TGAATCCCCA AACTTTACTC TGACCCACCT GCTTTAAACA AATTGGAGGA
AGTCATCAAG    16860
TTAGTTTCCC TAGTTTCCTC TCTGAGGACA GTCTGGGGGC TGAGGCTGGC
TGAGTCCTGT    16920
CTCCTCAGGA CAGGCCCAAA AGGAGGTACA GGGCGGCCTG GGGGACAGCA
AGGTTCAGAG    16980
TTTCAGGGCT ATGGAGATCC TGGAGCTGAT AGACGAGTGT CAGCCACAAA
GGTGAAGCTG    17040
GATTTCAGGA CCACAACAGG CGGCACGTGG GAGTTACGAA GGGGGCAGGG
CTGGGTTGCG    17100
GCCTCAGGTG CTCCTCTGGG TTGGGGCTTC TCTCCTCAGC CCCGCAGGTG
CGTCGGGCAA    17160
GCCTGTGATC ATAAGACAGG GCTGAGGGGG TCTGGGGAAG GGTACGGGAA
```

```
                                                           CCAGCAAGAG  17220
AGACCAGGGT GGGGCTGATC TTACACCCTC CACCGAACAC TTGAGTTTCC
TGCTTGTCAG  17280
TGTCACTTTT GCGTATGTGG GATTTTGGAT TGTTCCTTTT AGAGTCTCAT
GTGTACCCGA  17340
CACACTACTG TTCATATTGC CCAGTAGCTT TATATATATG TAAATATATA
TATATATATA  17400
TGGGTGCTAA ATATTTATCA AATGAATAAA GGAGGAAATG CAGATTCCAG
TTATTCATGG  17460
TGATGTTGGG AAGTACTGAA AGTCCTCTTA AATTCAAATA TCAGAAATAT
GCTCTCCCAT  17520
CTAATAAATA CTTTTTGATG GTGCTGGTAT TAATATTCAG ATATGATATA
TATTTAATAT  17580
TTATTTTTAA TATTAATATT CAGATATATA TATTTTTTAA CAAGAAGCTT
TACATTCTTC  17640
ATCTTGTGAT TTTTTGGTTA AAAGAAAGGA AGTCTGTTTA CTAAATCGCT
GTTGCATGTA  17700
GTTTCTATAA ATCGCCCTCT GTACACAGGG ATGTCAGATG CTGCCCAAGA
GAATCTGTTT  17760
CATATGGTAA TTTTCACTAA TGAATCCAGA CCTATACTGT TAAATTTTGC
CCCAAACTGC  17820
CTGGGATGAA GTAGAGGAAG CTCATGGCAG TGAGCGTGAC AGTTCTTAGA
GGACGCTATC  17880
ATAGTGTTTC ATAACAGATG CAGAGGCTCT GCAGTTCTGA ATATTAATAC
CAGCACCATC  17940
CAAAAGTATT TATTAGATGG GAGAGCATAT TTCTGATATT TGAATTTAAG
AGGACTTCCA  18000
GTACTTCCGA ACGTCACCAT CAATAATTGG AATCTGCATT TCCTCCTTTA
TTCATTCGAT  18060
AAATATTTAA CACCCATTAT GTTCATGGCA TCACATTAGA CTCTGGGGGA
GTTACAAAGA  18120
ACCTAGGCTG CTCTGCCTTC AAGGGGGAAA TAAAAGAAAC AATTACATGT
AATTGTTTTT  18180
AACACCAAGC AGCGTGAAAC CCAGCTCTGG AGCAGCCTGG TCACAAGGGG
GAGAAGAGGT  18240
CACGGGAGCC CCTCCAAGGC CAGCGCACAT GTGGCCATAC CTTGTGCCTT
CCCAAGCCCG  18300
GGCCCTCGCA CCCTTCTCTT GTCTTTCCTT GTCCTCCCAT GCCGTCAGGG
TTTATGAGAC  18360
CTGCAAGTCT CGGGGCATGG CTCTGGTCAC TCTGGGCAGC GAAGATGATT
CTCTGATGGG  18420
CTGTGGTCAG TGAAGCACAG CTTGTTTGCC TCTTTTGATT TTCCTGCAAT
GCCAGGAGAG  18480
ATTGCTCAGT TTTAGGCAGG ACTGAGATCT CCTAAAACAT GGAATTTGTA
GACAAAAATG  18540
AATACTTCCT AACATTTCCT GAGAGAGCTT TTGGTCAGCC TTATGCCTGC
AACATTGCAT  18600
TGCTGCTGGG GGACCAGGCA CACAGAGGTA GCTGCAGCTG CACCCGAACA
CGAGAGGGTG  18660
GCTGAGGAGA GTGGCCAGGC CTTCATCTCT CTGACCCAGA GTACGTGCTC
AGTAAATGAT  18720
CATCGATGAA GCAAGTGAGT CGGGACTGAA ATGTATGAGC GCCATAAGTT
TAGGCCACTG  18780
CTCATTTAAG GCCTCAGAAC TCCTGGAAGT GTTACGTGTA GAAGGTTGGC
AGGCTGGAGA  18840
GGGTAGGGGA GACCTTGAAG ATTCCCATAT TTATATTCTA GGTGGCTTGT
GTGATGTGGC  18900
CATGGCCGGA TGTCATTCAT TAACTCGTTT GACAAATATT TATTTTAGCA
CTTGTGTGCA  18960
TAGCATGTGC TGGGAATACC AGGGGAGCCA GAAGGCAGTG CTTCCGGAAC
TTGTCTGCAC  19020
GTTGGAATCA CCCGGGGAAT TGCTTACAAA TTCAAGCCCA AGCCACAGCC
CAGGCCATCA  19080
CACTCTGCAG GCACAGGGCA CAGATCTCTG TATTTTGGAA GCGCCTAAGG
GTGTTCTGAT  19140
ATCAGAGAGG TTTGCAAGTC ACGGCTGTTA GGATTTATAA TAGAGTTTTA
GATAACACAC  19200
CCAGGAAAAT TCAGTAACGA TACAAGACGG CCATCCAGAA ACCTCCTGGG
CAGGATGAGG  19260
GAGTCAAACC CAGGTGTGTG CTGTGGGCAC CACTCATTCC CCCTCAAGGA
GGATGTCGCC  19320
TGTGGATTAG GGAGCGGGAG CATCTAGGCA AACTGGACCT CTGGGGTGTG
TGTTGCTTTG  19380
CCAGGTTCGA GAGAGGGAGG AAGGGGATCC CCTTGACTCT GAACTCAGGC
AGGTCCGGAT  19440
GTGACCCGGG ATCATGGGTG GAATGCACTG GTCTATCAAG AGCTCAACTA
GTCATTGCCA  19500
TTTAAGTGGA TGAATGTTTT TCTTATAAAA GACAGACTGG GCTGGGCATG
GTGGCCCACA  19560
CCTGTAATCC CACAGCTTTG GGAGGCCAAG ATGGGAAGAT CACTTACGGC
```

-continued

```
CAGGATTTCA    19620
AGACCAGCCT GGGCAACATA GTGAGACTCC ATCTCTACAA AAGATACAAA
AAATTAGCTG    19680
GGCTTGGTGG CACGTCTGTA CTCCCAGCTA CTTGGAAGGC TGAGTTGGGA
GGATCACTTG    19740
AGCCCAGGAG CTCGAGGCTG CAGTGAGATA TGATCATGCC GCTGCACTCT
GGGCAACAGA    19800
ACGAGACCCA GTCTGGCTGC TGGCGTTTTT CCTTGTGCGT ATGTGGGCTG
AGCACGATGT    19860
GGTAAAGCAG ATCCCTCAGG ATGGACACGC TCAGCTTCGT CACTTGTTGA
TTCTCTTGCT    19920
CTTAAAATCC CCTAGCCCTC TTAACAGCCA CGGTGAACTT CCCCATGTGT
GCGTGTCAGC    19980
ACACCAATGA GCCAGCTCAG GTGGCACTTT CATGCCCCAG GGTCTTGTGG
AGCCGTGAAG    20040
CGGACGTGCG CTTAGGGTGG GGAAGGCACT TGACCTCGGC CGTCCTGGCC
GCTCTAGGTG    20160
CCTTCAGGCC TCACTGCTCA TCAGCAACCA GCCAGACCAC GTGGGCCTCA
TTTGGTATTC    20160
TTAGGACTTG CCATTTCTAA TCAATGTTTT TACTTGAGTC TGTTATATGT
TATTTCAGAG    20220
GGGGGAATGG AATGTGTTAA CACTTAGTAA ATTCTTCATG AGCTGCAACC
AAAGTTTTTC    20280
TTTCTTTCCC TTTCAACCCA CAG        20303   .
```

Intron 2 is followed (5'→3') by exon 3 which comprises 117 base pairs (nucleotides 22267–22383 of the sense strand). Exon 3 has a nucleotide sequence corresponding to SEQ ID NO:7:

```
TGTGCCATGC GGAGCTGAAT GCCATCATGA ACAAAAATTC GACCGATGTG
AAAGGCTGTA    60
GTATGTATGT TGCCTTGTTC CCTTGTAATG AATGCGCTAA GCTCATCATC
CAGGCAG      117
```

Exon 3 is followed (5'→3') by intron 3 which comprises 1357 base pairs (nucleotides 22384–23740 of the sense strand). Intron 3 has a nucleotide sequence corresponding to SEQ ID NO:8:

```
GTAGGAACCG GGTCTTTCCA TTTGTCACAT TTGCATTGCT GCCTGCTCGT
CAGTAGCTCA    60
TTGCTGATGT GTTTGATCTT AAATTGCTAT TGTTTAGATC TAAATTAATT
GCACTATCAG    120
CTTTGCAAGA TATTTCCCGT GTTTTGTTTT TGAATGGTGC CAGGTATTCT
AAGACTAATT   180
GCATCCTCTG TGATTCTTAG CATGTTTTTA ATTTAGTTTG CAACTTCTTA
AACTGCAAGC    240
TGCCAAAAAA CAACACAGGC ATTGCATATA ATTACTGTCA ATTTACTGTT
CTCTGACATA    300
TGTGCATAGA TTTGGGGGAG GGAAGAAATG AACTTCTGTC AGAAACAAGG
TCAGCTGGGA    360
GTCTGTATAT GAAATTTTAA TTTGTATCTA ATACATGGTA GATATTTGAG
GATCTCAACA    420
TACCTTGGCA TATAAATGTC ATAAGACCCA AATGGCACTA CCTTCAGGTT
TTCTTATTTT    480
ACGGTTCCCA TAAATCTACA CCATTGTATT CTGAATATTT CGCCTTTTTC
AAACTGTCAC    540
ATCTAAGATT CAGCTACACT TTGTCTCCAT AAAACTCTCG GCTGGAGATT
TAAAGACTTA    600
CCATGTTTAG CCAAATGTGT GGTTTGAAGG GGCCGTTTAT CACCAGTCCT
GTGGATCTCA    660
GAGCAGAAGC GGCCTGCTGG TACTGAGGAG TCGCGTGGGC TCCCTCGTGT
CGCCGTCACC   720
GTTCCTGGGA AGCTCTCCTC GCGGTGCCCA GGTGTGGAGG CGGTGGCAGC
CTGTGGGCCG   780
AGCAGTCCGG GCCCCACACT GCAGCCTCCT CTGCCTTCAG AGGCTGATGG
AGCAGCGGCC   840
TTCAGTGCGG GGCCCTTGGG ATTCCTGGCT GCCGAGTTAG CGCTGCCTGC
TGAGATCAGG   900
ACAAGAAAAC AGATCTGCCC TCTGTAGAGC TGGTTTGAAG TGGTCTGCAA
```

-continued

```
AGCCATGCTG    960
GGAAGCACAG TGGTGCCCAC CTCTGAATTT GCCAGCAGCC CCCACTCCCT
CCATTAGTCC   1020
TCCCACTAGT AAGAGAAGCT ACCTTGTGAT ACTGCCTTGA TTACCTGTAG
TAAGGGAAAT   1080
TGGTTAATCG GATCAAGGCT TGACTACTTG ACATGTTTTC CCTTTGCATT
TGTTTAAAAA   1140
AAAAATCCAT AAAGACTGGA GGGAAGATTA GATAGAATCC ACCCTCTGCT
GTATTAGAAA   1200
GCAGCAGATA TGTATTTCAG TGACTGGACA CTGTCTGCAA GCACACTCAG
AAAAGGTCAT   1260
TAATCATAGA CGCTGAAAGT GCTCCAGCTC GTTCCGCCTG TCTTTTGCAG
CATCTGTAGG   1320
TGCGTACACT AAGGGAGCTC CCATTGTTAC CTTACAG       1357 .
```

Intron 3 is followed (5'→3') by exon 4 which comprises 97 base pairs (nucleotides 23741–23837 of the sense strand). Exon 4 has a nucleotide sequence corresponding to SEQ ID NO:9:

```
GTATAAAAGA AGTGATTTTC ATGTCTGATA AATACCATGA TAGTGACGAG
GCAACTGCTG    60
CGAGGCTCCT GTTTAATATG GCCGGGGTGA CATTCCG      '97 .
```

Exon 4 is followed (5'→3') by intron 4 which comprises 1554 base pairs (nucleotides 23838–25391 of the sense strand). Intron 4 has a nucleotide sequence corresponding to SEQ ID NO:10:

```
GTAAGTGGGG AGAATGCGGG CGGGGGGACG GGGTAGGGTG AAGGCTGATG
AAGAGATGTA    60
TTTGACCTTG TCTCCTCCTT GTGATGCCTG ACTTCCACAC TTGGAGGTGT
CTTTAGAAAT   120
GCAAGGGCAT AAGAATTTAA AGACTATTAT AGGGGTAGAT ATTTAAGAGC
AGTGACAGGA   180
AAATCTGAAG ACCATTTGTT TAATGATTGT ACTTTAATTT CAGTAACTTT
CCGGGGTAAT   240
TAGACTAATT ATTCAAGTAC TGAGAAGTTT AAACATTCAC AAGTTTTATA
ATAGGAACGC   300
CAAACCTTGG TGAATTTTGC AAATGTAACA ACTTTGGCAT AGAAAATTTA
GGATGAAAGT   360
AGCCTGCCAG ATTGAAACAT TGGGGATTCT CTCTTTTTTT TTTTGAGACG
GAGTCTCGCT   420
CTGTCACCAG GCTAGAGTGC AGTGGTGCGA TCCTGGCTCA CTGCAACCTC
CGCTTCTCAG   480
GTTCAAGCGG TTCTCCTGCC TCAGCCTCCC CTGCCACACC CAGCTAATTT
TTTTGTACTT   540
TCAGTAGAGA CAGGGTTTCA CCATGTTGGC CAGGATGACC TCATGAGCTG
CCTGCCTCAG   600
CCTCCCAAAG TGCTGGGATT ACAGGTGTGA GCCACCTGGG GATTCTTTTT
ACAGCAACAT   660
TTTGCATTGA GATTTGAAGT CTTACAGATT TTTATGATTA TCTTTGCTAA
GAAATGGTTG   720
TGAGCTATAT TTTACTTGCA AGTAAGTTCA ACTACCTTTG ATTCATGGCA
GAAAATTCCT   780
TTGGGACTGT AAAGTTTTCC AGCGCTTCAT GGTGTTGGCG TTCAGCAGCA
GTGGGACCAT   840
GGTCATAGGT GACGTGCCCT GGCCCCTTGT GCTGGTCATT AGGGATACAG
CTCAGTGTAT   900
CTCATGAACT CAACCGTGGT GCCTTCTGAG ACTTTAATTC AAATTATTTG
TATACTCTCT   960
TGTTCAGTGA TTCTTAAAAG AATTTGTTTT GTTCCCAAAT GTTTTCTTTT
TAATTGTTGT   1020
AGAAGAAATG AGGAACGAGT GAAAAGTTAA TGAGCAAAAA AAAAAAAAAA
AAAAGTTGGT   1080
TTATGTTTGC ATTTTTAGAA CGTAATTTGA AAAATTACTC CTCACTAAAG
GTAGTCGTTT   1140
TTTGCTATAT ATAAGCGGCA AAAGAAAATT TACTATTTTT TTGCATTAGA
GAGACTCCAA   1200
GTTGGCTGCA GAAATTTTTC TAGAAAATAA GATAAATCTG ATGGGAAAAC
TAGTAATCGG   1260
```

```
ATATCATGTT GTGCAGCTGA CTTGTTAGAA ATCCTTTGAC TCCCCCAATA
ATTCGTGAAC     1320
TCAGAGAGCT GAAAACATAC AAACCACACC ACCCCATGCA TCTTTTTTTG
TCTTAGTCTT     1380
TTCTGCTCTG TGTTTCTCTT GGTATGGTGC ACTATAATTG GCTCCTATAG
AGAGAAAATA     1440
GCAAGTGAAT CCCAGGACAT ATTTTTCTCT GCACAGAAAT ATGAGTTAAG
CCAAAGTAAA     1500
CAAATTGCTT TCACTACTCA CCAGATAATA ATTGTATTTT GTTTTTATTT
TTAG           1554 .
```

Intron 4 is followed (5'→3') by exon 5 which comprises 76 base pairs (nucleotides 25392–25467 of the sense strand). Exon 5 has a nucleotide sequence corresponding to SEQ ID NO:11:

```
GAAATTCATA CCGAAGTGCA GCAAGATTGT CATTGACTTT GATTCAATTA
ACAGCAGACC     60
GAGTCAAAAG CTTCAG      76 .
```

Exon 5 is followed (5'→3') by a 3' untranslated region which comprises 1297 base pairs (nucleotides 25468–26764 of the sense strand). The 3' untranslated region has a nucleotide sequence corresponding to SEQ ID NO:12:

```
TGAGTTACAT CTCATTCAAT CTCCAGAAGA TTGGGATTAT CGTCTTCTAA
GAGGTTGCTA     60
ATGCCTTTCA TCTTGAAGTT ACACATAACT TCTTACTAGC CAGTATGGCA
AAAGTAGGCA     120
TCTAAAGAAT ATAAAGCCTC AAATCTTCCT TACTGTCTCT CTTGTCACAT
GGAATCTACA     180
TGTGTTTGAA CTATTGCTTT AGGATTTAAA ATAGGGGAGC CTGTGGTGGC
CTGGTGCACA     240
GGGCTAGAAC GAGAGTGCCT CCCCTTCTTG TGTCCTGGCT GGCTGGGATG
CTGGTGGCTC     300
TTCAGAGGAG CATCAGCTGT CTGTCATCTG CTGCGATCCG GCAGCCTCTC
TTCACTGCTA     360
CATGTGCTGG AAGGACAAAT AAATAATTGT GGTTGTGTTC TTAATGGGGA
CGAGCAGACA     420
CACTGATCTG AACATCTGGC CCAAGTGAAG CATGGCATAT AGTGCCCTTG
GAAGAAAATT     480
AGGCCTCAAA TGACAGTAGC ATTGAAGTGT TTGCTGCAGA GTTGAGGGAA
ACCCCCAGCC     540
ACCCTCCCGG AATCCGAGAT AGGGTGGCAC ATCTGTCCTG ACAGACGAGG
AGTGTAACTG     600
AACCAGGAAT ATTTCCTCCA TTCCTGCTCT CCCACTGCAC ACAGGGTGGT
GGCACATTAT     660
CCCTCTGGGG GGTGGGGACG CCTGTTGTTT TGGCTCAATT TGGGTTTGTT
GGTCACATGG     720
AGCTCTTCCA TTTCGTTTAG CTGAATAATG AGTTGTTCCT AGAGGAGACA
GCCTGTCTCT     780
CCTTGTTGCC CCCAAAGCCC ATGCCCTGCC GTGGTGGCAG CTGGGGCTGT
GGATGGGAGG     840
GGTCCCCAAC ATGGATGTGT TGCCCCTCCT CCGCATGCCA ACGCAGTTCA
TGTACAAGGC     900
CCCTCTGCAA CTGGAGAGAA AATTAATTCC TATCCCGTGA GTGGATTGTG
AGAAATTCCA     960
CCCACGTGGA GACAGCTTAC TGCAGCACTG TTGGTGTTCG GAGCTCTTCT
GTGCCCTGGC    1020
TCCATGCTTT CACCTACACA AGCATCACCT TCCTAATCAC CGCGGGGCGG
GGAGCGTGTG    1080
GCTCTGCCCC TTCTCTTTAA TCTCATTTAA TTTTTATTAA ACATGCTCAG
TACCTGTGTT    1140
GAGAAAAGGC TTTCTTTATC CTAAAGATTA TTACCTTTTT AAAGTGCTCT
TATATTTTCA    1200
TGAGTTTTTA TTTTGTCTCT GAGATTTTGT ATTCCACATT CTAGGGTATT
CTGTAATTTG    1260
GCTCCTTACC AATATTATTA AAATCTTATT AAAATCT       1297 .
```

The portion of the deoxycytidylate deaminase gene that is translated into deoxycytidylate deaminase comprises exons 1–5. The nucleotide sequence of exons 1–5 comprises 534 base pairs and corresponds to SEQ ID NO:13:

```
ATGAGTGAAG TTTCCTGCAA GAAACGGGAC GACTATTTGG AATGGCCAGA
GTATTTTATG    60
GCTGTGGCCT TCTTATCAGC ACAGAGAAGC AAAGATCCAA ATTCCCAGGT
CGGCGCCTGC    120
ATCGTGAATT CAGAAAACAA GATTGTCGGG ATTGGGTACA ATGGGATGCC
AAATGGGTGC    180
AGTGATGACG TGTTGCCTTG GAGAAGGACA GCAGAGAATA AGCTGGACAC
CAAATACCCG    240
TACGTGTGCC ATGCGGAGCT GAATGCCATC ATGAACAAAA ATTCGACCGA
TGTGAAAGGC    300
TGTAGTATGT ATGTTGCCTT GTTCCCTTGT AATGAATGCG CTAAGCTCAT
CATCCAGGCA    360
GGTATAAAAG AAGTGATTTT CATGTCTGAT AAATACCATG ATAGTGACGA
GGCAACTGCT    420
GCGAGGCTCC TGTTTAATAT GGCCGGGGTG ACATTCCGGA AATTCATACC
GAAGTGCAGC    480
AAGATTGTCA TTGACTTTGA TTCAATTAAC AGCAGACCGA GTCAAAAGCT
TCAG          534 ..
```

This nucleotide sequence (SEQ ID NO:13) translates into an amino acid sequence of deoxycytidylate deaminase having 178 amino acids corresponding to SEQ ID NO:14:

```
Met Ser Glu Val Ser Cys Lys Lys Arg Asp Asp Tyr Leu Glu
Trp Pro Glu Tyr Phe Met Ala Val Ala Phe Leu Ser Ala Gln
Arg Ser Lys Asp Pro Asn Ser Gln Val Gly Ala Cys Ile Val
Asn Ser Glu Asn Lys Ile Val Gly Ile Gly Tyr Asn Gly Met
Pro Asn Gly Cys Ser Asp Asp Val Leu Pro Trp Arg Arg Thr
Ala Glu Asn Lys Leu Asp Thr Lys Tyr Pro Tyr Val Cys His
Ala Glu Leu Asn Ala Ile Met Asn Lys Asn Ser Thr Asp Val
Lys Gly Cys Ser Met Tyr Val Ala Leu Phe Pro Cys Asn Glu
Cys Ala Lys Leu Ile Ile Gln Ala Gly Ile Lys Glu Val Ile
Phe Thr Ser Asp Lys Tyr His Asp Ser Asp Glu Ala Thr Ala
Ala Arg Leu Leu Phe Asn Met Ala Gly Val Thr Phe Arg Lys
Phe Ile Pro Lys Cys Ser Lys Ile Val Ile Asp Phe Asp Ser
Ile Asn Ser Arg Pro Ser Gln Lys Leu Gln
```

The invention further provides an oligonucleotide fragment of the DNA molecule encoding a gene for human deoxycytidylate deaminase. An oligonucleotide fragment refers to a continuous portion of the DNA molecule that is less than the entire molecule.

Also provided is an oligonucleotide molecule having a DNA sequence complementary to a fragment of the DNA encoding the gene for human deoxycytidylate deaminase. Such an oligonucleotide is useful as a probe to detect and/or hybridize to the DNA molecule encoding the gene. To this end, the invention further provides a method of detecting a gene encoding deoxycytidylate deaminase in a sample by contacting the sample with the oligonucleotide under conditions suitable for hybridization of the oligonucleotide to a DNA molecule encoding a gene for deoxycytidylate deaminase. The method further provides for detecting the resulting hybridized DNA, thereby detecting presence of the DNA molecule encoding the gene in the sample.

Having thus provided a DNA molecule encoding the gene for human deoxycytidylate deaminase and oligonucleotide fragments thereof and complementary thereto, the DNA molecule can be inserted into a suitable expression vector. Due to the length of the DNA molecule, the bacterial plasmid expression vectors are generally not suitable unless they are adapted for incorporation of large DNA sequences. Yeast artificial chromosome (YAC) vectors and viral vectors (such as baculovirus, vaccinia virus, and adenovirus vectors) can be utilized because they are capable of incorporating large foreign DNA sequences. These vectors can then be utilized to transfect suitable host cells. YAC vectors are generally used to transfect yeast cells such as Candida, while vaccinia virus and adenovirus vectors are generally used to transfect mammalian cells. Mammalian cells commonly used in such transfection experiments include CHO and COS cells. Baculovirus is generally used to transfect insect cells.

The DNA molecule is inserted into the expression vector using standard cloning procedures readily known in the art. This generally involves the use of restriction enzymes and DNA ligases, as described by Maniatis et al., *Molecular Cloning: A Laboratory Manual,* Cold Spring Harbor Laboratory Press, Cold Spring Harbor, N.Y. [1982].

Host cells are then transfected with suitable expression vectors by known methods. For example, mammalian cells and insect cells are infected with the appropriate viral vectors.

It is also possible to directly insert the DNA molecule encoding the gene for human deoxycytidylate deaminase into a host cell via techniques such as conjugation, transduction, microinjection, chemically-mediated transfection (such as calcium phosphate coprecipitation), electroporation, and liposome fusion.

The DNA molecule of the subject invention includes all elements necessary for the translation of the DNA sequence in a mammalian cell. The 5' untranslated region encodes a promoter, and stop signals are present in the 3' untranslated region. Therefore, determination of suitable regulatory elements to effect expression of the DNA encoding the deoxycytidylate deaminase is not necessary for those host cells in which the gene-encoded regulatory elements are capable of functioning. For more efficient expression of the gene product, however, it is often desirable to utilize particular promoters that highly express within a particular host cell (such combinations of promoters and host cells being known in the art). Such promoters can also be regulatable (such as inducible promoters) to control expression of the gene product. The ability to control expression of the gene product deoxycytidylate deaminase allows control of the level of alteration of nucleotide pools to prevent toxicity (due to the mutation potential from the altered pools) to the host cell.

Once the gene encoding the human deoxycytidylate deaminase has been inserted into a host cell, with or without the use of an intermediate expression vector, the host cell can be used to produce human dCMP deaminase by culturing the cell under conditions suitable for translation of the DNA molecule, thereby expressing the human dCMP deaminase. The human dCMP deaminase can then be recovered from the cell.

The dCMP deaminase encoded by the DNA of the present invention, or produced by the method herein, can be utilized to catalyze deamination of dCMP to dUMP, by selecting dCMP molecules and exposing them to the human dCMP deaminase.

Furthermore, having determined the DNA sequence of the gene encoding human dCMP deaminase, the gene can be located in a cell and altered (i.e., alter or remove the DNA sequence of the gene). This alteration will alter the level of dCMP deaminase within the cell which in turn will alter the catalysis of dCMP to dUMP in the cell. Altering the levels of these nucleotides within the cell will alter DNA replication within the cell, which can lead to mutagenesis.

Having localized the gene for human dCMP deaminase to the 4q35 chromosomal locus, alterations can be made at this locus to affect DNA replication. Such alterations can include partial or complete removal of the gene at the 4q35 locus. Complete removal would eliminate dCMP deaminase production in the cell. Such gene targeting and gene knock-out experiments can be performed by methods known in the art (see, for example: Melton, D. W., BioEssays 16(9): 633–638 (1994); Hasty, P. et al., Nature 364: 501–506 (1993); Snouwaert, J. N. et al., Science 257: 1083–1088 (1992); and McMahon, A. P. and Bradley, A., Cell 62: 1073–1085 (1990)).

EXPERIMENTAL DESIGN

Materials

The human lung fibroblast genomic library in the FIX II vector was purchased from Stratagene (Palo Alto, Calif.). HYBOND™-N nylon membranes [$\alpha$-$^{32}$P]dCTP and [$\alpha$-$^{32}$P]dATP were from Amersham (Arlington Heights, Ill.). Oligonucleotide primers were synthesized using a Millipore model 8750 DNA synthesizer (Millipore Corporation, Bedford, Mass.).

Isolation of Human dCMP Deaminase Gene Clones

Screening of the human lung fibroblast genomic library (1×10$^6$ recombinants) was performed according to standard procedures (Benton, W. D. and Davis, R. W., Science 196: 180–182 [1977]; Sambrook, J. et al., in *Molecular Cloning: A Laboratory Manual*, Maniatis et al., Eds., Cold Spring Harbor Laboratory Press, Cold Spring Harbor, N.Y. [1982]). Phage plaques were lifted in duplicate onto nylon membranes, denatured in 0.5N NaOH/1.5 NaCl, and neutralized in 1.5M NaCl/1.0M Tris HCl pH 7.5. The membranes were baked for 2 h at 80° C. and prehybridized for 2 h at 42° C. in 6×SSC containing 5×Denhardt's, 1% SDS, 50% formamide and 10% dextran sulfate. Hybridization followed for 20 h in the same buffer with 0.2 mg/ml salmon sperm DNA and $^{32}$P-labelled pCD12 cDNA (1×10$^7$ cpm/filter) containing the protein coding region of the deaminase (Weiner, K. X. B. et al., J Biol Chem 268: 12983–12989 [1989]). Positive clones were plaque purified and phage DNA was isolated as previously described (Maniatis, T. et al., Cell 15: 687–701 [1978]; Yamamoto, K. R. et al., Virology 40: 734–744 [1970]) and analyzed by Southern blotting and DNA sequence analysis.

DNA Isolation and Southern Blotting Analysis

Human genomic DNA was isolated essentially as described by Blin and Stafford (Blin, N. and Stafford, D. W., Nuc Acid Res 3: 2303–2308 [1976]). DNA was digested to completion with various restriction enzymes (10 U/µg DNA) for 2 h at 37° C. Reactions were concentrated in a Speedvac concentrator (Savant Instruments Inc., Farmingdale, N.Y.). The restricted DNA was then electrophoresed through a 1% agarose gel using the CHEF II pulse field apparatus (Bio-Rad, Hercules, Calif.) in 0.5×TBE gel running buffer for 22 h with a 1 to 6 sec ramped pulse time. DNA was transferred to HYBOND™-N nylon membranes essentially as described by Southern (Southern, E. M., J Mol Biol 98: 503–517 [1975]) and probed with $^{32}$P-labelled pCD12 cDNA. Hybridization conditions were as described previously (Weiner, K. X. B. et al., Mol Endocrinol 4: 1249–1256 [1990]). Autoradiograms were exposed to Kodak X-O-Mat film with intensifying screens for 8 days at −70° C.

DNA Sequence Analysis

The dCMP deaminase genomic clones were digested with either Sac I or Xba I to generate a series of overlapping fragments and subcloned into the pBluescript vector (Stratagene, La Jolla, Calif.). The nucleotide sequence of these fragments was determined by the Sanger dideoxy chain termination method (Sanger, F. et al., Proc Natl Acad Sci USA 74: 5463–5467 [1977]) using synthetic 18–21 mer oligonucleotides, and the method of primer extension. The various DNA fragments were linked as described in the DNasis manual.

Localization of the Deoxycytidylate Deaminase Gene by Fluorescence in situ Hybridization The chromosomal location of the gene was performed by Bios Laboratories Inc. (New Haven, Conn.) as follows:

A genomic clone which corresponds to the deoxycytidylate deaminase locus was labeled with digoxigenin dUTP by nick translation. Labelled probe was combined with 0.33 micrograms/microliter sheared human DNA and hybridized to normal human metaphase cells in a solution containing 50% formamide, 2XSSC, and 10% dextran sulfate. Normal human metaphase cells were prepared from PHA stimulated and Brdu synchronized peripheral blood lymphocytes. Hybridization signal was detected with antidigoxigenin FITC, and chromosomes were then counterstained with propidium iodide and analyzed. This experiment resulted in specific labelling of the most terminal portion of the long arm of a B-group chromosome. In order to distinguish whether this gene is located on chromosome 4 or 5, a probe which is specific for the centromere of chromosome 4 (C4Z1) and the genomic clone were cohybridized. This experiment produced labelling of the centromere of chromosome 4 and also 4q35. This clearly demonstrates that the gene which encodes deoxycytidylate deaminase localized to band 4q35. A total of 90 metaphase cells were examined, 59 of which showed specific labelling of chromosome 4.

RESULTS

Isolation of dCMP Deaminase Gene Clones

Screening of approximately 1×10$^6$ recombinants from a human lung fibroblast genomic library with the protein coding region of the deaminase cDNA (Weiner, K. X. B. et al., J Biol Chem 268: 12983–12989 [1989]) yielded three positive clones, λCD2, λCD7, and λCD21. Phage DNA was isolated, digested with Not I to release the insert, and analyzed by pulse field gel electrophoresis. The sizes of the released inserts were 15 kb for λCD2, 17 kb for λCD7, and 17 kb for λCD21.

Figure 2:
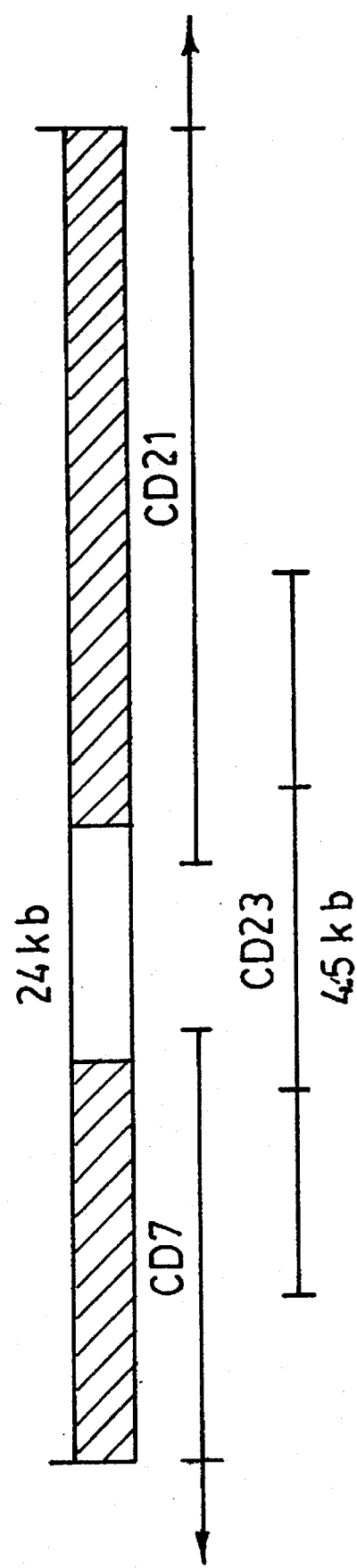
FIG. 2 illustrates the overlapping of clones λCD7, λCD21, and λCD23.

Southern blot analysis was used to determine whether these three clones overlapped. The phage DNA from all three clones was digested with Not I, separated on a 1% agarose gel, and probed with various oligos that span the entire length of the deaminase cDNA (Table I). The results demonstrate that λCD7 contains the 5' portion of the deaminase gene and λCD21 contains the 3' portion. λCD2 is contained entirely within λCD21. However, λCD7 and λCD21 did not overlap, but on further probing another clone was isolated, λCD23, which enabled the complete sequence to be obtained since it overlapped λCD7 and λCD21 (FIG. 2).

Structural Organization of the dCMP Deaminase Gene

Structural analysis of the three genomic clones reveals the deaminase gene spans about 26 kb of DNA. The gene contains 5 exons and 4 introns (see Table 1 and FIG. 1). All of the introns are located within the protein coding region of the deaminase. Interestingly, intron 2 is quite large, spanning approximately 20 kb of DNA, separating exons 1 and 2 from 3–5. All of the exons are quite small averaging about 100 bp a piece, and are separated by introns containing their characteristic AG---GT signatures.

Chromosomal Location of the Deaminase Gene

A dCMP deaminase probe (λCD21) was used to define the chromosomal locus of the deaminase gene, which was found at 4q35, the very end of this chromosome.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE 1

Size Parameters of Various Regions of the Human sCMP Deaminase Gene[+]

| Region | Exon | Intron bp | Exon-intron Boundary[++] | |
| --- | --- | --- | --- | --- |
| 1 | 108 | 402 | (1) cccagGT--------- | (2) AGgtcgg |
| 2 | 136 | 20,303 | (2) gtacgGT--------- | (3) AGtgtgc |
| 3 | 117 | 1,357 | (3) ggcagGT--------- | (4) AGgtata |
| 4 | 97 | 1,554 | (4) ttccgGT---------- | (5) AGgaaat |
| 5 | 76 | | | |
| Total | 534 | 23,616 | | |

[+]5' untranslated end - 1,317 bp; 3' untranslated end - 1,297 bp
[++]GT-AG intron region with representative flanking 3' and 5' exon regions, designated by numbers in parenthesis.

What is claimed is:

1. An isolated DNA molecule encoding a gene for human deoxycytidylate deaminase comprising a 5' untranslated region, said 5' untranslated region having a nucleotide sequence as shown in SEQ ID NO:2.

2. An isolated DNA molecule selected from the group consisting of intron 1 having a nucleotide sequence as shown in SEQ ID NO:4, intron 2 having a nucleotide sequence as shown in SEQ ID NO:6, intron 3 having a nucleotide sequence as shown in SEQ ID NO:8, and intron 4 having a nucleotide sequence as shown in SEQ ID NO:10.

3. An isolated DNA molecule encoding a gene for human deoxycytidylate deaminase wherein said DNA molecule has a nucleotide sequence comprising SEQ ID NO:1.

4. An expression vector comprising the DNA molecule of claim 3.

5. A cell transfected with the expression vector of claim 4.

6. A cell comprising the DNA molecule of claim 3.

7. A method for producing human deoxycytidylate deaminase which method comprises culturing the cell of claim 6 under conditions suitable for translation of said DNA molecule, thereby expressing said human deoxycytidylate deaminase, and recovering the human deoxycytidylate deaminase expressed thereby.

8. An oligonucleotide having a nucleotide sequence complementary to the nucleotide sequence of the isolated DNA molecule of claim 2.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
( A ) LENGTH: 26764 base pairs
( B ) TYPE: nucleic acid
( C ) STRANDEDNESS: single
( D ) TOPOLOGY: linear ( i i ) MOLECULE TYPE: DNA (genomic)

( v i i i ) POSITION IN GENOME:
( A ) CHROMOSOME/SEGMENT: 4q35

( x i ) SEQUENCE DESCRIPTION: SEQ ID NO:1:

```
GAGCTCCAGT  TCTCTCTGTT  TCTACAGCTG  GGCCTCAGTC  CTCACAGGGC  TCTAGTGGGC      60

GTTCAGCACA  CCAGGAGAAG  GCGCCCAGGG  GATTAACAGG  ACCCTTCCCT  CTCCTGCTCT     120

TCCCTCGCCC  CCCATGGCTC  CCCCTCCCTC  CTATTTAGTA  GGTACTTCTC  CAGCACCCCA     180

CAGCGATGAT  GGATGCTGGC  CCTAAAGCCA  GGTGGGAAAC  CAGGCTGATT  CAGCACCTGT     240

CTTTTCCTGT  TAGGGGGGTT  GCCAGGCCTC  TCAGATGTGG  GGCAGCGTAA  TCAGTGGGTG     300

ACCGTGGTTC  CCAGCACCCA  CTCTCCACTG  CATCCTTGTC  TTAGGCACTG  CCGCCCTGCA     360

CTGTAGCAGA  TGCCTAAATA  AAGTGTGGAG  CCTGAAGCAG  AAGTTTTGGG  AGATGCTTGC     420

CTTCCTTTAG  ACCACATTCC  TCGCCTTTCT  CAAGATTTCT  CCGTGGTACC  CACCCCGTTT     480

TTGTGTTGTC  TTCCTTCCTT  GCCCTTGTTT  CATTCCTTTT  GAAAGCGACC  ACTCCCCTGA     540
```

-continued

| | | | | | |
|---|---|---|---|---|---|
| AGTCCTAGGA | CCCCCTTCGT | GGGCTCTCCC | TGCCGTAGAC | AGTCTCTGCT | TGCCCCTGGT | 600 |
| AAACTACGTT | CCAAAAACCT | TGCTTTAGGA | GTAGCACTTG | ACGTTTTTCA | TAGTTTCTTC | 660 |
| TCATGTAATT | CATTACTCGG | AGTTGATAAC | TTCTGTCCCA | TCTGGATTAT | TGAGGAGAAA | 720 |
| GGGAAGGGAA | AAATTATCTG | GTTAATATCA | GAGTTGGGAA | GGCTTCAGAT | GTTTCTTTG | 780 |
| AATCCGTCTG | GCATGGATGA | TAATCCTGTG | TGGTTTAGGT | TAAGTTACCT | AAGTTCTCTG | 840 |
| AGTCTGTGTA | AGATGGGATG | GCACTGTCTA | CCTTAGCTAG | GAGTAAGGCT | TGAGTGACAT | 900 |
| GATGTGTATA | AACTTTAACA | ATGTCTGGAA | TCTATAGATG | ATCAATAAAT | ATTTCTTTTT | 960 |
| TCCACCCTCC | TCCTGTGCTG | ACTCCGCTTT | GTAAGGGAGA | CAGGTAAAGG | ACACAACAAT | 1020 |
| TTGTAGGCTG | GCATAAAAAA | TCCTATGAGA | GAAAGCAGTA | AATAGATGAA | ATATTTGGGA | 1080 |
| ACGTGAAGCT | ATAGGTTTCA | AATTCAAACT | TCTGAAATAG | GAAATTTCTT | AAGTTTTTAC | 1140 |
| TTAAGACCAG | AGACTGTTTA | GGGCCCATGT | GCTGTGATTT | CTGATTGATA | AATGTAGCTG | 1200 |
| AAGTTGCCCA | TGTTTAGAGA | TTTAAAGGTT | CAGTGTGGTT | GGGTTGAACT | GGAAAACAGA | 1260 |
| CTTACTAAAA | TGCTTCTCTC | AACTTCTGTT | TTGTCATGTT | TTCTTCTAG | ACCCAACATG | 1320 |
| AGTGAAGTTT | CCTGCAAGAA | ACGGGACGAC | TATTTGGAAT | GGCCAGAGTA | TTTTATGGCT | 1380 |
| GTGGCCTTCT | TATCAGCACA | GAGAAGCAAA | GATCCAAATT | CCCAGGTAAA | TGAATTTCAC | 1440 |
| GGGAGAATGC | TTAGATACTC | ACAGGCAAAG | AGATTACTGC | ACATGAGCAG | AAAGGGGAGA | 1500 |
| CTCAGTGGAC | GCCTGTCAAC | TTAAAAGTGC | AGGGTCGGTC | TGCCTTTTGT | GCTGCGTTTC | 1560 |
| TACAAGCTTA | GTTCTTCCTG | TGAGACAGAA | AATTGTCACA | TGCCATTGTT | AACTGCCTCT | 1620 |
| TGTGCCCCTT | CTGGGACTGG | GGGTGCACTT | TCCTTGGCTT | GTGGGTGCTG | CCACAAAAAA | 1680 |
| CCAGGCAAGG | AGACCGACAG | CTCTCAGCAC | CTGCAGCAGC | TATGCGTCTG | TTTTGAGTTC | 1740 |
| TGCAGTCCCC | CTGGTTTTAT | TCCCTGCTTC | CACAGCGGCA | GACCAGCCAG | TTGCAGGCAC | 1800 |
| CAAGCCTTTG | GGCATGTTTC | CTTCTAGGTC | GGCGCCTGCA | TCGTGAATTC | AGAAAACAAG | 1860 |
| ATTGTCGGGA | TTGGGTACAA | TGGGATGCCA | AATGGGTGCA | GTGATGACGT | GTTGCCTTGG | 1920 |
| AGAAGGACAG | CAGAGAATAA | GCTGGACACC | AAATACCCGT | ACGGTAGGGC | AAGTTTTATG | 1980 |
| TCCCATTCTG | CTTAGTGACA | TAGCCTGGTG | AGTGCCTAAT | TAAGAAAGTT | GGTCAGAAGG | 2040 |
| CATCATCTCC | CTTTTGTCAT | CAACAACTGG | AAAGAAAAGT | ATCCTACTGA | ACTACCCCAA | 2100 |
| TTTCCTGGCC | TTGTCTCTTA | AGTTCCAAAG | AGAGCCACGG | AGAGAAGCAT | GGTAGTGGCC | 2160 |
| ACACAGGCTG | GCCCTGAGAT | CCAGGGCTCT | GCTGCCTGTG | CTGAGCCTGG | CAGGCTTCAC | 2220 |
| TGGCAACCTG | CTGGCCTGCA | CCACACCAGT | GCACTGATAG | TCGGCGTCTC | TGCAGAGGGT | 2280 |
| CACAGCCCCT | TGCAGAGATA | GCTGAGGGAT | GTGCATGGTG | TCTCTGTGGG | TTCCTTTTTT | 2340 |
| TACTACTTGG | AAGCAGGGTC | GGCTAACCAG | GGGCTGGCTC | GGGCTTTGGT | CTGATGAGAA | 2400 |
| GCAGGCTTCA | TTCAGCCCAT | GTGCCTGATG | AGAACATCTG | GCTCAAGCTC | ATTGCTGGCA | 2460 |
| AGCAGGAATC | AAACTGTGAA | CTAGACATCA | GGAGATGGAG | GATCCAGTTG | CTTCCTCCAG | 2520 |
| TTACAGGGGA | TGCTGCAATT | TCACAGTAGG | CTGTGGTCAG | ACCAAAAGCC | AGAAGTGAGG | 2580 |
| CTGGGCACGA | TGGCTCACGC | CTGTAATCCC | AACACTTTGG | GAGGTGGAGA | CGGGCAGATC | 2640 |
| ACCTGAGGTC | AGGAGTTCGA | GACCAGCCTA | GCCAACATGG | TGAAACCCCA | TCTCTACTAA | 2700 |
| AAATACAAAA | ATTAGCTGTG | CGTGGTGGCA | GGTGCCTGTA | ATCTCAGCTA | CTCGGGAGGC | 2760 |
| TGAGGAAGGA | GAATCGCTTG | AACTCAGGAG | GTGGAGGTTG | TAGTGAGCCA | AGACTGCGCC | 2820 |
| ACTGCACTCC | AGCCTGGGTG | ACAGAGCAAG | ACTCTGTCTC | AAAAAACAAA | ACAAAAACAA | 2880 |
| ACAAACAAAA | AACAAAACAA | AAACAAAGAA | AAGAAAAGC | TAGAAGTGTA | GAACTGTAAA | 2940 |

| | | | | | |
|---|---|---|---|---|---|
| CCTTTGGCTT | GACTGTCTCT | GGATTTTCCC | CTTGAAATTA | GGGAAGGCTG | CTTCTTAGAG 3000 |
| TTTGTTGCCT | GTCTAAGCCC | CAGGGAAAAT | TCCTTCAGAG | ATTGCCTGGG | AGGGTCCAGC 3060 |
| CATAGCTTTA | CTTTTCCTTG | CATTCCTTGG | AGAATATGCA | AGCAATGCTG | GAAAAGAGGC 3120 |
| AAATCATGCT | GGGTATGCAG | GTTGCTGATT | TTTGTAAGGT | TAGGCCCTGT | ATTTTATGTC 3180 |
| TGAGAATGAA | CAGACTGGCG | CTGTTGGAAG | TGAAGGGAGA | GTAAGGCCAT | CCAAATGGGA 3240 |
| AAGATTGTGT | CTTCAGGCCA | AGGCGTGATG | TACGACCTTT | CTTCTTTGTT | GACTCTCCTG 3300 |
| GTAGGTTTTC | TTCTGGGTTT | TTCTCATGAA | GAATCCAAGT | CAACATTTAG | TCTAATTTAT 3360 |
| ATATTTTTAC | TAATGTTCCT | GGACCTCAAT | CATGTTAAAT | AAGCCCCATA | AATTTCTTTC 3420 |
| TAAATTGCCT | AGGGGCAACT | TCTCCATGTT | TGAAAGAAAA | AGTTAAGAGG | TACCTGGAGA 3480 |
| GAGAGGAGGA | ACTGAGGACT | GCAAAGCAGT | CTGGGTTTCC | AGGATGTGAA | AAGTAGTTTA 3540 |
| GGGATGAAGG | GGACCGAATC | CTCAGATCCT | TGATTTAACC | TCACCCTCCC | TCGTCGGAGT 3600 |
| GGGAAGAGAG | GATGGAGTTG | GGGGAGGGTA | AGACTGTCTT | CTCAGCACAG | CTTCAGAGCC 3660 |
| GGTGGTAGTG | GATGACTAAT | TAGAAAATG | CGCGGACTCA | GAAACTGTCA | CCCTGATTTT 3720 |
| GATTCTATAA | GCTTTTGATG | GTAAGAAAGA | AGGGAAGTGA | TTAGTTGTTT | TTAAGTCCAT 3780 |
| GCAAAGATAA | TTTTTCACAG | TGCGGTTCAA | AGTCCCTAT | AAAAATGGTG | AAAGTGGAGG 3840 |
| GTCGGATATG | TTAAAGGTCT | GCATTGAACT | GTGTGACGGC | CACAGTCAGT | ATGTCACCGA 3900 |
| GTCTGGGCAG | TGAAATATTG | GCCCTGGGGC | TGGACTTTGA | TATGGAGGAA | TTCTGGGGGG 3960 |
| ATGGCGGTCC | GTCATACTCA | AGCTGGTGCA | AAAGATACCC | GTGGTTGGAC | AGTGCGGAGG 4020 |
| GGTCCTGGGT | GAGCACTGAG | TGGGCCTCCA | ATGGGGCCTG | TGCCTTCTTC | AGTCACCCAG 4080 |
| AGCCCCCAGC | AGATCTTTAA | GCAGTGACCT | GGAAGCCAAG | GGCCATGCAG | TACATTTGCA 4140 |
| GCACCTGCCC | CACACCCCAG | ACTTCCAGC | TCTCCTGACT | TCCCGTGTAG | CTGATTTTGT 4200 |
| TGGTTATGAG | ACACTGCCTT | TTGTCCAAAT | TGAGGAGAGT | ACCTTTCAGA | GCCCCTTTCT 4260 |
| AGAAGGAATT | TTTTAAAAA | CCTGCATAGG | TATTTGTCCA | ACTTCACCGA | TTGTTTTTTA 4320 |
| TTGAATAGCT | CCTGAGCTCC | TGGGCACTGG | TTGTCTGTCT | CTGCATTATT | TTTTATTATC 4380 |
| CATATGATAC | CTCTAGGTTT | TCAAAGCTCT | TTGCTCTTAC | TTATCAATTA | TTCATTTATA 4440 |
| TGTAGCTGTG | TTAGAATGTC | GACAGTTTTC | TTTCACGAGA | GTAAGCTTGT | AATTTGATGT 4500 |
| ACCATAAAAG | TTGTAGAAGG | TATTAAATGG | TTTCTAAAAG | GCATTAGTA | TTACTGCCGC 4560 |
| CATAATACAG | TAAAGATGGG | CTTAAAGTCT | AAATGACGAT | GACTGTGTAT | AAACTGTACA 4620 |
| CTTGTTGTCT | TCTCAAGGTT | TTTCAGGCCA | CAGAGAAGTA | AATGTTTGGA | TTGCCTGGGA 4680 |
| TGTCACAGAA | ATGTTTGCTG | ATAATTGACT | CAAATGCAAA | GTCTTTTTTT | TTTTTTTGC 4740 |
| TTTCGTTTTA | AGATTTTCAA | AATTAATTTA | AAAAATAAGG | GGATACTGCC | TGGAGTTGGA 4800 |
| TAGCTCAACC | CATTCTTTCC | TCATCTACAT | TAATGGTGAC | TGAGCTGCTG | TAGCAGGAAG 4860 |
| GGTAAATTCA | TAGGTTAATC | CCTGTAAAGG | AGCTTTAGAG | ATTATCTCGA | GTTCTGGACA 4920 |
| ATGATTTTTA | ACTCTTTTGA | ATGTACAGGA | CCCTCTTTTA | AATGCTGAAA | AACTTCCAGG 4980 |
| ACCCCTGCAT | AATGCTAAAT | TCTTAGTATC | TTTTGAGTAA | GAAACTCCAC | AATGACAAAA 5040 |
| ACTACTTCGT | ATCAGTAACA | TTTTTTGTTA | ATCTGAACTT | TATTAATTGG | ATAGCATTTA 5100 |
| TGTATGTTTG | GGAAAAGTTT | ATGTATGTCC | TGGACATGGG | ATTTATCCAG | TTGTGGATAT 5160 |
| GCTTGGACCC | CTTGCAATAC | CTTAGTAGTG | TCTCAGGGTT | CTATGCCCAC | AGGATCTAAG 5220 |
| CCTCCTCCTT | TCTTGTAAGT | AACTTCTATA | ATGTCACACA | TGCAGGGTGA | CATCTCCTAA 5280 |
| TTCCAAGGTC | AGTGCTCTTC | CTGCTACCTC | CCTGTGTCTC | TCCTGTGGGG | CACATGAATT 5340 |

-continued

| | | | | | | |
|---|---|---|---|---|---|---|
| CAGCTGTACT | GAAATGCCAA | TCATTGTCTC | ATTTTTTTT | GCAGTTGATC | AGACTGAGGC | 5400 |
| TCCGATAAAA | TAATTACTCC | TCAGAGATCA | GGAGCTCGGG | GAGGGGTGGC | CTGTGTCCGG | 5460 |
| CATCATGCAG | AACAGCATGC | GTGGCTCACT | GTAACATTTC | TTCAAAGGGG | AGTGCAGTGG | 5520 |
| ACTGAATGTG | TCTCCCCCCA | AATTCACATG | TTGAAACCCT | AATTCCAATG | TGCTGATATT | 5580 |
| TGGAGGTGGG | GCCTGGGGGA | CGTAATTAGG | CCATGAGGGT | GGAGCTCTCC | TGAATGGGAT | 5640 |
| TAGTGCCCTT | CTAAAAGGGA | CCCCAGGGAG | CTCAGTTACT | CTTTTTCCAT | GTGCAAGGAT | 5700 |
| AGGCGGAGAA | GATGGCTATC | TGCAACCCTG | AAAGGAGACC | TTGCCAGAAT | CTAACCATGC | 5760 |
| TGGTGTCCTG | ACTTCCAGCC | TCCAGAACCA | TGAGAAATAA | ATGTCCATTG | TTTCTCAGCC | 5820 |
| ACCCAGTCTA | TGGGACTTTG | TTATAGCAGC | CCCAAGGGAC | TGTGACAGGG | AGCTTGAGAA | 5880 |
| CTGTGTAAAT | TTGAGTTTAC | CAAATAACAT | ACAGCTTAAT | ACTGCTTTAT | TAATTCCGTA | 5940 |
| AGTCGGAAGT | CATTAGTCCT | GATTGATGCC | TTGTGGGGAG | GAGGGAAACA | CACACTACTT | 6000 |
| GTAACATAAT | AGGAAGATGG | AGCTTTTCCT | GGGCTGTGTC | TCTAGAGAGT | TATTTTTAAA | 6060 |
| AGGGTGTTTT | TGTTCTTCCA | GTCTTGGGAT | CAAAACTTCA | TAAAACTATT | TTATTATAAT | 6120 |
| GTAGGTATTA | ATGTGGAAAA | TGAAAATTCC | CTCTGCTAAA | GAAGCTTTTT | ATTCCATCCT | 6180 |
| TTTCCTGAAA | AATCCAAAAG | ATAATATGAT | GTCAGTAACA | TTAAGTGGCA | GGAAGAAGGC | 6240 |
| AATGTTATTA | TACTAAGAAT | CTTTTCAGAT | GAATGACAAT | TAAAAAAGAG | GAAGCAGCAG | 6300 |
| ATTTATCTAA | TTTACAAGAT | TAAAAAACTT | GGGAAGATTT | TTATTTTCAT | GAGGGGGTGG | 6360 |
| GTTGCTAAAC | CCGTGATGAA | GTATTCAGTT | GACATTTTC | ATTCCTTTTT | CTTTGTGGAA | 6420 |
| TTCATTATAG | TGAAGCACAT | TTAATCAAAA | TACCAATGTT | ATCAAATGAG | GTAAAATACT | 6480 |
| CTTGGTGATT | CAGATATCAC | TCTTTCCTTG | GGTTTTCGTA | ACCGATTTTG | ATGATATAGT | 6540 |
| TTACAAATTA | GAGAGTTGGA | GAATTAACTT | GTTCCCGTTG | TTAAACTTAA | GGGAATTTTT | 6600 |
| AGTAATGCTT | GCCACATGTA | TCCAGCTGCC | CAGCACTTGT | GGCCTTGCTG | ATTTCTGCTG | 6660 |
| GCAAAGGGCT | CTGGGTTTTG | GTGAGTGCCT | CTGTGCTTGG | CCTCCTATCC | CACCCAATGG | 6720 |
| ACCAGGGAGC | CAGGGTTGCT | TGGCCTGCTG | CATCTCACTG | CACCAGGGAG | GGAACCGTAG | 6780 |
| CATCTCAGTG | TCCCCAAGAG | TCGGGGGAGG | CCTCACTCTG | AGTGCGTTGG | GTAGAAGTGG | 6840 |
| GGCTCTTACC | CGAGTCAGTT | CCTATGTCTA | CAGGGATACT | CTAAAAAGGA | TGTAATGCTG | 6900 |
| GGAAGGAAAA | TGCTGAAAAA | CCTGGAATTA | ATTAAGGCGA | AAGAGTTCAG | CAGAGCATCT | 6960 |
| TAAACACCTT | TGCCAGTGTG | GGGCAGTGCC | TCTTTAAATT | CTCTATTTAA | ATTTCATCTT | 7020 |
| TATTTTTCAG | ACTTAGCATA | TTGTTAAGCA | TGCATAGATG | TCACTTTTGT | GATTACTTAG | 7080 |
| CCATTTACTT | TACCCCCTTG | AACACTGACA | TTTTCCTGAC | TGCCATGCAC | GTGATATATT | 7140 |
| TCTTTGGCAT | CTGAAAGGTT | AGTGTTGAGA | AACTAATTTA | TCAAGAAGTT | AGGAGGCTGA | 7200 |
| TCCTTCTTAA | GATATGACTT | CCTCACAACT | TGTAAGAGCT | TCTTAGTAAT | TAAGATCAAA | 7260 |
| TTTGTTCTTT | CCGTCCTGAA | ATTGAATGTC | CTCTGGTTTC | GTTACTCAGT | CCATGAATTT | 7320 |
| GATAACTTGC | TGTTTCTTTT | CCTGCAGAAT | TTAATTTCAC | TTAAAGCTTC | CTGCCGCTCC | 7380 |
| TCCCCTGCCT | GGCCTTCTAC | TAGTTGTGGC | CCGACAGCAG | GTCTAATTAG | GGACTTTGT | 7440 |
| ACAAAACTAC | TGTTATAATC | AATGGAAAAC | CTTTGAACAA | CTGCATAGAA | AAGAAATTAA | 7500 |
| GTAGATTATT | TTTACGAATC | AAGGGGCAAA | CTCAGCTGTG | ATCGTGTGGG | GTTTCAGATA | 7560 |
| AACAGAGGGA | CACACCAGTG | TATATATGAG | TCTTCTCCCA | CCCACTAAAA | TCAACCAGCT | 7620 |
| CCATGTAAGC | ATGTTTTACT | TTAAGATATA | ATTGTTTATA | AACAGTTTTC | AGAAAGGAAT | 7680 |
| AAATAATGAT | ATTTTAATAT | AATTTATTTT | GATATTTATG | TATTTTTATA | GTTACAGAGT | 7740 |

| | | | | | |
|---|---|---|---|---|---|
| TAATTATTTT | TAAAGTGCTA | GAGTTTACTA | TTTCATTATG | AATATCTATG | AAAGACATAT 7800 |
| AGTAACAAAA | TAACTCCTTG | TTTTGAAGAG | CACACATGTT | AGGAAAAGCT | GAAATGTTTG 7860 |
| GGGATTGGAC | CTACCCATGA | AAATACACAT | ATCTGTCTCC | TTTCTATAAA | AAGTGACTTT 7920 |
| TGAGTCAGTT | CACCTCGTAG | AAGTTTGAAA | TAAAACTTAA | TCTAAAGTAG | TGGTTCCAGG 7980 |
| GTTCCCAGAA | GTGGGCTGAA | GTTTATCTTT | GTACTGTAAC | TCTCAAGATA | AAAGGTTTGT 8040 |
| TGAAAAATTA | GTAGCCTTGA | TAAAATGTCA | GGGGCACATG | CAAACTAATT | TAGAAAACAG 8100 |
| CTATGTTAAG | TATTTGAGCA | CATTAATGAT | CTGAATGCAA | ATGGATATTC | CTTCTTTATT 8160 |
| TCTTCTTCTT | CTTCTTCTTC | TTTTTTTTTT | TTTTTTTTT | TTGAGACAGA | GTCTTGCTCT 8220 |
| GTCACCCAGG | CTGGAGTGCA | GTGGCACAAT | CTTGGCTCAC | TGCAGCCTCC | ACCTCCAGGT 8280 |
| TTCAAGCGAT | TCTCCTGCTT | CAGCCTCGGA | GTAGCTGTGT | GATTACAGGC | ACGTGCCACC 8340 |
| ACGCCTGGTT | AATTTTTGTA | TTTTTAGTAG | AGATGGGGTT | TCACCATGTT | GGCCAGGCTG 8400 |
| GTCTCAAACT | CCTGACCTCA | GGTGATCCAC | CCGCCTCAGC | CTCCCAAAGT | CCTGGGATTA 8460 |
| CAGGCTTGAG | TCACTGTGCC | CGGCCACTTC | TTTATTTCTT | TAACTTTGCT | AAGTCTTTGC 8520 |
| TTAGAAACAC | AGGGATTGCT | GTACAGTGTG | GTTACCTGAG | AATGATTACT | CTCATAGTCT 8580 |
| TGATTCTGGT | GATCTGTTCT | ATAATCAGTT | GTGCTGATTT | TGACTGATCT | TCTCTGAAAT 8640 |
| TGGCTGAAAT | GACTAAAGCT | TTATTGTATT | TTGAGTTTTT | TTAATCCGG | AATCTCCCTT 8700 |
| CAGGAGTTTT | GTTAATACCA | GCTATATTAA | AGTAGAATAT | GAATATATTG | TTTGCTCCCA 8760 |
| GAAATACACA | ATAAAACCTA | GTTCTTAGAG | ATTTTTGCAA | ATGTTTGTAT | TGCTTTTTAC 8820 |
| TTTTACTTCC | TGAAGACTTT | TTTTTTTTAA | ATCTGGATAG | GGATATGCAT | GTCTGTAATA 8880 |
| CACACATTAG | CTAAGTAAAG | CCCCATAGTG | CTTAAAACAA | CAATTGCCAT | ATTCACACGA 8940 |
| AAGATCCTGG | AGCCGCCGTA | AGGAGCCAAG | GGTTCCAGGT | TTGGTATGTT | CATGCCCAGT 9000 |
| GACTGTGGGG | CTGTTAGAGG | CATCACCTGA | CATTTATTTC | TCAATATCTC | TATGAAGTAA 9060 |
| ATTATCACTG | AAGATTCTTC | CAGTTCTCTT | ATTCCAAGGA | AAAATATAAG | TATTATAGCT 9120 |
| TTGATGGCAT | TAGATTAGTA | TCTTTTCTC | AGCTTACGGA | GTTCTGAAAG | CGTTCTCGGT 9180 |
| CAAATCAGAG | CTGTAAAAAG | CTGTTGGAGG | CAATGCCACA | GGGAGAATGT | GCATGTGTAC 9240 |
| ATATGGATAA | ATTAATAGAA | ACAGGCGCCT | TTCCCTCCCT | CCTCTAACGA | TTAAAGACTG 9300 |
| GCGCAGTTCT | AAGATGAATA | TAGACCATAT | GGAGGTACCA | TGCATGAATA | GGAGGGGACA 9360 |
| GTCAGACTGT | AGGTTACCTC | ACAGACATGC | AGATTAAAAG | ACATTGGATG | AGAAAAGGTT 9420 |
| GGATAACAGC | AATAAAGAAA | AAGATCCTAG | CTGAGTATGG | AGTGCACGCC | TGTAATCCCA 9480 |
| GCACGTTGGG | AAGCCGAGGC | AGGTGGATCG | TTCGAGTTCA | AGAGTTCAAG | ACCAGCCTGG 9540 |
| GCAACATGGC | GAAATCCCGT | CTCTACAGAA | AATACAAAAA | TTAGCCGGGT | GTTGTGGCGT 9600 |
| GCAGCTGTAG | CCCCAGCTAC | TCCAGGGAGG | CTGAGGTGGG | AGGATTGCTT | GAGCTCGGGA 9660 |
| GGCCCAGGCA | GCAGTGAGCC | AAGATTGCAC | CACTGAACTC | CATCCCAGAC | GACAGAATGA 9720 |
| GAGACCCTGT | CTCAAAAAAA | TTAAGAAAAA | GATCCTATGT | CTAAGTGAAA | GAAAATGTAT 9780 |
| GATTACATGG | GACACGCTGA | AAACTCTTTG | AAAGAGACAA | GAGGTTAAGA | CCAAATAGAA 9840 |
| AGAAAGGACT | TTAGAAATTC | TTTAGAGAAC | AAGTCAGCAT | GACAATATTT | ATTCAAACAG 9900 |
| AGATACTTGC | TTGACATTGG | GAAATCCCTG | TGATAAATGC | AGGATACTGG | TGAAGGCAAG 9960 |
| AGAGTTGCAA | TGCAAGGGAA | TGGGCGCTCC | CCTTGCTGAT | GCTGTCTGAA | GGGTCGGTGC 10020 |
| CAACCAATTA | GTGGAGGTGT | AAATTTTCTC | TGTGCTTCTT | TCAAATGATA | GATGCCATAG 10080 |
| TAAATTTAAA | ATATTGATAT | GATAACTGAG | CATGAATTTT | TTAATTCTGC | AATTAAAAGA 10140 |

| | | | | | |
|---|---|---|---|---|---|
| CTTTGTTCAA | AATGCCATTA | ATTTTGAGTT | TAGGTGAATA | AAGGGAAGCA | GAATTCTTCT | 10200
| GTCATTTTTC | CTTCTCCATG | TGAGTTATCA | CTTTTTAGGA | ATTAAAATAA | GTACTAACGA | 10260
| GTCACCTGTT | CTCTTACCAG | TTTCAGTTGT | CTGCTGGTGA | TGGGATGAT | CTCTGGAGTC | 10320
| ATCTTTCTTT | CTTTTTAAAA | TCCTAACTCT | ATTTTATAAT | GCGTTGGAGT | TTTTCAGACA | 10380
| CCATCACATG | TGGTCATTTG | TTCATTCAGC | AGACACTTCT | AGGGCATTTA | TTATGTGTTT | 10440
| TACATGCCGG | GCACTCTGCA | GAGGTCAACA | GAATGCCATG | GGAGGGTCTC | TGTTTTGAA | 10500
| GAGTTTGCAG | ACTAATTGTG | GAGGAGGTAG | ACATTAATGA | AACAAACAGA | TATGATTGAA | 10560
| TATTCCTTTC | TGAGGCAGTC | ACTTTTTTTT | TCTTTTTTAA | TGAGATAGGG | ACCAGACCCC | 10620
| GAATCTGCCA | GCCCCTTGAT | CTCGGACGTC | CCAGCCTCCA | GAGCTGTGAG | AAATACATTT | 10680
| CTGATGTTTA | GAAGCTACAA | ATTTATGATA | TTTGTTAGAG | CAGCCCAAAC | AAACTAGGAC | 10740
| AGGTTGTGTG | TATGAACTGG | ATTGTTCTGG | GGCAAGAGTG | GAAACAGCGA | CTCGCCAGCC | 10800
| GGGAGGTGAC | GTGGTGTACG | ATGCGAGGGC | CTTGGAGGGG | GTGGGTGCTG | GGCTGGAGA | 10860
| GGCCTGGCTG | GAGATGGGGT | GTATTTAGG | GGCAGCATCA | GGAAGATGGC | GTGATAAAGG | 10920
| GTGGAAGAGG | TAGATTGACT | CCCCCCAAAT | GGTTCTGGTT | GCAGTAGCTA | GACAGGCATG | 10980
| CTGAGGAGGA | GAAGCAAGAT | TTTGGAATGA | TCAAGGAAGA | TTTAGACACC | TGAAGGCTGA | 11040
| GGTGCCCATG | AGCGCTCCCT | GCAAAGGGTT | GGGTGGTCAG | GTGGGTGTAT | GAGTTGGGA | 11100
| TTAGTCCCGA | CTGGCTGTAG | CAGTACAGGT | ATGTCAGTGC | CAGCGACCTG | GGTGGCTGAT | 11160
| GAAGGGAGCA | TGTGCAGAGG | CAGTAGGAGT | AGCTGTGGCT | GAGCCCTGAG | GGCTCCAGCG | 11220
| CTTAAGGTGG | TTGGAGAAAG | AAGGGCCCGT | GAGAAGGAGC | ACACAGAGCA | GTGTTTAAG | 11280
| AAAGAAGGCC | TCATTTTGGG | AGGCCGAGGC | GGGGGGATCA | TGAGGTCAAG | AGATCGAGAC | 11340
| CATCCTGGCC | AACATGGTGA | AACCCCATCT | CTACTAAAAA | TACAAAAATT | AGCTGGGCGT | 11400
| GTTGGTGCAT | GCCTGTAGTC | CCAGCTACTT | GGAGGCTGAG | GCAGGAGAAT | TGCTTGAAAC | 11460
| TGGGAGGCGG | AGGTTGCAGT | GAGCCGAGAT | CGCGCCATTG | CACTCCAGCC | TGGCAACAGA | 11520
| GTGAGCTTTG | TCTAAAAAAA | AAAAAAAAA | AAAAGAAGGC | GGGCTTGTCA | GCTGTATCGG | 11580
| AGGCTGCCAA | GAGGCCTAAG | ATTAAAAGTG | TTCATGGGGT | TCAGCAACGT | GGAGGTCAGA | 11640
| GGTGATATTG | CCAAGTACAG | TTTCAGCCAA | GTACAGTTTC | AGCGGAGCAA | TAGGGTTGGA | 11700
| AGCCACATTG | GAGCCTCTTG | AAGGAGAACA | GAGGGTGAGA | CAATGGGGAC | AGCTTTATTT | 11760
| AGATCGGGCT | TTGGGATGTG | TGGCTGAGAA | GAGAGCAGAG | AAGTGGGGTG | GTGGCTGGAA | 11820
| TGGAGATAAG | GCCACGGGAA | AGGATTGCAT | TGTTTGTAGG | ATAGGAGAAT | CTGGTTTTGG | 11880
| CTTTGGTTTT | TGCTTTTCTG | TAGCAGACAT | TTGTTTGTTG | ATGGGAATAG | TCCAAGACAG | 11940
| AGAGAGTGAG | ATAGAGATTT | CTGGAACAGA | GGCAAGGTGC | TCAAGGCTGT | GAGGATCGGT | 12000
| CTCTCAGACA | CCCTGGTTGA | TAATAAGAGG | AAGGACTGAG | AGGGGAGGTG | GGAGGACAGC | 12060
| AGACACAGGG | TCCTGGAGCG | AAAGGCAGAG | TGTGATCAGT | TGCACCATTC | CGGTGGAGGA | 12120
| AGCAGGGTCA | TCGGTTGAGA | GAGCTGGGAG | TTGGAGCTTG | GATGCCGGGA | GAAGAGAAGA | 12180
| GCTGATTGTG | TGGGGTGGGA | GAAGAATGTC | CTAGGAATGT | AGGGCAGTGT | CAGGAGCTCA | 12240
| CATCTTATCT | GAGAATCTCG | AGTTGGGCGG | TTGCTTCCCA | TTTTCTACCT | GCAGACCCAG | 12300
| GATCAGTGCG | CTGCCTGAGG | CAGGCCAGGG | AGAGCTGGAA | TTAATTAGAA | CACACATCCC | 12360
| AGCTCCTCTT | CCAGTGCCCA | GTGCTCAGGC | CCGGTTCCCC | TCTAAACGCT | ATTAACACAC | 12420
| AAAGGAGGCT | TTTAAGCTCC | ATCACAGTAC | TATCAGCGCT | GATTAGCGCT | CTGTTTCTCT | 12480
| TGGTGCTGTT | GTCACGCATT | TTAGGCATCA | CGTGTGCATT | TCACATGAAC | AGTGGGAAGG | 12540

| | | | | | | |
|---|---|---|---|---|---|---|
| GAGTTGGCAT | GGCCTACCGT | GGATGCAGTA | CAGCTATTTC | CACATCCTCC | TCCTCCTGAC | 12600 |
| CTGATTGTGT | GCCCTTAGCC | CATAGGAGGC | AGTGTAATTA | GAGTTCTGGG | GGCTTTATTA | 12660 |
| CCAATAATGG | CCTTACCACA | GTCAGAAATC | TCTTTAGCCC | TGAGCACTAC | CATTGGGGCT | 12720 |
| AAGTGGCTCC | CCTGGGTGCC | GTGAGTTGTC | ATCCGCAGCT | TTACGAAGAG | GCATTGAGGA | 12780 |
| AGGGGGCAGG | GATGGGAGC | AGAGTGGGAG | AGAGGGAAAA | AGAAATGGGT | ATTCTCACAG | 12840 |
| GCAGGCTGGA | TTGGGCAGGC | CAGGACAGCC | TGGTCTCAGG | TGGGCACACG | TGGGAGAGGA | 12900 |
| TGGGAAGCAC | TCACATGTAG | CAAGTAGCTT | GTCTGTGCTG | TGCTCTTGAC | AGATGTTAGT | 12960 |
| CTTTCTAACC | GTTCTTGGAG | AGGGACTTTT | CTCTCTATTT | CTTAGGTCCG | GAGGCTGAGG | 13020 |
| CTGAAGAAGA | TGCTTGACTG | GTAGGTTGTG | GACAGTGTGT | GAGGACATGG | TAGGGAGGAA | 13080 |
| GCAGAGAAGA | CAGGCAGAAC | CAGGGGTCTC | CAAGACCCCT | GAGTGCATTG | TTGCAGGAGC | 13140 |
| GGAGACGGAA | GTTCTTGCCT | CAGCTTTCAG | GGCCCTGGGC | TGTGGGCAGG | CGGATGGGCA | 13200 |
| CCCTGGGTGT | GGAGGCTTCC | CTCAGAGCCT | GCAGGATGGG | CTGCCTTTTA | CGTGAGTGAC | 13260 |
| CCACCACTTT | CTCCCCAGAC | CTTGGTAGAA | TTCCTTTGCG | CTGTCATTTT | CTTCTAGCAG | 13320 |
| AGCCTCCTCT | CTGGGCACAG | GGTGGAAACA | GAACAGAGCC | CACACATTTT | CCACGCATGC | 13380 |
| GGCGGGTTTC | TCCACATCAC | CCCCGTTTCT | CGTCTTTATT | TTCACACACA | CACTTACACT | 13440 |
| GTCATGCCTA | TCAGGTGGAA | TCATGTGTCC | CTCCATGGCG | GGAGGGCTCA | GTTACTTTAT | 13500 |
| CTTCTGAGTA | GAAAGGCCAC | ACTCTGCCTG | GGCTGGGCT | GGGGGCAGGA | GTGTCTGGAT | 13560 |
| GCCAAGGACA | TGGTAGGCTG | TCGGGTGCAG | CGTGATCGGG | GAGGCAGAAG | CGCTGTCACT | 13620 |
| TGTTGTCTCT | GATCAGGAAG | ACCTGGTTCC | TGCCAGCCAG | TGTCTTTCTT | AGGAAACAGG | 13680 |
| TCCTGTTCTG | AGTACTGGTG | ACAAAGTCCC | CATTTGCAGA | GTTCTTTGGA | GTTCACACAG | 13740 |
| CATTTTCCTA | CTGTGTCCCT | CACTTGCTGT | TCGTGTGACC | CTGTGAGATG | GGAAGGGGCG | 13800 |
| GGTGTCGTTA | TTCCTATTCG | TAGCTGAGAG | AGGCTGGAAC | TTGAACAGGG | TATTACCTTT | 13860 |
| GTGTAGGCAC | ATCCTAGGAT | TTAAATCCCT | TTGTCCTGAA | AAAACATTTG | TAATCCACAT | 13920 |
| ACATTTTCT | ACAGAAACAA | TGTTACTTGA | AGATTCAGTT | CCCCTTGCAC | CTGCGAGCAG | 13980 |
| TGCCTAGAAC | CCTCGTTTTC | TGGATTTTCT | CAGCACTCCT | TCAGCAGTCC | TACTGTGTTG | 14040 |
| CTTTAGCTTG | CACTCGGGCC | GCTGCTGATT | TCCATGCTGG | GGCATCGCAG | CCCAGCTGGT | 14100 |
| GTGAGCTCTG | CAGGGACCAG | ACCCACCTCC | ATCCGCAGC | CCACACACCC | AGCCCTGTTA | 14160 |
| GCTCTCCACC | CAGTGCAGGC | CAGTTTGCAA | CCAGAACTTA | CCAGAACATA | CCTGGGAAAC | 14220 |
| TGCGAAAGTT | TTAAACTGTT | TTATTTTCTT | GCTCCAGTCC | TGTTACTAAG | GGCTGCTCCC | 14280 |
| CTGGGTGGGG | GACAGGGCTC | TGTCTGAGCA | GGCTTAGAGG | GACATAGGCT | TTGGAGCAGT | 14340 |
| CCAGCAGGCT | GGCAGGAGGA | AGACAGGGCC | TTAGCCAGGA | GAGGGCGGG | GAGCAAGAGG | 14400 |
| GGCTTGTCTG | GTGGAACTAT | CTTAGAGAAG | TGATACCTGT | TGATTTCTAT | ATGGTGCTCC | 14460 |
| CTTCCCCAGT | TCCACCTTTA | TTTCAAATCA | TTTGAAAACC | TTGATAATGA | GCCAGATTGC | 14520 |
| TGCTTTACTA | ATAGGAACTT | CATGCAGGAG | AGATAAGATA | GAGAGGTGAC | ATTATTTGGG | 14580 |
| ACCAAATTCT | AGAAATCTTT | GCTTTAGATT | TTGGGGAAGC | CATAATTGGG | AACACTTCAT | 14640 |
| AAGCTTTTGG | GAGAGTGTAC | TTGGTGGGGG | TTGTGGGGGG | CTTAACTGTC | AGCGGCTATT | 14700 |
| CCGTTGTTAA | ATTATTGACG | TGCAGGATAG | GGACTGCGGA | GGCTGGCAGT | GACATATGAG | 14760 |
| GCCCTGTCAG | GATATCTTTC | AATAATTAAG | AAACAAGTAG | TTGAAATTCC | ATTTTAGTTC | 14820 |
| CAGAAGCTGT | GAAGCAGTTC | CATAAATGGA | TCAGTTAGAG | GAGTAAGTGT | GTACCCCATC | 14880 |
| CCTCAGCGGA | AGTTTCCATC | AGGCATCTGT | GGGAGTGGGG | GCCGGGGCAG | GGGTGCAGGT | 14940 |

| | | | | | | |
|---|---|---|---|---|---|---|
| GCTCCCAGAG | ACAACATGTC | CAGGTTTAGC | AACTCTGATA | ACTATAGGAC | CCCAGAAGTA | 15000 |
| AAAGCACTCA | GGCCCTAACT | TCAGGAAGAA | ATGACAAAAA | GCTTTGTCAT | CAGAATGGAA | 15060 |
| GTAGAAAATC | CTGTAAATTA | CTGAGTTTTT | TTTTTTTTT | TTAATGCACA | GGTCAACCTT | 15120 |
| GAACTTGGGT | ATGCCATTTC | ATGTCACTTG | TTAATTGCAG | GGTGGGAACC | CAGTAGAAAT | 15180 |
| AATAGAGGGT | GATGCTTCCC | ACCTTTTCAT | TCCAGAAGGC | CATGAGCAGA | CGCTTCTTAG | 15240 |
| CTCGAGTCCT | GACCCTTGTC | TTGTCAGTGA | ACAGAACTGT | CCGTGCTCTG | AACGGCTCAG | 15300 |
| CCTGGGGTGG | CGGCAGAAGG | CGTTGCAGGT | CTGTTCTCAG | TGGCAGCAGG | CACTCCATGC | 15360 |
| CTGGCCTTCT | GACCCCGGTC | CTAGCGGGAC | GCACCACACC | AGGCTGCCAC | CTGTTCAGGT | 15420 |
| CAGCTTTGGC | AGAACAACCC | TCAGGTCTAA | GGACATCGTT | TTCTTTAAGG | AAAATCCTGT | 15480 |
| GTCACTAAAA | ATGAGGGATT | TTTAAGCAAC | CTGGAGAGTT | CAGAACTAGA | ACTAGAGTTC | 15540 |
| AGAACTAGAT | CAGAACCTTC | ATTTTCCTGA | CTCCAAATTT | TCTCAGGCCC | CAGTAGTTCC | 15600 |
| TGTCACATCT | CCATAGCAGA | TGAAGATCAG | TTGAGGGTAG | AATAACACTA | TCACTGCTAA | 15660 |
| ATTATTTAGG | CAGCAATTAG | AATTTGTTCA | GCATTATTTA | GGGTTTTTAA | ACAAACCTAT | 15720 |
| CTGAGTAACC | TTATAATACT | ACCGTCTAAA | ATAGATATTG | TATCAGTCTT | ATATCAGATG | 15780 |
| AGGTGAAAGT | CACATCTATA | AAACGCTGAA | CTCTTAAATC | TAACCAGGGA | TGGAATATAT | 15840 |
| CCTGTTAATT | TGTCAAACTT | CTAGAGAACC | GCCTACATGA | GACAGTAAGG | ATTAATCAAG | 15900 |
| CCCTACTAAG | AGAGAATTTG | AAAAATACAG | TTTTCTAATT | ATACAGTCTC | TTCTCCATGG | 15960 |
| TCCAAGGTTA | ATGCAGTTCT | GAATTCTGAC | AGTTAGTAAT | AGAAAAGAAA | AAAAAAAAA | 16020 |
| CCAAAGCATA | TGAATTGTCT | TATAATTACC | TGAAACAGAA | AGTCTCTTCT | GGCAATCAAG | 16080 |
| GCCTTCTAAG | CATTAATCTG | ATATTTTCAG | CATTTGATTC | TTTTCCTTTT | AAACAAGGTT | 16140 |
| GGGAATAACT | GGAGGGTTGT | GTGTCACTCT | TTGTGCTTAT | CAAATATATG | TACTGTTTGC | 16200 |
| AGATT.TATTT | TGCTTATTGC | TTAGCTGTAG | ATGTGTAATT | CTAGGTTGAA | CATTTATCT | 16260 |
| TTTTTCTTT | TTTTTTTAC | AATTTAGACT | AACTTATGAA | TACTTCCTAG | ACACTGTATC | 16320 |
| TTTGAAATAC | TTGATCCTTA | TTCCTACTAC | GAATATAAAA | ACTAACAATT | ACTTCTTGGT | 16380 |
| TAGTTTTGGT | TAGTTGTAGC | TCTTGCTGCA | GTTCATCCAG | GCAACACAAC | AAAAATGTGC | 16440 |
| ACTCTAGGGA | AAGGTAAATT | TATTCCTTCA | TTTATTGCTG | TCAAATATCT | GTGGAATGTT | 16500 |
| TATTGTACAG | GTTGAGCATG | CCAAATCCAA | AAATCAAAAT | CTGAAACTTT | TTTTTTTTC | 16560 |
| TGAGATGGGG | TCTTGCTCTG | TTGCCCAGAC | TGGAGTACAG | TGGTGCAAAC | ACAGCTCACT | 16620 |
| GCAGCCTTGA | CCTCCTGGGC | TCAAGCAGTC | CTCCCACCTC | AGCCTCCCAA | GTAGCTAGGA | 16680 |
| CTACAGGTGC | ACGCCACCAT | ACCTGGCTAA | GTTTTTTTAT | TTTCAGTAGA | GATGAGCTGT | 16740 |
| CACTATGTTG | CCTAAGCTGT | TCTTGAACTC | TTGAGCTCAA | ACGATCTCCC | CCACTTGGCC | 16800 |
| TCCCAAAGTG | CTGGGATTAC | AGGCATGAAC | TACTGCACCT | GGCCCAAAAT | CTGAAACCTT | 16860 |
| TTGCACACCA | GCATGACACT | TGAAGGAAAT | GCTCATGGAG | CACTCTGGAT | TTCAAATGTT | 16920 |
| TGGATTTGGG | ATGCTCACCT | GGTAAGTATA | ATGCAAACAT | TTTAAAATCT | GAAATCTGAA | 16980 |
| ACAATTCTGC | TCCTAAGCAT | TTTGGATAAG | AGATATTTAA | CCCATAGAGG | AAAGGTACAT | 17040 |
| GGAAGCCCCA | GACCACCCAA | AAGAAAAGGC | CTGGGGAGAA | GATGGGCAGT | TATGGCTAGA | 17100 |
| CACCAGATTT | CAGGTTTTAC | AGATGGATCT | GGCATCTGAG | ATCTATGAAC | AGATGGATTC | 17160 |
| TTAAGGTCAG | TGACTGGCCG | GGCGCGGTGG | CTCATGCCTG | TAATCCCAGC | ACTTTGGGAG | 17220 |
| GCCGAGGCAG | GTGGATCACC | TGAGGTCAGG | AGTTCCAGAC | CAGCCTGGCC | AACATAGCGA | 17280 |
| AACCCTGTTT | CTACTAAAAA | TACAAGAATT | AGCTGGGCAT | GGTGACGGGT | GCCTGTAATC | 17340 |

| | | | | | | |
|---|---|---|---|---|---|---|
| CCAGCTACTC | GGGAGGCTGA | GGCAGGAGAA | TCATCGCTTG | AAACTGGTAG | GCAGAGGTTG | 17400 |
| CAGTGAGCCG | AGATCACGTC | ATTGCACTCC | AGCCTGGACA | ACAAGAGCAA | AACTCCATCT | 17460 |
| AAAAAAAAAA | GAAAAGAAA | AAAAAGGGCA | GTGACTATGG | GAGAAAAATC | AAAGACCAAT | 17520 |
| ATTTTACCTT | GGGAAGTGCC | CACAAAGGCA | GGAAAAATAA | AAGGACCTAC | AGAAAAGTAA | 17580 |
| AGCAGAAAGA | GAACACAAGT | GTATGGTGGT | CCTGAGAGGT | TTTAGAATAG | AGAGGAGTCC | 17640 |
| AAAGAGAGCA | GGTGAATCAA | AAGGTTCCAG | GCCAGAAGAG | ACCTTGGGTT | TTCATGATGA | 17700 |
| CGAGACCCTC | CTGTGGCCTG | TGGAGCTGGC | TCTCATCAGG | TCATCAGAGC | CAACTGTGCG | 17760 |
| CATTGCTTCC | CAAGTACACG | TCATGTTGGG | AGTGGGAGAT | TGGCTGTGTG | AAAAAATGTC | 17820 |
| TACACCACGG | AAATTGGCAG | ATATATGGTG | ACCCAGCAAA | CACAGTTGAC | ACCTGAAACA | 17880 |
| TAATTTTTAG | GAATAGTATT | TAACCTTGTA | TGCGGGATCC | ATTCTGACCT | CTATCCTTCC | 17940 |
| CTTCTTACCT | ATTTCATTAA | AACAGAAGAA | AAAGCTGGTG | TAACTCATTG | AACTGATTTC | 18000 |
| ATGACCTGCA | GTTTGAAAAA | CATTATTTTA | GAGAAACTG | GGGATTATGT | ATGCCTTACA | 18060 |
| AAGTCAGAAG | ACAATTATTT | TAAAAATAAA | TTATAGTAAC | AATTGTAGAT | AGGATGATTT | 18120 |
| CATCTTGAAA | GGAGGAAAAA | AAGAATCCTA | AAAGGCTGAC | AAGATGACCT | CTCTAGACTA | 18180 |
| AGGACTAAGT | ATGCATGCTT | ACAGGAGAAG | AAAAACGAGC | AGAGAGAAGC | GGGAGCCCTC | 18240 |
| AGAGATGGAG | GGAGGAAGGG | GCTGGGAGCA | CGGCCTTGTG | TTTGCCTGGG | GAGAGGAGGC | 18300 |
| CGTGTTTTGA | TAGTGAAAGC | TTGTTTTAGA | GAAAGTCACC | TGTTCTGGAG | GATTGAGGAA | 18360 |
| TGAAACTGGA | AACCTTAGGA | AAAAAGCAAA | GACATCGGAT | GTACTTGGTA | TTTTTTAAAT | 18420 |
| TGCTTTTATT | TAGTTAGCTG | GAAATGCACT | TTCTCAGATC | CACTGTCACT | CCTGCAAATT | 18480 |
| ACAAGAGCGC | TCAGCCACCC | TGTCGAAGGT | CATCCGGCTT | CCAAGCAGCA | AATTGGACCT | 18540 |
| TGAGCCCTCG | TGCTGCCCTT | GTTGCAAAGC | TCTTTGTCCA | CACTCGCTGG | CAGAGGTGGA | 18600 |
| GAGTACAGAG | GGGAGGATGC | TTGGCCTGTG | GTGGTCTGGC | CAGCCAGGGC | AGGCATGAGC | 18660 |
| TCGTCACAGG | CCAGGCAGTC | ATCGAGTGCT | CTTTGTGGCC | TGAAGTGGAT | TTGGCAGGTG | 18720 |
| CCTGTTATTT | GATCAGTGTC | GATGGCCAGT | CGACACAAGT | AAATGAATCC | CCAAACTTTA | 18780 |
| CTCTGACCCA | CCTGCTTTAA | ACAAATTGGA | GGAAGTCATC | AAGTTAGTTT | CCCTAGTTTC | 18840 |
| CTCTCTGAGG | ACAGTCTGGG | GGCTGAGGCT | GGCTGAGTCC | TGTCTCCTCA | GGACAGGCCC | 18900 |
| AAAAGGAGGT | ACAGGGCGGC | CTGGGGACA | GCAAGGTTCA | GAGTTTCAGG | GCTATGGAGA | 18960 |
| TCCTGGAGCT | GATAGACGAG | TGTCAGCCAC | AAAGGTGAAG | CTGGATTTCA | GGACCACAAC | 19020 |
| AGGCGGCACG | TGGGAGTTAC | GAAGGGGGCA | GGGCTGGGTT | GCGGCCTCAG | GTGCTCCTCT | 19080 |
| GGGTTGGGGC | TTCTCTCCTC | AGCCCCGCAG | GTGCGTCGGG | CAAGCCTGTG | ATCATAAGAC | 19140 |
| AGGGCTGAGG | GGGTCTGGGG | AAGGGTACGG | GAACCAGCAA | GAGAGACCAG | GGTGGGGCTG | 19200 |
| ATCTTACACC | CTCCACCGAA | CACTTGAGTT | TCCTGCTTGT | CAGTGTCACT | TTTGCGTATG | 19260 |
| TGGGATTTTG | GATTGTTCCT | TTTAGAGTCT | CATGTGTACC | CGACACACTA | CTGTTCATAT | 19320 |
| TGCCCAGTAG | CTTTATATAT | ATGTAAATAT | ATATATATAT | ATATGGGTGC | TAAATATTTA | 19380 |
| TCAAATGAAT | AAAGGAGGAA | ATGCAGATTC | CAGTTATTCA | TGGTGATGTT | GGGAAGTACT | 19440 |
| GAAAGTCCTC | TTAAATTCAA | ATATCAGAAA | TATGCTCTCC | CATCTAATAA | ATACTTTTTG | 19500 |
| ATGGTGCTGG | TATTAATATT | CAGATATGAT | ATATATTTAA | TATTTATTTT | TAATATTAAT | 19560 |
| ATTCAGATAT | ATATATTTTT | TAACAAGAAG | CTTTACATTC | TTCATCTTGT | GATTTTTGG | 19620 |
| TTAAAAGAAA | GGAAGTCTGT | TTACTAAATC | GCTGTTGCAT | GTAGTTTCTA | TAAATCGCCC | 19680 |
| TCTGTACACA | GGGATGTCAG | ATGCTGCCCA | AGAGAATCTG | TTTCATATGG | TAATTTTCAC | 19740 |

```
TAATGAATCC AGACCTATAC TGTTAAATTT TGCCCCAAAC TGCCTGGGAT GAAGTAGAGG    19800
AAGCTCATGG CAGTGAGCGT GACAGTTCTT AGAGGACGCT ATCATAGTGT TTCATAACAG    19860
ATGCAGAGGC TCTGCAGTTC TGAATATTAA TACCAGCACC ATCCAAAAGT ATTTATTAGA    19920
TGGGAGAGCA TATTTCTGAT ATTTGAATTT AAGAGGACTT CCAGTACTTC CGAACGTCAC    19980
CATCAATAAT TGGAATCTGC ATTTCCTCCT TTATTCATTC GATAAATATT TAACACCCAT    20040
TATGTTCATG GCATCACATT AGACTCTGGG GGAGTTACAA AGAACCTAGG CTGCTCTGCC    20100
TTCAAGGGGG AAATAAAAGA AACAATTACA TGTAATTGTT TTTAACACCA AGCAGCGTGA    20160
AACCCAGCTC TGGAGCAGCC TGGTCACAAG GGGGAGAAGA GGTCACGGGA GCCCTCCAA     20220
GGCCAGCGCA CATGTGGCCA TACCTTGTGC CTTCCAAGC CCGGGCCCTC GCACCCTTCT     20280
CTTGTCTTTC CTTGTCCTCC CATGCCGTCA GGGTTTATGA GACCTGCAAG TCTCGGGGCA    20340
TGGCTCTGGT CACTCTGGGC AGCGAAGATG ATTCTCTGAT GGGCTGTGGT CAGTGAAGCA    20400
CAGCTTGTTT GCCTCTTTTG ATTTTCCTGC AATGCCAGGA GAGATTGCTC AGTTTTAGGC    20460
AGGACTGAGA TCTCCTAAAA CATGGAATTT GTAGACAAAA ATGAATACTT CCTAACATTT    20520
CCTGAGAGAG CTTTTGGTCA GCCTTATGCC TGCAACATTG CATTGCTGCT GGGGGACCAG    20580
GCACACAGAG GTAGCTGCAG CTGCACCCGA ACACGAGAGG GTGGCTGAGG AGAGTGGCCA    20640
GGCCTTCATC TCTCTGACCC AGAGTACGTG CTCAGTAAAT GATCATCGAT GAAGCAAGTG    20700
AGTCGGGACT GAAATGTATG AGCGCCATAA GTTAGGCCA CTGCTCATTT AAGGCCTCAG     20760
AACTCCTGGA AGTGTTACGT GTAGAAGGTT GGCAGGCTGG AGAGGGTAGG GGAGACCTTG    20820
AAGATTCCCA TATTTATATT CTAGGTGGCT TGTGTGATGT GGCCATGGCC GGATGTCATT    20880
CATTAACTCG TTTGACAAAT ATTTATTTTA GCACTTGTGT GCATAGCATG TGCTGGGAAT    20940
ACCAGGGGAG CCAGAAGGCA GTGCTTCCGG AACTTGTCTG CACGTTGGAA TCACCCGGGG    21000
AATTGCTTAC AAATTCAAGC CCAAGCCACA GCCCAGGCCA TCACACTCTG CAGGCACAGG    21060
GCACAGATCT CTGTATTTTG GAAGCGCCTA AGGGTGTTCT GATATCAGAG AGGTTTGCAA    21120
GTCACGGCTG TTAGGATTTA TAATAGAGTT TTAGATAACA CACCCAGGAA AATTCAGTAA    21180
CGATACAAGA CGGCCATCCA GAAACCTCCT GGGCAGGATG AGGGAGTCAA ACCCAGGTGT    21240
GTGCTGTGGG CACCACTCAT TCCCCCTCAA GGAGGATGTC GCCTGTGGAT TAGGGAGCGG    21300
GAGCATCTAG GCAAACTGGA CCTCTGGGGT GTGTGTTGCT TGCCAGGTT CGAGAGAGGG     21360
AGGAAGGGGA TCCCCTTGAC TCTGAACTCA GGCAGGTCCG GATGTGACCC GGGATCATGG    21420
GTGGAATGCA CTGGTCTATC AAGAGCTCAA CTAGTCATTG CCATTTAAGT GGATGAATGT    21480
TTTTCTTATA AAAGACAGAC TGGGCTGGGC ATGGTGGCCC ACACCTGTAA TCCCACAGCT    21540
TTGGGAGGCC AAGATGGGAA GATCACTTAC GGCCAGGATT TCAAGACCAG CCTGGGCAAC    21600
ATAGTGAGAC TCCATCTCTA CAAAAGATAC AAAAAATTAG CTGGGCTTGG TGGCACGTCT    21660
GTACTCCCAG CTACTTGGAA GGCTGAGTTG GGAGGATCAC TTGAGCCCAG GAGCTCGAGG    21720
CTGCAGTGAG ATATGATCAT GCCGCTGCAC TCTGGGCAAC AGAACGAGAC CCAGTCTGGC    21780
TGCTGGCGTT TTTCCTTGTG CGTATGTGGG CTGAGCACGA TGTGGTAAAG CAGATCCCTC    21840
AGGATGGACA CGCTCAGCTT CGTCACTTGT TGATTCTCTT GCTCTTAAAA TCCCCTAGCC    21900
CTCTTAACAG CCACGGTGAA CTTCCCCATG TGTGCGTGTC AGCACACCAA TGAGCCAGCT    21960
CAGGTGGCAC TTTCATGCCC CAGGGTCTTG TGGAGCCGTG AAGCGGACGT GCGCTTAGGG    22020
TGGGGAAGGC ACTTGACCTC GGCCGTCCTG GCCGCTCTAG GTGCCTTCAG GCCTCACTGC    22080
TCATCAGCAA CCAGCCAGAC CACGTGGGCC TCATTTGGTA TTCTTAGGAC TTGCCATTTC    22140
```

```
TAATCAATGT TTTTACTTGA GTCTGTTATA TGTTATTTCA GAGGGGGGAA TGGAATGTGT      22200
TAACACTTAG TAAATTCTTC ATGAGCTGCA ACCAAAGTTT TTCTTTCTTT CCCTTTCAAC      22260
CCACAGTGTG CCATGCGGAG CTGAATGCCA TCATGAACAA AAATTCGACC GATGTGAAAG      22320
GCTGTAGTAT GTATGTTGCC TTGTTCCCTT GTAATGAATG CGCTAAGCTC ATCATCCAGG      22380
CAGGTAGGAA CCGGGTCTTT CCATTTGTCA CATTTGCATT GCTGCCTGCT CGTCAGTAGC      22440
TCATTGCTGA TGTGTTTGAT CTTAAATTGC TATTGTTTAG ATCTAAATTA ATTGCACTAT      22500
CAGCTTTGCA AGATATTTCC CGTGTTTTGT TTTTGAATGG TGCCAGGTAT TCTAAGACTA      22560
ATTGCATCCT CTGTGATTCT TAGCATGTTT TTAATTTAGT TTGCAACTTC TTAAACTGCA      22620
AGCTGCCAAA AAACAACACA GGCATTGCAT ATAATTACTG TCAATTTACT GTTCTCTGAC      22680
ATATGTGCAT AGATTTGGGG GAGGGAAGAA ATGAACTTCT GTCAGAAACA AGGTCAGCTG      22740
GGAGTCTGTA TATGAAATTT TAATTTGTAT CTAATACATG GTAGATATTT GAGGATCTCA      22800
ACATACCTTG GCATATAAAT GTCATAAGAC CCAAATGGCA CTACCTTCAG GTTTTCTTAT      22860
TTTACGGTTC CCATAAATCT ACACCATTGT ATTCTGAATA TTTCGCCTTT TTCAAACTGT      22920
CACATCTAAG ATTCAGCTAC ACTTTGTCTC CATAAAACTC TCGGCTGGAG ATTTAAAGAC      22980
TTACCATGTT TAGCCAAATG TGTGGTTTGA AGGGGCCGTT TATCACCAGT CCTGTGGATC      23040
TCAGAGCAGA AGCGGCCTGC TGGTACTGAG GAGTCGCGTG GGCTCCCTCG TGTCGCCGTC      23100
ACCGTTCCTG GGAAGCTCTC CTCGCGGTGC CCAGGTGTGG AGGCGGTGGC AGCCTGTGGG      23160
CCGAGCAGTC CGGGCCCCAC ACTGCAGCCT CCTCTGCCTT CAGAGGCTGA TGGAGCAGCG      23220
GCCTTCAGTG CGGGGCCCTT GGGATTCCTG CTGCCGAGT TAGCGCTGCC TGCTGAGATC      23280
AGGACAAGAA AACAGATCTG CCCTCTGTAG AGCTGGTTTG AAGTGGTCTG CAAAGCCATG      23340
CTGGGAAGCA CAGTGGTGCC CACCTCTGAA TTTGCCAGCA GCCCCACTC CCTCCATTAG      23400
TCCTCCCACT AGTAAGAGAA GCTACCTTGT GATACTGCCT TGATTACCTG TAGTAAGGGA      23460
AATTGGTTAA TCGGATCAAG GCTTGACTAC TTGACATGTT TTCCCTTTGC ATTTGTTTAA      23520
AAAAAAAATC CATAAAGACT GGAGGGAAGA TTAGATAGAA TCCACCCTCT GCTGTATTAG      23580
AAAGCAGCAG ATATGTATTT CAGTGACTGG ACACTGTCTG CAAGCACACT CAGAAAAGGT      23640
CATTAATCAT AGACGCTGAA AGTGCTCCAG CTCGTTCCGC CTGTCTTTTG CAGCATCTGT      23700
AGGTGCGTAC ACTAAGGGAG CTCCCATTGT TACCTTACAG GTATAAAAGA AGTGATTTTC      23760
ATGTCTGATA AATACCATGA TAGTGACGAG GCAACTGCTG CGAGGCTCCT GTTTAATATG      23820
GCCGGGGTGA CATTCCGGTA AGTGGGGAGA ATGCGGGCGG GGGACGGGG TAGGGTGAAG      23880
GCTGATGAAG AGATGTATTT GACCTTGTCT CCTCCTTGTG ATGCCTGACT TCCACACTTG      23940
GAGGTGTCTT TAGAAATGCA AGGGCATAAG AATTTAAAGA CTATTATAGG GGTAGATATT      24000
TAAGAGCAGT GACAGGAAAA TCTGAAGACC ATTTGTTTAA TGATTGTACT TTAATTTCAG      24060
TAACTTTCCG GGGTAATTAG ACTAATTATT CAAGTACTGA GAAGTTTAAA CATTCACAAG      24120
TTTTATAATA GGAACGCCAA ACCTTGGTGA ATTTTGCAAA TGTAACAACT TTGGCATAGA      24180
AAATTTAGGA TGAAAGTAGC CTGCCAGATT GAAACATTGG GGATTCTCTC TTTTTTTTT      24240
TGAGACGGAG TCTCGCTCTG TCACCAGGCT AGAGTGCAGT GGTGCGATCC TGGCTCACTG      24300
CAACCTCCGC TTCTCAGGTT CAAGCGGTTC TCCTGCCTCA GCCTCCCTG CCACACCCAG      24360
CTAATTTTTT TGTACTTTCA GTAGAGACAG GGTTTCACCA TGTTGGCCAG GATGACCTCA      24420
TGAGCTGCCT GCCTCAGCCT CCCAAAGTGC TGGGATTACA GGTGTGAGCC ACCTGGGGAT      24480
TCTTTTTACA GCAACATTTT GCATTGAGAT TTGAAGTCTT ACAGATTTTT ATGATTATCT      24540
```

| | | | | | | |
|---|---|---|---|---|---|---|
| TTGCTAAGAA | ATGGTTGTGA | GCTATATTTT | ACTTGCAAGT | AAGTTCAACT | ACCTTTGATT | 24600 |
| CATGGCAGAA | AATTCCTTTG | GGACTGTAAA | GTTTTCCAGC | GCTTCATGGT | GTTGGCGTTC | 24660 |
| AGCAGCAGTG | GGACCATGGT | CATAGGTGAC | GTGCCCTGGC | CCCTTGTGCT | GGTCATTAGG | 24720 |
| GATACAGCTC | AGTGTATCTC | ATGAACTCAA | CCGTGGTGCC | TTCTGAGACT | TTAATTCAAA | 24780 |
| TTATTTGTAT | ACTCTCTTGT | TCAGTGATTC | TTAAAAGAAT | TTGTTTTGTT | CCCAAATGTT | 24840 |
| TTCTTTTTAA | TTGTTGTAGA | AGAAATGAGG | AACGAGTGAA | AAGTTAATGA | GCAAAAAAA | 24900 |
| AAAAAAAAAA | AGTTGGTTTA | TGTTTGCATT | TTTAGAACGT | AATTTGAAAA | ATTACTCCTC | 24960 |
| ACTAAAGGTA | GTCGTTTTTT | GCTATATATA | AGCGGCAAAA | GAAATTTAC | TATTTTTTG | 25020 |
| CATTAGAGAG | ACTCCAAGTT | GGCTGCAGAA | ATTTTCTAG | AAAATAAGAT | AAATCTGATG | 25080 |
| GGAAAACTAG | TAATCGGATA | TCATGTTGTG | CAGCTGACTT | GTTAGAAATC | CTTTGACTCC | 25140 |
| CCCAATAATT | CGTGAACTCA | GAGAGCTGAA | AACATACAAA | CCACACCACC | CCATGCATCT | 25200 |
| TTTTTGTCT | TAGTCTTTTC | TGCTCTGTGT | TTCTCTTGGT | ATGGTGCACT | ATAATTGGCT | 25260 |
| CCTATAGAGA | GAAAATAGCA | AGTGAATCCC | AGGACATATT | TTTCTCTGCA | CAGAAATATG | 25320 |
| AGTTAAGCCA | AAGTAAACAA | ATTGCTTTCA | CTACTCACCA | GATAATAATT | GTATTTGTT | 25380 |
| TTTATTTTA | GGAAATTCAT | ACCGAAGTGC | AGCAAGATTG | TCATTGACTT | TGATTCAATT | 25440 |
| AACAGCAGAC | CGAGTCAAAA | GCTTCAGTGA | GTTACATCTC | ATTCAATCTC | CAGAAGATTG | 25500 |
| GGATTATCGT | CTTCTAAGAG | GTTGCTAATG | CCTTTCATCT | TGAAGTTACA | CATAACTTCT | 25560 |
| TACTAGCCAG | TATGGCAAAA | GTAGGCATCT | AAAGAATATA | AAGCCTCAAA | TCTTCCTTAC | 25620 |
| TGTCTCTCTT | GTCACATGGA | ATCTACATGT | GTTTGAACTA | TTGCTTTAGG | ATTTAAAATA | 25680 |
| GGGGAGCCTG | TGGTGGCCTG | GTGCACAGGG | CTAGAACGAG | AGTGCCTCCC | CTTCTTGTGT | 25740 |
| CCTGGCTGGC | TGGGATGCTG | GTGGCTCTTC | AGAGGAGCAT | CAGCTGTCTG | TCATCTGCTG | 25800 |
| CGATCCGGCA | GCCTCTCTTC | ACTGCTACAT | GTGCTGGAAG | GACAAATAAA | TAATTGTGGT | 25860 |
| TGTGTTCTTA | ATGGGGACGA | GCAGACACAC | TGATCTGAAC | ATCTGGCCCA | AGTGAAGCAT | 25920 |
| GGCATATAGT | GCCCTTGGAA | GAAAATTAGG | CCTCAAATGA | CAGTAGCATT | GAAGTGTTTG | 25980 |
| CTGCAGAGTT | GAGGGAAACC | CCCAGCCACC | CTCCCGGAAT | CCGAGATAGG | GTGGCACATC | 26040 |
| TGTCCTGACA | GACGAGGAGT | GTAACTGAAC | CAGGAATATT | TCCTCCATTC | CTGCTCTCCC | 26100 |
| ACTGCACACA | GGGTGGTGGC | ACATTATCCC | TCTGGGGGGT | GGGGACGCCT | GTTGTTTTGG | 26160 |
| CTCAATTTGG | GTTTGTTGGT | CACATGGAGC | TCTTCCATTT | CGTTTAGCTG | AATAATGAGT | 26220 |
| TGTTCCTAGA | GGAGACAGCC | TGTCTCTCCT | TGTTGCCCCC | AAAGCCCATG | CCCTGCCGTG | 26280 |
| GTGGCAGCTG | GGGCTGTGGA | TGGGAGGGGT | CCCCAACATG | GATGTGTTGC | CCCTCCTCCG | 26340 |
| CATGCCAACG | CAGTTCATGT | ACAAGGCCCC | TCTGCAACTG | GAGAGAAAAT | TAATTCCTAT | 26400 |
| CCCGTGAGTG | GATTGTGAGA | AATTCCACCC | ACGTGGAGAC | AGCTTACTGC | AGCACTGTTG | 26460 |
| GTGTTCGGAG | CTCTTCTGTG | CCCTGGCTCC | ATGCTTTCAC | CTACACAAGC | ATCACCTTCC | 26520 |
| TAATCACCGC | GGGGCGGGGA | GCGTGTGGCT | CTGCCCCTTC | TCTTTAATCT | CATTTAATTT | 26580 |
| TTATTAAACA | TGCTCAGTAC | CTGTGTTGAG | AAAAGGCTTT | CTTTATCCTA | AAGATTATTA | 26640 |
| CCTTTTTAAA | GTGCTCTTAT | ATTTTCATGA | GTTTTTATTT | TGTCTCTGAG | ATTTTGTATT | 26700 |
| CCACATTCTA | GGGTATTCTG | TAATTTGGCT | CCTTACCAAT | ATTATTAAAA | TCTTATTAAA | 26760 |
| ATCT | | | | | | 26764 |

( 2 ) INFORMATION FOR SEQ ID NO:2:

( i ) SEQUENCE CHARACTERISTICS:

(A) LENGTH: 1317 base pairs
(B) TYPE: nucleic acid
(C) STRANDEDNESS: double
(D) TOPOLOGY: linear (i i) MOLECULE TYPE: DNA (genomic)

(v i i i) POSITION IN GENOME:
(A) CHROMOSOME/SEGMENT: 4q35

(x i) SEQUENCE DESCRIPTION: SEQ ID NO:2:

| | | | | | | |
|---|---|---|---|---|---|---|
| GAGCTCCAGT | TCTCTCTGTT | TCTACAGCTG | GGCCTCAGTC | CTCACAGGGC | TCTAGTGGGC | 60 |
| GTTCAGCACA | CCAGGAGAAG | GCGCCCAGGG | GATTAACAGG | ACCCTTCCCT | CTCCTGCTCT | 120 |
| TCCCTCGCCC | CCCATGGCTC | CCCCTCCCTC | CTATTTAGTA | GGTACTTCTC | CAGCACCCCA | 180 |
| CAGCGATGAT | GGATGCTGGC | CCTAAAGCCA | GGTGGGAAAC | CAGGCTGATT | CAGCACCTGT | 240 |
| CTTTTCCTGT | TAGGGGGGTT | GCCAGGCCTC | TCAGATGTGG | GGCAGCGTAA | TCAGTGGGTG | 300 |
| ACCGTGGTTC | CCAGCACCCA | CTCTCCACTG | CATCCTTGTC | TTAGGCACTG | CCGCCCTGCA | 360 |
| CTGTAGCAGA | TGCCTAAATA | AAGTGTGGAG | CCTGAAGCAG | AAGTTTTGGG | AGATGCTTGC | 420 |
| CTTCCTTTAG | ACCACATTCC | TCGCCTTTCT | CAAGATTTCT | CCGTGGTACC | CACCCCGTTT | 480 |
| TTGTGTTGTC | TTCCTTCCTT | GCCCTTGTTT | CATTCCTTTT | GAAAGCGACC | ACTCCCCTGA | 540 |
| AGTCCTAGGA | CCCCCTTCGT | GGGCTCTCCC | TGCCGTAGAC | AGTCTCTGCT | TGCCCCTGGT | 600 |
| AAACTACGTT | CCAAAAACCT | TGCTTTAGGA | GTAGCACTTG | ACGTTTTCA | TAGTTTCTTC | 660 |
| TCATGTAATT | CATTACTCGG | AGTTGATAAC | TTCTGTCCCA | TCTGGATTAT | TGAGGAGAAA | 720 |
| GGGAAGGGAA | AAATTATCTG | GTTAATATCA | GAGTTGGGAA | GGCTTCAGAT | GTTTCTTTG | 780 |
| AATCCGTCTG | GCATGGATGA | TAATCCTGTG | TGGTTTAGGT | TAAGTTACCT | AAGTTCTCTG | 840 |
| AGTCTGTGTA | AGATGGGATG | GCACTGTCTA | CCTTAGCTAG | GAGTAAGGCT | TGAGTGACAT | 900 |
| GATGTGTATA | AACTTTAACA | ATGTCTGGAA | TCTATAGATG | ATCAATAAAT | ATTTCTTTTT | 960 |
| TCCACCCTCC | TCCTGTGCTG | ACTCCGCTTT | GTAAGGGAGA | CAGGTAAAGG | ACACAACAAT | 1020 |
| TTGTAGGCTG | GCATAAAAAA | TCCTATGAGA | GAAAGCAGTA | AATAGATGAA | ATATTTGGGA | 1080 |
| ACGTGAAGCT | ATAGGTTTCA | AATTCAAACT | TCTGAAATAG | GAAATTTCTT | AAGTTTTTAC | 1140 |
| TTAAGACCAG | AGACTGTTTA | GGGCCCATGT | GCTGTGATTT | CTGATTGATA | AATGTAGCTG | 1200 |
| AAGTTGCCCA | TGTTAGAGA | TTTAAAGGTT | CAGTGTGGTT | GGGTTGAACT | GGAAAACAGA | 1260 |
| CTTACTAAAA | TGCTTCTCTC | AACTTCTGTT | TTGTCATGTT | TTTCTTCTAG | ACCCAAC | 1317 |

(2) INFORMATION FOR SEQ ID NO:3:

(i) SEQUENCE CHARACTERISTICS:
(A) LENGTH: 108 base pairs
(B) TYPE: nucleic acid
(C) STRANDEDNESS: double
(D) TOPOLOGY: linear (i i) MOLECULE TYPE: DNA (genomic)

(v i i i) POSITION IN GENOME:
(A) CHROMOSOME/SEGMENT: 4q35

(x) PUBLICATION INFORMATION:
(A) AUTHORS: Weiner, Karen X.B.
Weiner, Russell S.
Maley, Frank
Maley, Gladys F.
(B) TITLE: Primary Structure of Human
Deoxycytidylate Deaminase and Overexpression of Its
Functional Protein in Escherichia coli
(C) JOURNAL: J. Biol. Chem.
(D) VOLUME: 268

(E) ISSUE: 17
(F) PAGES: 12983-12989
(G) DATE: June 15-1993

(xi) SEQUENCE DESCRIPTION: SEQ ID NO:3:

```
ATGAGTGAAG TTTCCTGCAA GAAACGGGAC GACTATTTGG AATGGCCAGA GTATTTATG        60
GCTGTGGCCT TCTTATCAGC ACAGAGAAGC AAAGATCCAA ATTCCCAG                   108
```

(2) INFORMATION FOR SEQ ID NO:4:

(i) SEQUENCE CHARACTERISTICS:
        (A) LENGTH: 402 base pairs
        (B) TYPE: nucleic acid
        (C) STRANDEDNESS: double
        (D) TOPOLOGY: linear (ii) MOLECULE TYPE: DNA (genomic)

(viii) POSITION IN GENOME:
        (A) CHROMOSOME/SEGMENT: 4q35

(xi) SEQUENCE DESCRIPTION: SEQ ID NO:4:

```
GTAAATGAAT TTCACGGGAG AATGCTTAGA TACTCACAGG CAAAGAGATT ACTGCACATG        60
AGCAGAAAGG GGAGACTCAG TGGACGCCTG TCAACTTAAA AGTGCAGGGT CGGTCTGCCT       120
TTTGTGCTGC GTTTCTACAA GCTTAGTTCT TCCTGTGAGA CAGAAAATTG TCACATGCCA       180
TTGTTAACTG CCTCTTGTGC CCCTTCTGGG ACTGGGGGTG CACTTTCCTT GGCTTGTGGG       240
TGCTGCCACA AAAACCAGG CAAGGAGACC GACAGCTCTC AGCACCTGCA GCAGCTATGC        300
GTCTGTTTTG AGTTCTGCAG TCCCCCTGGT TTTATTCCCT GCTTCCACAG CGGCAGACCA       360
GCCAGTTGCA GGCACCAAGC CTTTGGGCAT GTTTCCTTCT AG                         402
```

(2) INFORMATION FOR SEQ ID NO:5:

(i) SEQUENCE CHARACTERISTICS:
        (A) LENGTH: 136 base pairs
        (B) TYPE: nucleic acid
        (C) STRANDEDNESS: double
        (D) TOPOLOGY: linear (ii) MOLECULE TYPE: DNA (genomic)

(viii) POSITION IN GENOME:
        (A) CHROMOSOME/SEGMENT: 4q35

(x) PUBLICATION INFORMATION:
        (A) AUTHORS: Weiner, Karen X.B.
            Weiner, Russell S.
            Maley, Frank
            Maley, Gladys F.
        (B) TITLE: Primary Structure of Human
            Deoxycytidylate Deaminase and Overexpression of Its
            Functional Protein in Escherichia coli
        (C) JOURNAL: J. Biol. Chem.
        (D) VOLUME: 268
        (E) ISSUE: 17
        (F) PAGES: 12983-12989
        (G) DATE: June 15-1993

(xi) SEQUENCE DESCRIPTION: SEQ ID NO:5:

```
GTCGGCGCCT GCATCGTGAA TTCAGAAAAC AAGATTGTCG GGATTGGGTA CAATGGGATG        60
CCAAATGGGT GCAGTGATGA CGTGTTGCCT TGGAGAAGGA CAGCAGAGAA TAAGCTGGAC       120
ACCAAATACC CGTACG                                                      136
```

(2) INFORMATION FOR SEQ ID NO:6:

(i) SEQUENCE CHARACTERISTICS:

(A) LENGTH: 20303 base pairs
(B) TYPE: nucleic acid
(C) STRANDEDNESS: single
(D) TOPOLOGY: linear (ii) MOLECULE TYPE: DNA (genomic)

(viii) POSITION IN GENOME:
(A) CHROMOSOME/SEGMENT: 4q35

(xi) SEQUENCE DESCRIPTION: SEQ ID NO:6:

| | | | | | | |
|---|---|---|---|---|---|---|
| GTAGGGCAAG | TTTTATGTCC | CATTCTGCTT | AGTGACATAG | CCTGGTGAGT | GCCTAATTAA | 60 |
| GAAAGTTGGT | CAGAAGGCAT | CATCTCCCTT | TTGTCATCAA | CAACTGGAAA | GAAAAGTATC | 120 |
| CTACTGAACT | ACCCCAATTT | CCTGGCCTTG | TCTCTTAAGT | TCCAAAGAGA | GCCACGGAGA | 180 |
| GAAGCATGGT | AGTGGCCACA | CAGGCTGGCC | CTGAGATCCA | GGGCTCTGCT | GCCTGTGCTG | 240 |
| AGCCTGGCAG | GCTTCACTGG | CAACCTGCTG | GCCTGCACCA | CACCAGTGCA | CTGATAGTCG | 300 |
| GCGTCTCTGC | AGAGGGTCAC | AGCCCCTTGC | AGAGATAGCT | GAGGGATGTG | CATGGTGTCT | 360 |
| CTGTGGGTTC | CTTTTTTTAC | TACTTGGAAG | CAGGGTCGGC | TAACCAGGGG | CTGGCTCGGG | 420 |
| CTTTGGTCTG | ATGAGAAGCA | GGCTTCATTC | AGCCCATGTG | CCTGATGAGA | ACATCTGGCT | 480 |
| CAAGCTCATT | GCTGGCAAGC | AGGAATCAAA | CTGTGAACTA | GACATCAGGA | GATGGAGGAT | 540 |
| CCAGTTGCTT | CCTCCAGTTA | CAGGGGATGC | TGCAATTTCA | CAGTAGGCTG | TGGTCAGACC | 600 |
| AAAAGCCAGA | AGTGAGGCTG | GCACGATGG | CTCACGCCTG | TAATCCCAAC | ACTTTGGGAG | 660 |
| GTGGAGACGG | GCAGATCACC | TGAGGTCAGG | AGTTCGAGAC | CAGCCTAGCC | AACATGGTGA | 720 |
| AACCCCATCT | CTACTAAAAA | TACAAAAATT | AGCTGTGCGT | GGTGGCAGGT | GCCTGTAATC | 780 |
| TCAGCTACTC | GGGAGGCTGA | GGAAGGAGAA | TCGCTTGAAC | TCAGGAGGTG | GAGGTTGTAG | 840 |
| TGAGCCAAGA | CTGCGCCACT | GCACTCCAGC | CTGGGTGACA | GAGCAAGACT | CTGTCTCAAA | 900 |
| AAACAAAACA | AAAACAAACA | AACAAAAAAC | AAAACAAAAA | CAAAGAAAAG | AAAAAGCTAG | 960 |
| AAGTGTAGAA | CTGTAAACCT | TTGGCTTGAC | TGTCTCTGGA | TTTTCCCCTT | GAAATTAGGG | 1020 |
| AAGGCTGCTT | CTTAGAGTTT | GTTGCCTGTC | TAAGCCCCAG | GGAAAATTCC | TTCAGAGATT | 1080 |
| GCCTGGGAGG | GTCCAGCCAT | AGCTTTACTT | TTCCTTGCAT | TCCTTGGAGA | ATATGCAAGC | 1140 |
| AATGCTGGAA | AAGAGGCAAA | TCATGCTGGG | TATGCAGGTT | GCTGATTTTT | GTAAGGTTAG | 1200 |
| GCCCTGTATT | TTATGTCTGA | GAATGAACAG | ACTGGCGCTG | TTGGAAGTGA | AGGGAGAGTA | 1260 |
| AGGCCATCCA | AATGGGAAAG | ATTGTGTCTT | CAGGCCAAGG | CGTGATGTAC | GACCTTTCTT | 1320 |
| CTTTGTTGAC | TCTCCTGGTA | GGTTTTCTTC | TGGGTTTTTC | TCATGAAGAA | TCCAAGTCAA | 1380 |
| CATTTAGTCT | AATTTATATA | TTTTTACTAA | TGTTCCTGGA | CCTCAATCAT | GTTAAATAAG | 1440 |
| CCCCATAAAT | TTCTTTCTAA | ATTGCCTAGG | GGCAACTTCT | CCATGTTTGA | AAGAAAAGT | 1500 |
| TAAGAGGTAC | CTGGAGAGAG | AGGAGGAACT | GAGGACTGCA | AAGCAGTCTG | GGTTTCCAGG | 1560 |
| ATGTGAAAAG | TAGTTTAGGG | ATGAAGGGGA | CCGAATCCTC | AGATCCTTGA | TTTAACCTCA | 1620 |
| CCCTCCCTCG | TCGGAGTGGG | AAGAGAGGAT | GGAGTTGGGG | GAGGGTAAGA | CTGTCTTCTC | 1680 |
| AGCACAGCTT | CAGAGCCGGT | GGTAGTGGAT | GACTAATTAG | AAAAATGCGC | GGACTCAGAA | 1740 |
| ACTGTCACCC | TGATTTTGAT | TCTATAAGCT | TTTGATGGTA | AGAAAGAAGG | GAAGTGATTA | 1800 |
| GTTGTTTTTA | AGTCCATGCA | AAGATAATTT | TTCACAGTGC | GGTTCAAAGT | CCCCTATAAA | 1860 |
| AATGGTGAAA | GTGGAGGGTC | GGATATGTTA | AAGGTCTGCA | TTGAACTGTG | TGACGGCCAC | 1920 |
| AGTCAGTATG | TCACCGAGTC | TGGGCAGTGA | AATATTGGCC | CTGGGGCTGG | ACTTTGATAT | 1980 |
| GGAGGAATTC | TGGGGGGATG | GCGGTCCGTC | ATACTCAAGC | TGGTGCAAAA | GATACCCGTG | 2040 |

| | | | | | | |
|---|---|---|---|---|---|---|
| GTTGGACAGT | GCGGAGGGGT | CCTGGGTGAG | CACTGAGTGG | GCCTCCAATG | GGGCCTGTGC | 2100 |
| CTTCTTCAGT | CACCCAGAGC | CCCCAGCAGA | TCTTTAAGCA | GTGACCTGGA | AGCCAAGGGC | 2160 |
| CATGCAGTAC | ATTTGCAGCA | CCTGCCCCAC | ACCCCAGACT | TCCCAGCTCT | CCTGACTTCC | 2220 |
| CGTGTAGCTG | ATTTGTTGG | TTATGAGACA | CTGCCTTTTG | TCCAAATTGA | GGAGAGTACC | 2280 |
| TTTCAGAGCC | CCTTTCTAGA | AGGAATTTTT | TTAAAAACCT | GCATAGGTAT | TTGTCCAACT | 2340 |
| TCACCGATTG | TTTTTTATTG | AATAGCTCCT | GAGCTCCTGG | GCACTGGTTG | TCTGTCTCTG | 2400 |
| CATTATTTTT | TATTATCCAT | ATGATACCTC | TAGGTTTTCA | AAGCTCTTTG | CTCTTACTTA | 2460 |
| TCAATTATTC | ATTTATATGT | AGCTGTGTTA | GAATGTCGAC | AGTTTCTTT | CACGAGAGTA | 2520 |
| AGCTTGTAAT | TTGATGTACC | ATAAAGTTG | TAGAAGGTAT | TAAATGGTTT | CTAAAAGGCA | 2580 |
| TTTAGTATTA | CTGCCGCCAT | AATACAGTAA | AGATGGGCTT | AAAGTCTAAA | TGACGATGAC | 2640 |
| TGTGTATAAA | CTGTACACTT | GTTGTCTTCT | CAAGGTTTTT | CAGGCCACAG | AGAAGTAAAT | 2700 |
| GTTGGATTG | CCTGGGATGT | CACAGAAATG | TTTGCTGATA | ATTGACTCAA | ATGCAAAGTC | 2760 |
| TTTTTTTTT | TTTTGCTTT | CGTTTTAAGA | TTTTCAAAAT | TAATTTAAAA | AATAAGGGGA | 2820 |
| TACTGCCTGG | AGTTGGATAG | CTCAACCCAT | TCTTTCCTCA | TCTACATTAA | TGGTGACTGA | 2880 |
| GCTGCTGTAG | CAGGAAGGGT | AAATTCATAG | GTTAATCCCT | GTAAAGGAGC | TTTAGAGATT | 2940 |
| ATCTCGAGTT | CTGGACAATG | ATTTTTAACT | CTTTTGAATG | TACAGGACCC | TCTTTTAAAT | 3000 |
| GCTGAAAAAC | TTCCAGGACC | CCTGCATAAT | GCTAAATTCT | TAGTATCTTT | TGAGTAAGAA | 3060 |
| ACTCCACAAT | GACAAAAACT | ACTTCGTATC | AGTAACATTT | TTGTTAATC | TGAACTTTAT | 3120 |
| TAATTGGATA | GCATTTATGT | ATGTTTGGGA | AAAGTTTATG | TATGTCCTGG | ACATGGGATT | 3180 |
| TATCCAGTTG | TGGATATGCT | TGGACCCCTT | GCAATACCTT | AGTAGTGTCT | CAGGGTTCTA | 3240 |
| TGCCCACAGG | ATCTAAGCCT | CCTCCTTTCT | TGTAAGTAAC | TTCTATAATG | TCACACATGC | 3300 |
| AGGGTGACAT | CTCCTAATTC | CAAGGTCAGT | GCTCTTCCTG | CTACCTCCCT | GTGTCTCTCC | 3360 |
| TGTGGGCAC | ATGAATTCAG | CTGTACTGAA | ATGCCAATCA | TTGTCTCATT | TTTTTTGCA | 3420 |
| GTTGATCAGA | CTGAGGCTCC | GATAAAATAA | TTACTCCTCA | GAGATCAGGA | GCTCGGGGAG | 3480 |
| GGGTGGCCTG | TGTCCGGCAT | CATGCAGAAC | AGCATGCGTG | GCTCACTGTA | ACATTCTTC | 3540 |
| AAAGGGGAGT | GCAGTGGACT | GAATGTGTCT | CCCCCCAAAT | TCACATGTTG | AAACCCTAAT | 3600 |
| TCCAATGTGC | TGATATTTGG | AGGTGGGGCC | TGGGGACGT | AATTAGGCCA | TGAGGGTGGA | 3660 |
| GCTCTCCTGA | ATGGATTAG | TGCCCTTCTA | AAAGGGACCC | CAGGGAGCTC | AGTTACTCTT | 3720 |
| TTTCCATGTG | CAAGGATAGG | CGGAGAAGAT | GGCTATCTGC | AACCCTGAAA | GGAGACCTTG | 3780 |
| CCAGAATCTA | ACCATGCTGG | TGTCCTGACT | TCCAGCCTCC | AGAACCATGA | GAAATAAATG | 3840 |
| TCCATTGTTT | CTCAGCCACC | CAGTCTATGG | GACTTGTTA | TAGCAGCCCC | AAGGGACTGT | 3900 |
| GACAGGGAGC | TTGAGAACTG | TGTAAATTTG | AGTTACCAA | ATAACATACA | GCTTAATACT | 3960 |
| GCTTTATTAA | TTCCGTAAGT | CGGAAGTCAT | TAGTCCTGAT | TGATGCCTTG | TGGGGAGGAG | 4020 |
| GGAAACACAC | ACTACTTGTA | ACATAATAGG | AAGATGGAGC | TTTTCCTGGG | CTGTGTCTCT | 4080 |
| AGAGAGTTAT | TTTTAAAAGG | GTGTTTTTGT | TCTTCCAGTC | TTGGGATCAA | AACTTCATAA | 4140 |
| AACTATTTTA | TTATAATGTA | GGTATTAATG | TGGAAAATGA | AAATTCCCTC | TGCTAAAGAA | 4200 |
| GCTTTTTATT | CCATCCTTTT | CCTGAAAAAT | CCAAAAGATA | ATATGATGTC | AGTAACATTA | 4260 |
| AGTGGCAGGA | AGAAGGCAAT | GTTATTATAC | TAAGAATCTT | TTCAGATGAA | TGACAATTAA | 4320 |
| AAAAGAGGAA | GCAGCAGATT | TATCTAATTT | ACAAGATTAA | AAAACTTGGG | AAGATTTTA | 4380 |
| TTTTCATGAG | GGGGTGGGTT | GCTAAACCCG | TGATGAAGTA | TTCAGTTGAC | ATTTTTCATT | 4440 |

-continued

| | | | | | |
|---|---|---|---|---|---|
| CCTTTTTCTT | TGTGGAATTC | ATTATAGTGA | AGCACATTTA | ATCAAAATAC | CAATGTTATC | 4500 |
| AAATGAGGTA | AAATACTCTT | GGTGATTCAG | ATATCACTCT | TTCCTTGGGT | TTTCGTAACC | 4560 |
| GATTTTGATG | ATATAGTTTA | CAAATTAGAG | AGTTGGAGAA | TTAACTTGTT | CCCGTTGTTA | 4620 |
| AACTTAAGGG | AATTTTTAGT | AATGCTTGCC | ACATGTATCC | AGCTGCCCAG | CACTTGTGGC | 4680 |
| CTTGCTGATT | TCTGCTGGCA | AAGGGCTCTG | GGTTTTGGTG | AGTGCCTCTG | TGCTTGGCCT | 4740 |
| CCTATCCCAC | CCAATGGACC | AGGGAGCCAG | GGTTGCTTGG | CCTGCTGCAT | CTCACTGCAC | 4800 |
| CAGGGAGGGA | ACCGTAGCAT | CTCAGTGTCC | CCAAGAGTCG | GGGGAGGCCT | CACTCTGAGT | 4860 |
| GCGTTGGGTA | GAAGTGGGGC | TCTTACCCGA | GTCAGTTCCT | ATGTCTACAG | GGATACTCTA | 4920 |
| AAAAGGATGT | AATGCTGGGA | AGGAAAATGC | TGAAAAACCT | GGAATTAATT | AAGGCGAAAG | 4980 |
| AGTTCAGCAG | AGCATCTTAA | ACACCTTTGC | CAGTGTGGGG | CAGTGCCTCT | TTAAATTCTC | 5040 |
| TATTTAAATT | TCATCTTTAT | TTTTCAGACT | TAGCATATTG | TTAAGCATGC | ATAGATGTCA | 5100 |
| CTTTTGTGAT | TACTTAGCCA | TTTACTTTAC | CCCCTTGAAC | ACTGACATTT | TCCTGACTGC | 5160 |
| CATGCACGTG | ATATATTTCT | TTGGCATCTG | AAAGGTAGT | GTTGAGAAAC | TAATTTATCA | 5220 |
| AGAAGTTAGG | AGGCTGATCC | TTCTTAAGAT | ATGACTTCCT | CACAACTTGT | AAGAGCTTCT | 5280 |
| TAGTAATTAA | GATCAAATTT | GTTCTTTCCG | TCCTGAAATT | GAATGTCCTC | TGGTTTCGTT | 5340 |
| ACTCAGTCCA | TGAATTTGAT | AACTTGCTGT | TTCTTTTCCT | GCAGAATTTA | ATTTCACTTA | 5400 |
| AAGCTTCCTG | CCGCTCCTCC | CCTGCCTGGC | CTTCTACTAG | TTGTGGCCCG | ACAGCAGGTC | 5460 |
| TAATTAGGGA | CTTTTGTACA | AAACTACTGT | TATAATCAAT | GGAAAACCTT | TGAACAACTG | 5520 |
| CATAGAAAAG | AAATTAAGTA | GATTATTTTT | ACGAATCAAG | GGGCAAACTC | AGCTGTGATC | 5580 |
| GTGTGGGGTT | TCAGATAAAC | AGAGGGACAC | ACCAGTGTAT | ATATGAGTCT | TCTCCCACCC | 5640 |
| ACTAAAATCA | ACCAGCTCCA | TGTAAGCATG | TTTTACTTTA | AGATATAATT | GTTATAAAC | 5700 |
| AGTTTCAGA | AAGGAATAAA | TAATGATATT | TTAATATAAT | TTATTTTGAT | ATTTATGTAT | 5760 |
| TTTTATAGTT | ACAGAGTTAA | TTATTTTAA | AGTGCTAGAG | TTTACTATTT | CATTATGAAT | 5820 |
| ATCTATGAAA | GACATATAGT | AACAAAATAA | CTCCTTGTTT | TGAAGAGCAC | ACATGTTAGG | 5880 |
| AAAAGCTGAA | ATGTTTGGGG | ATTGGACCTA | CCCATGAAAA | TACACATATC | TGTCTCCTTT | 5940 |
| CTATAAAAG | TGACTTTTGA | GTCAGTTCAC | CTCGTAGAAG | TTTGAAATAA | AACTTAATCT | 6000 |
| AAAGTAGTGG | TTCCAGGGTT | CCCAGAAGTG | GGCTGAAGTT | TATCTTTGTA | CTGTAACTCT | 6060 |
| CAAGATAAAA | GGTTTGTTGA | AAAATTAGTA | GCCTTGATAA | AATGTCAGGG | GCACATGCAA | 6120 |
| ACTAATTTAG | AAAACAGCTA | TGTTAAGTAT | TTGAGCACAT | TAATGATCTG | AATGCAAATG | 6180 |
| GATATTCCTT | CTTTATTTCT | TCTTCTTCTT | CTTCTTCTTT | TTTTTTTTT | TTTTTTTTG | 6240 |
| AGACAGAGTC | TTGCTCTGTC | ACCCAGGCTG | GAGTGCAGTG | GCACAATCTT | GGCTCACTGC | 6300 |
| AGCCTCCACC | TCCAGGTTTC | AAGCGATTCT | CCTGCTTCAG | CCTCGGAGTA | GCTGTGTGAT | 6360 |
| TACAGGCACG | TGCCACCACG | CCTGGTTAAT | TTTTGTATTT | TTAGTAGAGA | TGGGGTTTCA | 6420 |
| CCATGTTGGC | CAGGCTGGTC | TCAAACTCCT | GACCTCAGGT | GATCCACCCG | CCTCAGCCTC | 6480 |
| CCAAAGTCCT | GGGATTACAG | GCTTGAGTCA | CTGTGCCCGG | CCACTTCTTT | ATTTCTTTAA | 6540 |
| CTTTGCTAAG | TCTTTGCTTA | GAAACACAGG | GATTGCTGTA | CAGTGTGGTT | ACCTGAGAAT | 6600 |
| GATTACTCTC | ATAGTCTTGA | TTCTGGTGAT | CTGTTCTATA | ATCAGTTGTG | CTGATTTTGA | 6660 |
| CTGATCTTCT | CTGAAATTGG | CTGAAATGAC | TAAAGCTTTA | TTGTATTTTG | AGTTTTTTT | 6720 |
| AATCCGGAAT | CTCCCTTCAG | GAGTTTTGTT | AATACCAGCT | ATATTAAAGT | AGAATATGAA | 6780 |
| TATATTGTTT | GCTCCCAGAA | ATACACAATA | AAACCTAGTT | CTTAGAGATT | TTTGCAAATG | 6840 |

| | | | | | |
|---|---|---|---|---|---|
| TTTGTATTGC | TTTTTACTTT | TACTTCCTGA | AGACTTTTTT | TTTTTAAATC | TGGATAGGGA | 6900
| TATGCATGTC | TGTAATACAC | ACATTAGCTA | AGTAAAGCCC | CATAGTGCTT | AAAACAACAA | 6960
| TTGCCATATT | CACACGAAAG | ATCCTGGAGC | CGCCGTAAGG | AGCCAAGGGT | TCCAGGTTTG | 7020
| GTATGTTCAT | GCCCAGTGAC | TGTGGGGCTG | TTAGAGGCAT | CACCTGACAT | TTATTTCTCA | 7080
| ATATCTCTAT | GAAGTAAATT | ATCACTGAAG | ATTCTTCCAG | TTCTCTTATT | CCAAGGAAAA | 7140
| ATATAAGTAT | TATAGCTTTG | ATGGCATTAG | ATTAGTATCT | TTTTCTCAGC | TTACGGAGTT | 7200
| CTGAAAGCGT | TCTCGGTCAA | ATCAGAGCTG | TAAAAAGCTG | TTGGAGGCAA | TGCCACAGGG | 7260
| AGAATGTGCA | TGTGTACATA | TGGATAAATT | AATAGAAACA | GGCGCCTTTC | CCTCCCTCCT | 7320
| CTAACGATTA | AAGACTGGCG | CAGTTCTAAG | ATGAATATAG | ACCATATGGA | GGTACCATGC | 7380
| ATGAATAGGA | GGGGACAGTC | AGACTGTAGG | TTACCTCACA | GACATGCAGA | TTAAAGACA | 7440
| TTGGATGAGA | AAAGGTTGGA | TAACAGCAAT | AAAGAAAAG | ATCCTAGCTG | AGTATGGAGT | 7500
| GCACGCCTGT | AATCCCAGCA | CGTTGGGAAG | CCGAGGCAGG | TGGATCGTTC | GAGTTCAAGA | 7560
| GTTCAAGACC | AGCCTGGGCA | ACATGGCGAA | ATCCCGTCTC | TACAGAAAAT | ACAAAATTA | 7620
| GCCGGGTGTT | GTGGCGTGCA | GCTGTAGCCC | CAGCTACTCC | AGGGAGGCTG | AGGTGGGAGG | 7680
| ATTGCTTGAG | CTCGGGAGGC | CCAGGCAGCA | GTGAGCCAAG | ATTGCACCAC | TGAACTCCAT | 7740
| CCCAGACGAC | AGAATGAGAG | ACCCTGTCTC | AAAAAAATTA | GAAAAAGAT | CCTATGTCTA | 7800
| AGTGAAAGAA | AATGTATGAT | TACATGGGAC | ACGCTGAAAA | CTCTTTGAAA | GAGACAAGAG | 7860
| GTTAAGACCA | AATAGAAAGA | AAGGACTTTA | GAAATTCTTT | AGAGAACAAG | TCAGCATGAC | 7920
| AATATTTATT | CAAACAGAGA | TACTTGCTTG | ACATTGGGAA | ATCCCTGTGA | TAAATGCAGG | 7980
| ATACTGGTGA | AGGCAAGAGA | GTTGCAATGC | AAGGGAATGG | GCGCTCCCCT | TGCTGATGCT | 8040
| GTCTGAAGGG | TCGGTGCCAA | CCAATTAGTG | GAGGTGTAAA | TTTTCTCTGT | GCTTCTTTCA | 8100
| AATGATAGAT | GCCATAGTAA | ATTTAAAATA | TTGATATGAT | AACTGAGCAT | GAATTTTTA | 8160
| ATTCTGCAAT | TAAAAGACTT | TGTTCAAAAT | GCCATTAATT | TTGAGTTTAG | GTGAATAAAG | 8220
| GGAAGCAGAA | TTCTTCTGTC | ATTTTTCCTT | CTCCATGTGA | GTTATCACTT | TTTAGGAATT | 8280
| AAAATAAGTA | CTAACGAGTC | ACCTGTTCTC | TTACCAGTTT | CAGTTGTCTG | CTGGTGATGG | 8340
| GGATGATCTC | TGGAGTCATC | TTTCTTTCTT | TTTAAAATCC | TAACTCTATT | TTATAATGCG | 8400
| TTGGAGTTTT | TCAGACACCA | TCACATGTGG | TCATTTGTTC | ATTCAGCAGA | CACTTCTAGG | 8460
| GCATTTATTA | TGTGTTTTAC | ATGCCGGGCA | CTCTGCAGAG | GTCAACAGAA | TGCCATGGGA | 8520
| GGGTCTCTGT | TTTTGAAGAG | TTTGCAGACT | AATTGTGGAG | GAGGTAGACA | TTAATGAAAC | 8580
| AAACAGATAT | GATTGAATAT | TCCTTTCTGA | GGCAGTCACT | TTTTTTTTCT | TTTTTAATGA | 8640
| GATAGGGACC | AGACCCCGAA | TCTGCCAGCC | CCTTGATCTC | GGACGTCCCA | GCCTCCAGAG | 8700
| CTGTGAGAAA | TACATTTCTG | ATGTTTAGAA | GCTACAAATT | TATGATATTT | GTTAGAGCAG | 8760
| CCCAAACAAA | CTAGGACAGG | TTGTGTGTAT | GAACTGGATT | GTTCTGGGGC | AAGAGTGGAA | 8820
| ACAGCGACTC | GCCAGCCGGG | AGGTGACGTG | GTGTACGATG | CGAGGGCCTT | GGAGGGGTG | 8880
| GGTGCTGGGG | CTGGAGAGGC | CTGGCTGGAG | ATGGGGTGTA | TTTTAGGGGC | AGCATCAGGA | 8940
| AGATGGCGTG | ATAAAGGGTG | GAAGAGGTAG | ATTGACTCCC | CCCAAATGGT | TCTGGTTGCA | 9000
| GTAGCTAGAC | AGGCATGCTG | AGGAGGAGAA | GCAAGATTTT | GGAATGATCA | AGGAAGATTT | 9060
| AGACACCTGA | AGGCTGAGGT | GCCCATGAGC | GCTCCCTGCA | AAGGGTTGGG | TGGTCAGGTG | 9120
| GGTGTATGAG | TTGGGGATTA | GTCCCGACTG | GCTGTAGCAG | TACAGGTATG | TCAGTGCCAG | 9180
| CGACCTGGGT | GGCTGATGAA | GGGAGCATGT | GCAGAGGCAG | TAGGAGTAGC | TGTGGCTGAG | 9240

| | | | | | | |
|---|---|---|---|---|---|---|
| CCCTGAGGGC | TCCAGCGCTT | AAGGTGGTTG | GAGAAAGAAG | GGCCCGTGAG | AAGGAGCACA | 9300 |
| CAGAGCAGTG | TTTTAAGAAA | GAAGGCCTCA | TTTTGGGAGG | CCGAGGCGGG | GGGATCATGA | 9360 |
| GGTCAAGAGA | TCGAGACCAT | CCTGGCCAAC | ATGGTGAAAC | CCATCTCTA | CTAAAAATAC | 9420 |
| AAAAATTAGC | TGGGCGTGTT | GGTGCATGCC | TGTAGTCCCA | GCTACTTGGA | GGCTGAGGCA | 9480 |
| GGAGAATTGC | TTGAAACTGG | GAGGCGGAGG | TTGCAGTGAG | CCGAGATCGC | GCCATTGCAC | 9540 |
| TCCAGCCTGG | CAACAGAGTG | AGCTTTGTCT | AAAAAAAAA | AAAAAAAAA | AGAAGGCGGG | 9600 |
| CTTGTCAGCT | GTATCGGAGG | CTGCCAAGAG | GCCTAAGATT | AAAAGTGTTC | ATGGGGTTCA | 9660 |
| GCAACGTGGA | GGTCAGAGGT | GATATTGCCA | AGTACAGTTT | CAGCCAAGTA | CAGTTTCAGC | 9720 |
| GGAGCAATAG | GGTTGGAAGC | CACATTGGAG | CCTCTTGAAG | GAGAACAGAG | GGTGAGACAA | 9780 |
| TGGGGACAGC | TTTATTTAGA | TCGGGCTTTG | GGATGTGTGG | CTGAGAAGAG | AGCAGAGAAG | 9840 |
| TGGGGTGGTG | GCTGGAATGG | AGATAAGGCC | ACGGGAAAGG | ATTGCATTGT | TTGTAGGATA | 9900 |
| GGAGAATCTG | GTTTTGGCTT | TGGTTTTTGC | TTTTCTGTAG | CAGACATTTG | TTTGTTGATG | 9960 |
| GGAATAGTCC | AAGACAGAGA | GAGTGAGATA | GAGATTTCTG | GAACAGAGGC | AAGGTGCTCA | 10020 |
| AGGCTGTGAG | GATCGGTCTC | TCAGACACCC | TGGTTGATAA | TAAGAGGAAG | GACTGAGAGG | 10080 |
| GGAGGTGGGA | GGACAGCAGA | CACAGGGTCC | TGGAGCGAAA | GGCAGAGTGT | GATCAGTTGC | 10140 |
| ACCATTCCGG | TGGAGGAAGC | AGGGTCATCG | GTTGAGAGAG | CTGGGAGTTG | GAGCTTGGAT | 10200 |
| GCCGGGAGAA | GAGAAGAGCT | GATTGTGTGG | GGTGGGAGAA | GAATGTCCTA | GGAATGTAGG | 10260 |
| GCAGTGTCAG | GAGCTCACAT | CTTATCTGAG | AATCTCGAGT | TGGGCGGTTG | CTTCCCATTT | 10320 |
| TCTACCTGCA | GACCCAGGAT | CAGTGCGCTG | CCTGAGGCAG | GCCAGGGAGA | GCTGGAATTA | 10380 |
| ATTAGAACAC | ACATCCCAGC | TCCTCTTCCA | GTGCCCAGTG | CTCAGGCCCG | GTTCCCTCT | 10440 |
| AAACGCTATT | AACACACAAA | GGAGGCTTTT | AAGCTCCATC | ACAGTACTAT | CAGCGCTGAT | 10500 |
| TAGCGCTCTG | TTTCTCTTGG | TGCTGTTGTC | ACGCATTTTA | GGCATCACGT | GTGCATTTCA | 10560 |
| CATGAACAGT | GGGAAGGGAG | TTGGCATGGC | CTACCGTGGA | TGCAGTACAG | CTATTTCCAC | 10620 |
| ATCCTCCTCC | TCCTGACCTG | ATTGTGTGCC | CTTAGCCCAT | AGGAGGCAGT | GTAATTAGAG | 10680 |
| TTCTGGGGGC | TTTATTACCA | ATAATGGCCT | TACCACAGTC | AGAAATCTCT | TTAGCCCTGA | 10740 |
| GCACTACCAT | TGGGGCTAAG | TGGCTCCCCT | GGGTGCCGTG | AGTTGTCATC | CGCAGCTTTA | 10800 |
| CGAAGAGGCA | TTGAGGAAGG | GGGCAGGGAT | GGGGAGCAGA | GTGGGAGAGA | GGGAAAAAGA | 10860 |
| AATGGGTATT | CTCACAGGCA | GGCTGGATTG | GCAGGCCAG | GACAGCCTGG | TCTCAGGTGG | 10920 |
| GCACACGTGG | GAGAGGATGG | GAAGCACTCA | CATGTAGCAA | GTAGCTTGTC | TGTGCTGTGC | 10980 |
| TCTTGACAGA | TGTTAGTCTT | TCTAACCGTT | CTTGGAGAGG | GACTTTCTC | TCTATTTCTT | 11040 |
| AGGTCCGGAG | GCTGAGGCTG | AAGAAGATGC | TTGACTGGTA | GGTTGTGGAC | AGTGTGTGAG | 11100 |
| GACATGGTAG | GGAGGAAGCA | GAGAAGACAG | GCAGAACCAG | GGGTCTCCAA | GACCCCTGAG | 11160 |
| TGCATTGTTG | CAGGAGCGGA | GACGGAAGTT | CTTGCCTCAG | CTTTCAGGGC | CCTGGGCTGT | 11220 |
| GGGCAGGCGG | ATGGGCACCC | TGGGTGTGGA | GGCTTCCCTC | AGAGCCTGCA | GGATGGGCTG | 11280 |
| CCTTTTACGT | GAGTGACCCA | CCACTTTCTC | CCCAGACCTT | GGTAGAATTC | CTTTGCGCTG | 11340 |
| TCATTTTCTT | CTAGCAGAGC | CTCCTCTCTG | GGCACAGGGT | GGAAACAGAA | CAGAGCCCAC | 11400 |
| ACATTTTCCA | CGCATGCGGC | GGGTTTCTCC | ACATCACCCC | CGTTTCTCGT | CTTTATTTTC | 11460 |
| ACACACACAC | TTACACTGTC | ATGCCTATCA | GGTGGAATCA | TGTGTCCCTC | CATGGCGGGA | 11520 |
| GGGCTCAGTT | ACTTTATCTT | CTGAGTAGAA | AGGCCACACT | CTGCCTGGGG | CTGGGCTGGG | 11580 |
| GGCAGGAGTG | TCTGGATGCC | AAGGACATGG | TAGGCTGTCG | GGTGCAGCGT | GATCGGGGAG | 11640 |

```
GCAGAAGCGC TGTCACTTGT TGTCTCTGAT CAGGAAGACC TGGTTCCTGC CAGCCAGTGT    11700
CTTTCTTAGG AAACAGGTCC TGTTCTGAGT ACTGGTGACA AAGTCCCCAT TTGCAGAGTT    11760
CTTTGGAGTT CACACAGCAT TTTCCTACTG TGTCCCTCAC TTGCTGTTCG TGTGACCCTG    11820
TGAGATGGGA AGGGGCGGGT GTCGTTATTC CTATTCGTAG CTGAGAGAGG CTGGAACTTG    11880
AACAGGGTAT TACCTTTGTG TAGGCACATC CTAGGATTTA AATCCCTTTG TCCTGAAAAA    11940
ACATTTGTAA TCCACATACA TTTTTCTACA GAAACAATGT TACTTGAAGA TTCAGTTCCC    12000
CTTGCACCTG CGAGCAGTGC CTAGAACCCT CGTTTTCTGG ATTTTCTCAG CACTCCTTCA    12060
GCAGTCCTAC TGTGTTGCTT TAGCTTGCAC TCGGGCCGCT GCTGATTTCC ATGCTGGGGC    12120
ATCGCAGCCC AGCTGGTGTG AGCTCTGCAG GGACCAGACC CACCTCCATC CCGCAGCCCA    12180
CACACCCAGC CCTGTTAGCT CTCCACCCAG TGCAGGCCAG TTTGCAACCA GAACTTACCA    12240
GAACATACCT GGGAAACTGC GAAAGTTTTA AACTGTTTTA TTTTCTTGCT CCAGTCCTGT    12300
TACTAAGGGC TGCTCCCCTG GGTGGGGGAC AGGGCTCTGT CTGAGCAGGC TTAGAGGGAC    12360
ATAGGCTTTG GAGCAGTCCA GCAGGCTGGC AGGAGGAAGA CAGGGCCTTA GCCAGGAGAG    12420
GGGCGGGGAG CAAGAGGGGC TTGTCTGGTG GAACTATCTT AGAGAAGTGA TACCTGTTGA    12480
TTTCTATATG GTGCTCCCTT CCCCAGTTCC ACCTTTATTT CAAATCATTT GAAAACCTTG    12540
ATAATGAGCC AGATTGCTGC TTTACTAATA GGAACTTCAT GCAGGAGAGA TAAGATAGAG    12600
AGGTGACATT ATTTGGGACC AAATTCTAGA AATCTTTGCT TTAGATTTTG GGGAAGCCAT    12660
AATTGGGAAC ACTTCATAAG CTTTTGGGAG AGTGTACTTG GTGGGGGTTG TGGGGGGCTT    12720
AACTGTCAGC GGCTATTCCG TTGTTAAATT ATTGACGTGC AGGATAGGGA CTGCGGAGGC    12780
TGGCAGTGAC ATATGAGGCC CTGTCAGGAT ATCTTTCAAT AATTAAGAAA CAAGTAGTTG    12840
AAATTCCATT TTAGTTCCAG AAGCTGTGAA GCAGTTCCAT AAATGGATCA GTTAGAGGAG    12900
TAAGTGTGTA CCCCATCCCT CAGCGGAAGT TTCCATCAGG CATCTGTGGG AGTGGGGGCC    12960
GGGGCAGGGG TGCAGGTGCT CCCAGAGACA ACATGTCCAG GTTAGCAAC TCTGATAACT    13020
ATAGGACCCC AGAAGTAAAA GCACTCAGGC CCTAACTTCA GGAAGAAATG ACAAAAGCT    13080
TTGTCATCAG AATGGAAGTA GAAAATCCTG TAAATTACTG AGTTTTTTTT TTTTTTTTA    13140
ATGCACAGGT CAACCTTGAA CTTGGGTATG CCATTTCATG TCACTTGTTA ATTGCAGGGT    13200
GGGAACCCAG TAGAAATAAT AGAGGGTGAT GCTTCCCACC TTTTCATTCC AGAAGGCCAT    13260
GAGCAGACGC TTCTTAGCTC GAGTCCTGAC CCTTGTCTTG TCAGTGAACA GAACTGTCCG    13320
TGCTCTGAAC GGCTCAGCCT GGGGTGGCGG CAGAAGGCGT TGCAGGTCTG TTCTCAGTGG    13380
CAGCAGGCAC TCCATGCCTG GCCTTCTGAC CCCGGTCCTA GCGGGACGCA CCACACCAGG    13440
CTGCCACCTG TTCAGGTCAG CTTTGGCAGA ACAACCCTCA GGTCTAAGGA CATCGTTTTC    13500
TTTAAGGAAA ATCCTGTGTC ACTAAAAATG AGGGATTTTT AAGCAACCTG GAGAGTTCAG    13560
AACTAGAACT AGAGTTCAGA ACTAGATCAG AACCTTCATT TTCCTGACTC CAAATTTTCT    13620
CAGGCCCCAG TAGTTCCTGT CACATCTCCA TAGCAGATGA AGATCAGTTG AGGGTAGAAT    13680
AACACTATCA CTGCTAAATT ATTTAGGCAG CAATTAGAAT TTGTTCAGCA TTATTTAGGG    13740
TTTTTAAACA AACCTATCTG AGTAACCTTA TAATACTACC GTCTAAAATA GATATTGTAT    13800
CAGTCTTATA TCAGATGAGG TGAAAGTCAC ATCTATAAAA CGCTGAACTC TTAAATCTAA    13860
CCAGGGATGG AATATATCCT GTTAATTTGT CAAACTTCTA GAGAACCGCC TACATGAGAC    13920
AGTAAGGATT AATCAAGCCC TACTAAGAGA GAATTTGAAA AATACAGTTT TCTAATTATA    13980
CAGTCTCTTC TCCATGGTCC AAGGTTAATG CAGTTCTGAA TTCTGACAGT TAGTAATAGA    14040
```

```
AAAGAAAAAA  AAAAAAACCA  AAGCATATGA  ATTGTCTTAT  AATTACCTGA  AACAGAAAGT    14100
CTCTTCTGGC  AATCAAGGCC  TTCTAAGCAT  TAATCTGATA  TTTTCAGCAT  TTGATTCTTT    14160
TCCTTTTAAA  CAAGGTTGGG  AATAACTGGA  GGGTTGTGTG  TCACTCTTTG  TGCTTATCAA    14220
ATATATGTAC  TGTTTGCAGA  TTTATTTTGC  TTATTGCTTA  GCTGTAGATG  TGTAATTCTA    14280
GGTTGAACAT  TTTATCTTTT  TTTCTTTTTT  TTTTACAAT   TTAGACTAAC  TTATGAATAC    14340
TTCCTAGACA  CTGTATCTTT  GAAATACTTG  ATCCTTATTC  CTACTACGAA  TATAAAAACT    14400
AACAATTACT  TCTTGGTTAG  TTTTGGTTAG  TTGTAGCTCT  TGCTGCAGTT  CATCCAGGCA    14460
ACACAACAAA  AATGTGCACT  CTAGGGAAAG  GTAAATTTAT  TCCTTCATTT  ATTGCTGTCA    14520
AATATCTGTG  GAATGTTTAT  TGTACAGGTT  GAGCATGCCA  AATCCAAAAA  TCAAAATCTG    14580
AAACTTTTTT  TTTTTTCTGA  GATGGGGTCT  TGCTCTGTTG  CCCAGACTGG  AGTACAGTGG    14640
TGCAAACACA  GCTCACTGCA  GCCTTGACCT  CCTGGGCTCA  AGCAGTCCTC  CCACCTCAGC    14700
CTCCCAAGTA  GCTAGGACTA  CAGGTGCACG  CCACCATACC  TGGCTAAGTT  TTTTTATTTT    14760
CAGTAGAGAT  GAGCTGTCAC  TATGTTGCCT  AAGCTGTTCT  TGAACTCTTG  AGCTCAAACG    14820
ATCTCCCCCA  CTTGGCCTCC  CAAAGTGCTG  GGATTACAGG  CATGAACTAC  TGCACCTGGC    14880
CCAAAATCTG  AAACCTTTTG  CACACCAGCA  TGACACTTGA  AGGAAATGCT  CATGGAGCAC    14940
TCTGGATTTC  AAATGTTTGG  ATTTGGGATG  CTCACCTGGT  AAGTATAATG  CAAACATTTT    15000
AAAATCTGAA  ATCTGAAACA  ATTCTGCTCC  TAAGCATTTT  GGATAAGAGA  TATTTAACCC    15060
ATAGAGGAAA  GGTACATGGA  AGCCCCAGAC  CACCCAAAAG  AAAAGGCCTG  GGGAGAAGAT    15120
GGGCAGTTAT  GGCTAGACAC  CAGATTCAG   GTTTACAGA   TGGATCTGGC  ATCTGAGATC    15180
TATGAACAGA  TGGATTCTTA  AGGTCAGTGA  CTGGCCGGGC  GCGGTGGCTC  ATGCCTGTAA    15240
TCCCAGCACT  TTTGGAGGCC  GAGGCAGGTG  GATCACCTGA  GGTCAGGAGT  TCCAGACCAG    15300
CCTGGCCAAC  ATAGCGAAAC  CCTGTTTCTA  CTAAAAATAC  AAGAATTAGC  TGGGCATGGT    15360
GACGGGTGCC  TGTAATCCCA  GCTACTCGGG  AGGCTGAGGC  AGGAGAATCA  TCGCTTGAAA    15420
CTGGTAGGCA  GAGGTTGCAG  TGAGCCGAGA  TCACGTCATT  GCACTCCAGC  CTGGACAACA    15480
AGAGCAAAAC  TCCATCTAAA  AAAAAAAGAA  AAAGAAAAAA  AAGGGCAGTG  ACTATGGGAG    15540
AAAAATCAAA  GACCAATATT  TTACCTTGGG  AAGTGCCCAC  AAAGGCAGGA  AAAATAAAAG    15600
GACCTACAGA  AAAGTAAAGC  AGAAAGAGAA  CACAAGTGTA  TGGTGGTCCT  GAGAGGTTTT    15660
AGAATAGAGA  GGAGTCCAAA  GAGAGCAGGT  GAATCAAAAG  GTTCCAGGCC  AGAAGAGACC    15720
TTGGGTTTTC  ATGATGACGA  GACCCTCCTG  TGGCCTGTGG  AGCTGGCTCT  CATCAGGTCA    15780
TCAGAGCCAA  CTGTGCGCAT  TGCTTCCCAA  GTACACGTCA  TGTTGGGAGT  GGGAGATTGG    15840
CTGTGTGAAA  AAATGTCTAC  ACCACGGAAA  TTGGCAGATA  TATGGTGACC  CAGCAAACAC    15900
AGTTGACACC  TGAAACATAA  TTTTTAGGAA  TAGTATTTAA  CCTTGTATGC  GGGATCCATT    15960
CTGACCTCTA  TCCTTCCCTT  CTTACCTATT  TCATTAAAAC  AGAAGAAAAA  GCTGGTGTAA    16020
CTCATTGAAC  TGATTTCATG  ACCTGCAGTT  TGAAAACAT   TATTTAGAG   AAAACTGGGG    16080
ATTATGTATG  CCTTACAAAG  TCAGAAGACA  ATTATTTAA   AAATAAATTA  TAGTAACAAT    16140
TGTAGATAGG  ATGATTTCAT  CTTGAAGGA   GGAAAAAAG   AATCCTAAAA  GGCTGACAAG    16200
ATGACCTCTC  TAGACTAAGG  ACTAAGTATG  CATGCTTACA  GGAGAAGAAA  AACGAGCAGA    16260
GAGAAGCGGG  AGCCCTCAGA  GATGGAGGGA  GGAAGGGGCT  GGGAGCACGG  CCTTGTGTTT    16320
GCCTGGGGAG  AGGAGGCCGT  GTTTTGATAG  TGAAAGCTTG  TTTTAGAGAA  AGTCACCTGT    16380
TCTGGAGGAT  TGAGGAATGA  AACTGGAAAC  CTTAGGAAAA  AAGCAAAGAC  ATCGGATGTA    16440
```

```
CTTGGTATTT TTTAAATTGC TTTTATTTAG TTAGCTGGAA ATGCACTTTC TCAGATCCAC     16500
TGTCACTCCT GCAAATTACA AGAGCGCTCA GCCACCCTGT CGAAGGTCAT CCGGCTTCCA     16560
AGCAGCAAAT TGGACCTTGA GCCCTCGTGC TGCCCTTGTT GCAAAGCTCT TTGTCCACAC     16620
TCGCTGGCAG AGGTGGAGAG TACAGAGGGG AGGATGCTTG GCCTGTGGTG GTCTGGCCAG     16680
CCAGGGCAGG CATGAGCTCG TCACAGGCCA GGCAGTCATC GAGTGCTCTT TGTGGCCTGA     16740
AGTGGATTTG GCAGGTGCCT GTTATTTGAT CAGTGTCGAT GGCCAGTCGA CACAAGTAAA     16800
TGAATCCCCA AACTTACTC TGACCCACCT GCTTTAAACA AATTGGAGGA AGTCATCAAG      16860
TTAGTTTCCC TAGTTTCCTC TCTGAGGACA GTCTGGGGGC TGAGGCTGGC TGAGTCCTGT     16920
CTCCTCAGGA CAGGCCCAAA AGGAGGTACA GGGCGGCCTG GGGACAGCA AGGTTCAGAG      16980
TTTCAGGGCT ATGGAGATCC TGGAGCTGAT AGACGAGTGT CAGCCACAAA GGTGAAGCTG     17040
GATTTCAGGA CCACAACAGG CGGCACGTGG GAGTTACGAA GGGGCAGGG CTGGGTTGCG      17100
GCCTCAGGTG CTCCTCTGGG TTGGGGCTTC TCTCCTCAGC CCCGCAGGTG CGTCGGGCAA     17160
GCCTGTGATC ATAAGACAGG GCTGAGGGGG TCTGGGGAAG GGTACGGGAA CCAGCAAGAG     17220
AGACCAGGGT GGGGCTGATC TTACACCCTC CACCGAACAC TTGAGTTTCC TGCTTGTCAG     17280
TGTCACTTTT GCGTATGTGG GATTTTGGAT TGTTCCTTTT AGAGTCTCAT GTGTACCCGA     17340
CACACTACTG TTCATATTGC CCAGTAGCTT TATATATATG TAAATATATA TATATATA      17400
TGGGTGCTAA ATATTTATCA AATGAATAAA GGAGGAAATG CAGATTCCAG TTATTCATGG     17460
TGATGTTGGG AAGTACTGAA AGTCCTCTTA AATTCAAATA TCAGAAATAT GCTCTCCCAT     17520
CTAATAAATA CTTTTGATG GTGCTGGTAT TAATATTCAG ATATGATATA TATTTAATAT      17580
TTATTTTTAA TATTAATATT CAGATATATA TATTTTTAA CAAGAAGCTT TACATTCTTC      17640
ATCTTGTGAT TTTTGGTTA AAAGAAAGGA AGTCTGTTTA CTAAATCGCT GTTGCATGTA      17700
GTTTCTATAA ATCGCCCTCT GTACACAGGG ATGTCAGATG CTGCCCAAGA GAATCTGTTT     17760
CATATGGTAA TTTTCACTAA TGAATCCAGA CCTATACTGT TAAATTTTGC CCCAAACTGC     17820
CTGGGATGAA GTAGAGGAAG CTCATGGCAG TGAGCGTGAC AGTTCTTAGA GGACGCTATC     17880
ATAGTGTTTC ATAACAGATG CAGAGGCTCT GCAGTTCTGA ATATTAATAC CAGCACCATC     17940
CAAAAGTATT TATTAGATGG GAGAGCATAT TTCTGATATT TGAATTTAAG AGGACTTCCA     18000
GTACTTCCGA ACGTCACCAT CAATAATTGG AATCTGCATT TCCTCCTTTA TTCATTCGAT    18060
AAATATTTAA CACCCATTAT GTTCATGGCA TCACATTAGA CTCTGGGGGA GTTACAAAGA     18120
ACCTAGGCTG CTCTGCCTTC AAGGGGGAAA TAAAAGAAAC AATTACATGT AATTGTTTTT     18180
AACACCAAGC AGCGTGAAAC CCAGCTCTGG AGCAGCCTGG TCACAAGGGG GAGAAGAGGT    18240
CACGGGAGCC CCTCCAAGGC CAGCGCACAT GTGGCCATAC CTTGTGCCTT CCCAAGCCCG    18300
GGCCCTCGCA CCCTTCTCTT GTCTTTCCTT GTCCTCCCAT GCCGTCAGGG TTTATGAGAC    18360
CTGCAAGTCT CGGGGCATGG CTCTGGTCAC TCTGGGCAGC GAAGATGATT CTCTGATGGG    18420
CTGTGGTCAG TGAAGCACAG CTTGTTTGCC TCTTTTGATT TTCCTGCAAT GCCAGGAGAG    18480
ATTGCTCAGT TTTAGGCAGG ACTGAGATCT CCTAAAACAT GGAATTTGTA GACAAAAATG    18540
AATACTTCCT AACATTTCCT GAGAGAGCTT TTGGTCAGCC TTATGCCTGC AACATTGCAT    18600
TGCTGCTGGG GGACCAGGCA CACAGAGGTA GCTGCAGCTG CACCCGAACA CGAGAGGGTG    18660
GCTGAGGAGA GTGGCCAGGC CTTCATCTCT CTGACCCAGA GTACGTGCTC AGTAAATGAT    18720
CATCGATGAA GCAAGTGAGT CGGGACTGAA ATGTATGAGC GCCATAAGTT TAGGCCACTG    18780
CTCATTTAAG GCCTCAGAAC TCCTGGAAGT GTTACGTGTA GAAGGTTGGC AGGCTGGAGA    18840
```

| | | | | | | |
|---|---|---|---|---|---|---|
| GGGTAGGGGA | GACCTTGAAG | ATTCCCATAT | TTATATTCTA | GGTGGCTTGT | GTGATGTGGC | 18900 |
| CATGGCCGGA | TGTCATTCAT | TAACTCGTTT | GACAAATATT | TATTTAGCA | CTTGTGTGCA | 18960 |
| TAGCATGTGC | TGGGAATACC | AGGGGAGCCA | GAAGGCAGTG | CTTCCGGAAC | TTGTCTGCAC | 19020 |
| GTTGGAATCA | CCCGGGGAAT | TGCTTACAAA | TTCAAGCCCA | AGCCACAGCC | CAGGCCATCA | 19080 |
| CACTCTGCAG | GCACAGGGCA | CAGATCTCTG | TATTTTGGAA | GCGCCTAAGG | GTGTTCTGAT | 19140 |
| ATCAGAGAGG | TTTGCAAGTC | ACGGCTGTTA | GGATTTATAA | TAGAGTTTTA | GATAACACAC | 19200 |
| CCAGGAAAAT | TCAGTAACGA | TACAAGACGG | CCATCCAGAA | ACCTCCTGGG | CAGGATGAGG | 19260 |
| GAGTCAAACC | CAGGTGTGTG | CTGTGGGCAC | CACTCATTCC | CCCTCAAGGA | GGATGTCGCC | 19320 |
| TGTGGATTAG | GGAGCGGGAG | CATCTAGGCA | AACTGGACCT | CTGGGGTGTG | TGTTGCTTTG | 19380 |
| CCAGGTTCGA | GAGAGGGAGG | AAGGGGATCC | CCTTGACTCT | GAACTCAGGC | AGGTCCGGAT | 19440 |
| GTGACCCGGG | ATCATGGGTG | GAATGCACTG | GTCTATCAAG | AGCTCAACTA | GTCATTGCCA | 19500 |
| TTTAAGTGGA | TGAATGTTTT | TCTTATAAAA | GACAGACTGG | GCTGGGCATG | GTGGCCCACA | 19560 |
| CCTGTAATCC | CACAGCTTTG | GGAGGCCAAG | ATGGGAAGAT | CACTTACGGC | CAGGATTTCA | 19620 |
| AGACCAGCCT | GGGCAACATA | GTGAGACTCC | ATCTCTACAA | AAGATACAAA | AAATTAGCTG | 19680 |
| GGCTTGGTGG | CACGTCTGTA | CTCCCAGCTA | CTTGGAAGGC | TGAGTTGGGA | GGATCACTTG | 19740 |
| AGCCCAGGAG | CTCGAGGCTG | CAGTGAGATA | TGATCATGCC | GCTGCACTCT | GGGCAACAGA | 19800 |
| ACGAGACCCA | GTCTGGCTGC | TGGCGTTTTT | CCTTGTGCGT | ATGTGGGCTG | AGCACGATGT | 19860 |
| GGTAAAGCAG | ATCCCTCAGG | ATGGACACGC | TCAGCTTCGT | CACTTGTTGA | TTCTCTTGCT | 19920 |
| CTTAAAATCC | CCTAGCCCTC | TTAACAGCCA | CGGTGAACTT | CCCCATGTGT | GCGTGTCAGC | 19980 |
| ACACCAATGA | GCCAGCTCAG | GTGGCACTTT | CATGCCCAG | GGTCTTGTGG | AGCCGTGAAG | 20040 |
| CGGACGTGCG | CTTAGGGTGG | GGAAGGCACT | TGACCTCGGC | CGTCCTGGCC | GCTCTAGGTG | 20100 |
| CCTTCAGGCC | TCACTGCTCA | TCAGCAACCA | GCCAGACCAC | GTGGGCCTCA | TTTGGTATTC | 20160 |
| TTAGGACTTG | CCATTTCTAA | TCAATGTTTT | TACTTGAGTC | TGTTATATGT | TATTTCAGAG | 20220 |
| GGGGAATGG | AATGTGTTAA | CACTTAGTAA | ATTCTTCATG | AGCTGCAACC | AAAGTTTTC | 20280 |
| TTTCTTTCCC | TTTCAACCCA | CAG | | | | 20303 |

( 2 ) INFORMATION FOR SEQ ID NO:7:

( i ) SEQUENCE CHARACTERISTICS:
        ( A ) LENGTH: 117 base pairs
        ( B ) TYPE: nucleic acid
        ( C ) STRANDEDNESS: double
        ( D ) TOPOLOGY: linear ( i i ) MOLECULE TYPE: DNA (genomic)

( v i i i ) POSITION IN GENOME:
        ( A ) CHROMOSOME/SEGMENT: 4q35

( x ) PUBLICATION INFORMATION:
        ( A ) AUTHORS: Weiner, Karen X.B.
                Weiner, Russell S.
                Maley, Frank
                Maley, Gladys F.
        ( B ) TITLE: Primary Structure of Human
                Deoxycytidylate Deaminase and Overexpression of Its
                Functional Protein in Escherichia coli
        ( C ) JOURNAL: J. Biol. Chem.
        ( D ) VOLUME: 268
        ( E ) ISSUE: 17
        ( F ) PAGES: 12983-12989
        ( G ) DATE: June 15-1993

( x i ) SEQUENCE DESCRIPTION: SEQ ID NO:7:

|  |  |  |  |  |  |  |
|---|---|---|---|---|---|---|
| TGTGCCATGC | GGAGCTGAAT | GCCATCATGA | ACAAAAATTC | GACCGATGTG | AAAGGCTGTA | 60 |
| GTATGTATGT | TGCCTTGTTC | CCTTGTAATG | AATGCGCTAA | GCTCATCATC | CAGGCAG | 117 |

( 2 ) INFORMATION FOR SEQ ID NO:8:

( i ) SEQUENCE CHARACTERISTICS:
        ( A ) LENGTH: 1357 base pairs
        ( B ) TYPE: nucleic acid
        ( C ) STRANDEDNESS: double
        ( D ) TOPOLOGY: linear ( i i ) MOLECULE TYPE: DNA (genomic)

( v i i i ) POSITION IN GENOME:
        ( A ) CHROMOSOME/SEGMENT: 4q35

( x i ) SEQUENCE DESCRIPTION: SEQ ID NO:8:

|  |  |  |  |  |  |  |
|---|---|---|---|---|---|---|
| GTAGGAACCG | GGTCTTTCCA | TTTGTCACAT | TGCATTGCT | GCCTGCTCGT | CAGTAGCTCA | 60 |
| TTGCTGATGT | GTTTGATCTT | AAATTGCTAT | TGTTTAGATC | TAAATTAATT | GCACTATCAG | 120 |
| CTTTGCAAGA | TATTTCCCGT | GTTTTGTTTT | TGAATGGTGC | CAGGTATTCT | AAGACTAATT | 180 |
| GCATCCTCTG | TGATTCTTAG | CATGTTTTTA | ATTTAGTTTG | CAACTTCTTA | AACTGCAAGC | 240 |
| TGCCAAAAAA | CAACACAGGC | ATTGCATATA | ATTACTGTCA | ATTTACTGTT | CTCTGACATA | 300 |
| TGTGCATAGA | TTTGGGGGAG | GGAAGAAATG | AACTTCTGTC | AGAAACAAGG | TCAGCTGGGA | 360 |
| GTCTGTATAT | GAAATTTTAA | TTTGTATCTA | ATACATGGTA | GATATTTGAG | GATCTCAACA | 420 |
| TACCTTGGCA | TATAAATGTC | ATAAGACCCA | AATGGCACTA | CCTTCAGGTT | TTCTTATTTT | 480 |
| ACGGTTCCCA | TAAATCTACA | CCATTGTATT | CTGAATATTT | CGCCTTTTC | AAACTGTCAC | 540 |
| ATCTAAGATT | CAGCTACACT | TTGTCTCCAT | AAAACTCTCG | GCTGGAGATT | TAAAGACTTA | 600 |
| CCATGTTTAG | CCAAATGTGT | GGTTTGAAGG | GGCCGTTTAT | CACCAGTCCT | GTGGATCTCA | 660 |
| GAGCAGAAGC | GGCCTGCTGG | TACTGAGGAG | TCGCGTGGGC | TCCCTCGTGT | CGCCGTCACC | 720 |
| GTTCCTGGGA | AGCTCTCCTC | GCGGTGCCCA | GGTGTGGAGG | CGGTGGCAGC | CTGTGGGCCG | 780 |
| AGCAGTCCGG | GCCCCACACT | GCAGCCTCCT | CTGCCTTCAG | AGGCTGATGG | AGCAGCGGCC | 840 |
| TTCAGTGCGG | GGCCCTTGGG | ATTCCTGGCT | GCCGAGTTAG | CGCTGCCTGC | TGAGATCAGG | 900 |
| ACAAGAAAAC | AGATCTGCCC | TCTGTAGAGC | TGGTTTGAAG | TGGTCTGCAA | AGCCATGCTG | 960 |
| GGAAGCACAG | TGGTGCCCAC | CTCTGAATTT | GCCAGCAGCC | CCCACTCCCT | CCATTAGTCC | 1020 |
| TCCCACTAGT | AAGAGAAGCT | ACCTTGTGAT | ACTGCCTTGA | TTACCTGTAG | TAAGGGAAAT | 1080 |
| TGGTTAATCG | GATCAAGGCT | TGACTACTTG | ACATGTTTC | CCTTTGCATT | TGTTTAAAAA | 1140 |
| AAAAATCCAT | AAAGACTGGA | GGGAAGATTA | GATAGAATCC | ACCCTCTGCT | GTATTAGAAA | 1200 |
| GCAGCAGATA | TGTATTTCAG | TGACTGGACA | CTGTCTGCAA | GCACACTCAG | AAAAGGTCAT | 1260 |
| TAATCATAGA | CGCTGAAAGT | GCTCCAGCTC | GTTCCGCCTG | TCTTTTGCAG | CATCTGTAGG | 1320 |
| TGCGTACACT | AAGGGAGCTC | CCATTGTTAC | CTTACAG |  |  | 1357 |

( 2 ) INFORMATION FOR SEQ ID NO:9:

( i ) SEQUENCE CHARACTERISTICS:
        ( A ) LENGTH: 97 base pairs
        ( B ) TYPE: nucleic acid
        ( C ) STRANDEDNESS: double
        ( D ) TOPOLOGY: linear ( i i ) MOLECULE TYPE: DNA (genomic)

( v i i i ) POSITION IN GENOME:
        ( A ) CHROMOSOME/SEGMENT: 4q35

( x ) PUBLICATION INFORMATION:
- ( A ) AUTHORS: Weiner, Karen X.B.
  - Weiner, Russell S.
  - Maley, Frank
  - Maley, Gladys F.
- ( B ) TITLE: Primary Structure of Human Deoxycytidylate Deaminase and Overexpression of Its Functional Protein in Escherichia coli
- ( C ) JOURNAL: J. Biol. Chem.
- ( D ) VOLUME: 268
- ( E ) ISSUE: 17
- ( F ) PAGES: 12983-12989
- ( G ) DATE: June 15-1993

( x i ) SEQUENCE DESCRIPTION: SEQ ID NO:9:

| | | | | | |
|---|---|---|---|---|---|
| GTATAAAAGA | AGTGATTTTC | ATGTCTGATA | AATACCATGA | TAGTGACGAG | GCAACTGCTG | 60
| CGAGGCTCCT | GTTTAATATG | GCCGGGGTGA | CATTCCG | | | 97

( 2 ) INFORMATION FOR SEQ ID NO:10:

- ( i ) SEQUENCE CHARACTERISTICS:
  - ( A ) LENGTH: 1554 base pairs
  - ( B ) TYPE: nucleic acid
  - ( C ) STRANDEDNESS: double
  - ( D ) TOPOLOGY: linear

- ( i i ) MOLECULE TYPE: DNA (genomic)

- ( v i i i ) POSITION IN GENOME:
  - ( A ) CHROMOSOME/SEGMENT: 4q35

- ( x i ) SEQUENCE DESCRIPTION: SEQ ID NO:10:

| | | | | | |
|---|---|---|---|---|---|
| GTAAGTGGGG | AGAATGCGGG | CGGGGGGACG | GGGTAGGGTG | AAGGCTGATG | AAGAGATGTA | 60
| TTTGACCTTG | TCTCCTCCTT | GTGATGCCTG | ACTTCCACAC | TTGGAGGTGT | CTTTAGAAAT | 120
| GCAAGGGCAT | AAGAATTTAA | AGACTATTAT | AGGGGTAGAT | ATTTAAGAGC | AGTGACAGGA | 180
| AAATCTGAAG | ACCATTTGTT | TAATGATTGT | ACTTTAATTT | CAGTAACTTT | CCGGGGTAAT | 240
| TAGACTAATT | ATTCAAGTAC | TGAGAAGTTT | AAACATTCAC | AAGTTTTATA | ATAGGAACGC | 300
| CAAACCTTGG | TGAATTTTGC | AAATGTAACA | ACTTTGGCAT | AGAAAATTTA | GGATGAAAGT | 360
| AGCCTGCCAG | ATTGAAACAT | TGGGGATTCT | CTCTTTTTTT | TTTTGAGACG | GAGTCTCGCT | 420
| CTGTCACCAG | GCTAGAGTGC | AGTGGTGCGA | TCCTGGCTCA | CTGCAACCTC | CGCTTCTCAG | 480
| GTTCAAGCGG | TTCTCCTGCC | TCAGCCTCCC | CTGCCACACC | CAGCTAATTT | TTTTGTACTT | 540
| TCAGTAGAGA | CAGGGTTTCA | CCATGTTGGC | CAGGATGACC | TCATGAGCTG | CCTGCCTCAG | 600
| CCTCCCAAAG | TGCTGGGATT | ACAGGTGTGA | GCCACCTGGG | GATTCTTTTT | ACAGCAACAT | 660
| TTTGCATTGA | GATTTGAAGT | CTTACAGATT | TTTATGATTA | TCTTTGCTAA | GAAATGGTTG | 720
| TGAGCTATAT | TTTACTTGCA | AGTAAGTTCA | ACTACCTTTG | ATTCATGGCA | GAAAATTCCT | 780
| TTGGGACTGT | AAAGTTTTCC | AGCGCTTCAT | GGTGTTGGCG | TTCAGCAGCA | GTGGGACCAT | 840
| GGTCATAGGT | GACGTGCCCT | GGCCCCTTGT | GCTGGTCATT | AGGGATACAG | CTCAGTGTAT | 900
| CTCATGAACT | CAACCGTGGT | GCCTTCTGAG | ACTTAATTC | AAATTATTTG | TATACTCTCT | 960
| TGTTCAGTGA | TTCTTAAAAG | AATTTGTTTT | GTTCCCAAAT | GTTTTCTTTT | TAATTGTTGT | 1020
| AGAAGAAATG | AGGAACGAGT | GAAAAGTTAA | TGAGCAAAAA | AAAAAAAAAA | AAAAGTTGGT | 1080
| TTATGTTTGC | ATTTTTAGAA | CGTAATTTGA | AAAATTACTC | CTCACTAAAG | GTAGTCGTTT | 1140
| TTTGCTATAT | ATAAGCGGCA | AAAGAAAATT | TACTATTTTT | TTGCATTAGA | GAGACTCCAA | 1200
| GTTGGCTGCA | GAAATTTTTC | TAGAAAATAA | GATAAATCTG | ATGGGAAAAC | TAGTAATCGG | 1260
| ATATCATGTT | GTGCAGCTGA | CTTGTTAGAA | ATCCTTTGAC | TCCCCCAATA | ATTCGTGAAC | 1320

| | | | | | | |
|---|---|---|---|---|---|---|
| TCAGAGAGCT | GAAAACATAC | AAACCACACC | ACCCCATGCA | TCTTTTTTTG | TCTTAGTCTT | 1380 |
| TTCTGCTCTG | TGTTTCTCTT | GGTATGGTGC | ACTATAATTG | GCTCCTATAG | AGAGAAAATA | 1440 |
| GCAAGTGAAT | CCCAGGACAT | ATTTTTCTCT | GCACAGAAAT | ATGAGTTAAG | CCAAAGTAAA | 1500 |
| CAAATTGCTT | TCACTACTCA | CCAGATAATA | ATTGTATTTT | GTTTTATTT | TTAG | 1554 |

(2) INFORMATION FOR SEQ ID NO:11:

(i) SEQUENCE CHARACTERISTICS:
        (A) LENGTH: 76 base pairs
        (B) TYPE: nucleic acid
        (C) STRANDEDNESS: double
        (D) TOPOLOGY: linear (ii) MOLECULE TYPE: DNA (genomic)

(viii) POSITION IN GENOME:
        (A) CHROMOSOME/SEGMENT: 4q35

(x) PUBLICATION INFORMATION:
        (A) AUTHORS: Weiner, Karen X.B.
                Weiner, Russell S.
                Maley, Frank
                Maley, Gladys F.
        (B) TITLE: Primary Structure of Human
                Deoxycytidylate Deaminase and Overexpression of Its
                Functional Protein in Escherichia coli
        (C) JOURNAL: J. Biol. Chem.
        (D) VOLUME: 268
        (E) ISSUE: 17
        (F) PAGES: 12983-12989
        (G) DATE: June 15-1993

(xi) SEQUENCE DESCRIPTION: SEQ ID NO:11:

| | | | | | | |
|---|---|---|---|---|---|---|
| GAAATTCATA | CCGAAGTGCA | GCAAGATTGT | CATTGACTTT | GATTCAATTA | ACAGCAGACC | 60 |
| GAGTCAAAAG | CTTCAG | | | | | 76 |

(2) INFORMATION FOR SEQ ID NO:12:

(i) SEQUENCE CHARACTERISTICS:
        (A) LENGTH: 1297 base pairs
        (B) TYPE: nucleic acid
        (C) STRANDEDNESS: double
        (D) TOPOLOGY: linear (ii) MOLECULE TYPE: DNA (genomic)

(viii) POSITION IN GENOME:
        (A) CHROMOSOME/SEGMENT: 4q35

(xi) SEQUENCE DESCRIPTION: SEQ ID NO:12:

| | | | | | | |
|---|---|---|---|---|---|---|
| TGAGTTACAT | CTCATTCAAT | CTCCAGAAGA | TTGGGATTAT | CGTCTTCTAA | GAGGTTGCTA | 60 |
| ATGCCTTTCA | TCTTGAAGTT | ACACATAACT | TCTTACTAGC | CAGTATGGCA | AAAGTAGGCA | 120 |
| TCTAAAGAAT | ATAAAGCCTC | AAATCTTCCT | TACTGTCTCT | CTTGTCACAT | GGAATCTACA | 180 |
| TGTGTTTGAA | CTATTGCTTT | AGGATTTAAA | ATAGGGAGC | CTGTGGTGGC | CTGGTGCACA | 240 |
| GGGCTAGAAC | GAGAGTGCCT | CCCCTTCTTG | TGTCCTGGCT | GGCTGGGATG | CTGGTGGCTC | 300 |
| TTCAGAGGAG | CATCAGCTGT | CTGTCATCTG | CTGCGATCCG | GCAGCCTCTC | TTCACTGCTA | 360 |
| CATGTGCTGG | AAGGACAAAT | AAATAATTGT | GGTTGTGTTC | TTAATGGGGA | CGAGCAGACA | 420 |
| CACTGATCTG | AACATCTGGC | CCAAGTGAAG | CATGGCATAT | AGTGCCCTTG | GAAGAAAATT | 480 |
| AGGCCTCAAA | TGACAGTAGC | ATTGAAGTGT | TTGCTGCAGA | GTTGAGGGAA | ACCCCAGCC | 540 |
| ACCCTCCCGG | AATCCGAGAT | AGGGTGGCAC | ATCTGTCCTG | ACAGACGAGG | AGTGTAACTG | 600 |
| AACCAGGAAT | ATTTCCTCCA | TTCCTGCTCT | CCCACTGCAC | ACAGGGTGGT | GGCACATTAT | 660 |

-continued

| | | | | | | |
|---|---|---|---|---|---|---|
|CCCTCTGGGG|GGTGGGGACG|CCTGTTGTTT|TGGCTCAATT|TGGGTTTGTT|GGTCACATGG|720|
|AGCTCTTCCA|TTTCGTTTAG|CTGAATAATG|AGTTGTTCCT|AGAGGAGACA|GCCTGTCTCT|780|
|CCTTGTTGCC|CCCAAAGCCC|ATGCCCTGCC|GTGGTGGCAG|CTGGGGCTGT|GGATGGGAGG|840|
|GGTCCCCAAC|ATGGATGTGT|TGCCCCTCCT|CCGCATGCCA|ACGCAGTTCA|TGTACAAGGC|900|
|CCCTCTGCAA|CTGGAGAGAA|AATTAATTCC|TATCCCGTGA|GTGGATTGTG|AGAAATTCCA|960|
|CCCACGTGGA|GACAGCTTAC|TGCAGCACTG|TTGGTGTTCG|GAGCTCTTCT|GTGCCCTGGC|1020|
|TCCATGCTTT|CACCTACACA|AGCATCACCT|TCCTAATCAC|CGCGGGGCGG|GGAGCGTGTG|1080|
|GCTCTGCCCC|TTCTCTTTAA|TCTCATTTAA|TTTTTATTAA|ACATGCTCAG|TACCTGTGTT|1140|
|GAGAAAAGGC|TTTCTTTATC|CTAAAGATTA|TTACCTTTTT|AAAGTGCTCT|TATATTTTCA|1200|
|TGAGTTTTTA|TTTTGTCTCT|GAGATTTTGT|ATTCCACATT|CTAGGGTATT|CTGTAATTTG|1260|
|GCTCCTTACC|AATATTATTA|AAATCTTATT|AAAATCT| | |1297|

( 2 ) INFORMATION FOR SEQ ID NO:13:

( i ) SEQUENCE CHARACTERISTICS:
        ( A ) LENGTH: 534 base pairs
        ( B ) TYPE: nucleic acid
        ( C ) STRANDEDNESS: single
        ( D ) TOPOLOGY: linear ( i i ) MOLECULE TYPE: cDNA ( x ) PUBLICATION INFORMATION:
        ( A ) AUTHORS: Weiner, Karen X.B.
                Weiner, Russell S.
                Maley, Frank
                Maley, Gladys F.
        ( B ) TITLE: Primary Structure of Human
                Deoxycytidylate Deaminase and Overexpression of Its
                Functional Protein in Escherichia coli
        ( C ) JOURNAL: J. Biol. Chem.
        ( D ) VOLUME: 268
        ( E ) ISSUE: 17
        ( F ) PAGES: 12983-12989
        ( G ) DATE: June 15-1993

( x i ) SEQUENCE DESCRIPTION: SEQ ID NO:13:

| | | | | | | |
|---|---|---|---|---|---|---|
|ATGAGTGAAG|TTTCCTGCAA|GAAACGGGAC|GACTATTTGG|AATGGCCAGA|GTATTTTATG|60|
|GCTGTGGCCT|TCTTATCAGC|ACAGAGAAGC|AAAGATCCAA|ATTCCCAGGT|CGGCGCCTGC|120|
|ATCGTGAATT|CAGAAAACAA|GATTGTCGGG|ATTGGGTACA|ATGGGATGCC|AAATGGGTGC|180|
|AGTGATGACG|TGTTGCCTTG|GAGAAGGACA|GCAGAGAATA|AGCTGGACAC|CAAATACCCG|240|
|TACGTGTGCC|ATGCGGAGCT|GAATGCCATC|ATGAACAAAA|ATTCGACCGA|TGTGAAAGGC|300|
|TGTAGTATGT|ATGTTGCCTT|GTTCCCTTGT|AATGAATGCG|CTAAGCTCAT|CATCCAGGCA|360|
|GGTATAAAAG|AAGTGATTTT|CATGTCTGAT|AAATACCATG|ATAGTGACGA|GGCAACTGCT|420|
|GCGAGGCTCC|TGTTTAATAT|GGCCGGGGTG|ACATTCCGGA|AATTCATACC|GAAGTGCAGC|480|
|AAGATTGTCA|TTGACTTTGA|TTCAATTAAC|AGCAGACCGA|GTCAAAAGCT|TCAG|534|

( 2 ) INFORMATION FOR SEQ ID NO:14:

( i ) SEQUENCE CHARACTERISTICS:
        ( A ) LENGTH: 178 amino acids
        ( B ) TYPE: amino acid
        ( D ) TOPOLOGY: linear ( i i ) MOLECULE TYPE: protein ( x ) PUBLICATION INFORMATION:
        ( A ) AUTHORS: Weiner, Karen X.B.
                Weiner, Russell S.

Maley, Frank
Maley, Gladys F.
( B ) TITLE: Primary Structure of Human
Deoxycytidylate Deaminase and Overexpression of Its
Functional Protein in Escherichia coli
( C ) JOURNAL: J. Biol. Chem.
( D ) VOLUME: 268
( E ) ISSUE: 17
( F ) PAGES: 12983-12989
( G ) DATE: June 15-1993

( x i ) SEQUENCE DESCRIPTION: SEQ ID NO:14:

```
Met Ser Glu Val Ser Cys Lys Lys Arg Asp Asp Tyr Leu Glu Trp Pro
1               5                   10                  15

Glu Tyr Phe Met Ala Val Ala Phe Leu Ser Ala Gln Arg Ser Lys Asp
            20              25                  30

Pro Asn Ser Gln Val Gly Ala Cys Ile Val Asn Ser Glu Asn Lys Ile
        35              40                  45

Val Gly Ile Gly Tyr Asn Gly Met Pro Asn Gly Cys Ser Asp Asp Val
    50              55                  60

Leu Pro Trp Arg Arg Thr Ala Glu Asn Lys Leu Asp Thr Lys Tyr Pro
65              70                  75                  80

Tyr Val Cys His Ala Glu Leu Asn Ala Ile Met Asn Lys Asn Ser Thr
            85                  90                  95

Asp Val Lys Gly Cys Ser Met Tyr Val Ala Leu Phe Pro Cys Asn Glu
            100             105                 110

Cys Ala Lys Leu Ile Ile Gln Ala Gly Ile Lys Glu Val Ile Phe Thr
        115             120                 125

Ser Asp Lys Tyr His Asp Ser Asp Glu Ala Thr Ala Ala Arg Leu Leu
    130             135                 140

Phe Asn Met Ala Gly Val Thr Phe Arg Lys Phe Ile Pro Lys Cys Ser
145             150                 155                 160

Lys Ile Val Ile Asp Phe Asp Ser Ile Asn Ser Arg Pro Ser Gln Lys
                165                 170                 175

Leu Gln
```